United States Patent
Stoltz et al.

(10) Patent No.: US 10,421,696 B2
(45) Date of Patent: Sep. 24, 2019

(54) ENANTIOSELECTIVE SYNTHESIS OF α-QUATERNARY MANNICH ADDUCTS BY PALLADIUM-CATALYZED ALLYLIC ALKYLATION

(71) Applicant: California Institute of Technology, Pasadena, CA (US)

(72) Inventors: Brian M. Stoltz, San Marino, CA (US); Yoshitaka Numajiri, Kamakura (JP); Beau P. Pritchett, Pasadena, CA (US); Koji Chiyoda, Gotenba (JP)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 14/972,475

(22) Filed: Dec. 17, 2015

(65) Prior Publication Data

US 2016/0176773 A1   Jun. 23, 2016

Related U.S. Application Data

(60) Provisional application No. 62/093,982, filed on Dec. 18, 2014.

(51) Int. Cl.
| | | |
|---|---|---|
| *C07B 53/00* | (2006.01) | |
| *C07D 209/88* | (2006.01) | |
| *C07D 211/74* | (2006.01) | |
| *C07D 211/76* | (2006.01) | |
| *C07D 265/32* | (2006.01) | |
| *C07C 271/18* | (2006.01) | |
| *C07C 271/50* | (2006.01) | |
| *C07C 311/16* | (2006.01) | |
| *C07C 233/76* | (2006.01) | |

(52) U.S. Cl.
CPC ............ *C07B 53/00* (2013.01); *C07C 233/76* (2013.01); *C07C 271/18* (2013.01); *C07C 271/50* (2013.01); *C07C 311/16* (2013.01); *C07D 209/88* (2013.01); *C07D 211/74* (2013.01); *C07D 211/76* (2013.01); *C07D 265/32* (2013.01); *C07B 2200/07* (2013.01); *C07C 2601/08* (2017.05); *C07C 2601/14* (2017.05); *C07C 2601/18* (2017.05); *C07C 2602/10* (2017.05)

(58) Field of Classification Search
CPC .................... C07D 211/76; C07D 401/12
See application file for complete search history.

(56) References Cited

U.S. PATENT DOCUMENTS 2,886,487 A    5/1959  Kupferberg
5,591,769 A    1/1997  Himmelsbach et al.
7,235,698 B2   6/2007  Behenna et al.
8,822,679 B2   9/2014  Stoltz et al.
10,035,769 B2  7/2018  Stoltz et al.
10,040,784 B2  8/2018  Stoltz et al.
10,106,479 B2  10/2018 Stoltz et al.
2006/0084820 A1  4/2006  Behenna et al.
2010/0298293 A1  11/2010 Allerheiligen et al.
2013/0267699 A1  10/2013 Stoltz et al.
2015/0105552 A1  4/2015  Stoltz et al.
2016/0096810 A1  4/2016  Stoltz et al.

(Continued)

FOREIGN PATENT DOCUMENTS

DE         668489 C       12/1938
WO      WO-9525088 A1     9/1995

(Continued)

OTHER PUBLICATIONS

Quirante et al. Journal of Organic Chemistry (2008), 73(2):768-771.*

(Continued)

*Primary Examiner* — Amanda L Aguirre
(74) *Attorney, Agent, or Firm* — Foley Hoag LLP; David P. Halstead; Janine S. Ladislaw

(57) ABSTRACT

This invention provides enantioenriched Mannich adducts with quaternary stereogenic centers and novel methods of preparing the compounds. Methods include the method for the preparation of a compound of formula (I):

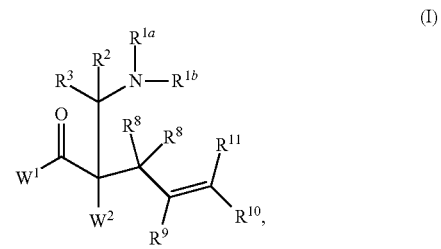

comprising treating a compound of formula (II):

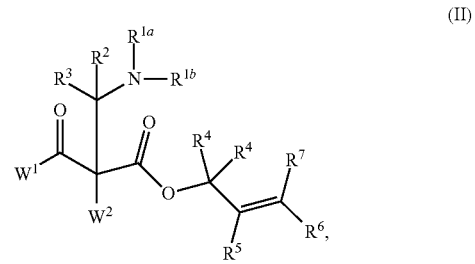

with a transition metal catalyst under alkylation conditions.

20 Claims, No Drawings

(56) References Cited

U.S. PATENT DOCUMENTS

2016/0176773 A1 6/2016 Stoltz et al.
2016/0280623 A1 9/2016 Stoltz et al.

FOREIGN PATENT DOCUMENTS

| WO | WO-2003/062265 | | 7/2003 |
|---|---|---|---|
| WO | WO-2005/012320 | A2 | 2/2005 |
| WO | WO-2009/013390 | A1 | 1/2009 |
| WO | WO-2009/153178 | A2 | 12/2009 |
| WO | WO-2011/153509 | A1 | 12/2011 |

OTHER PUBLICATIONS

Tsuji, et al. Organic & Biomolecular Chemistry (Aug. 2014), 12(40):7919-7922.*
Li et al. Synthetic Communications (2000), 30(13), 2317-2323.*
Yang et al. Youji Huaxue (2002), 22(7), 525-527.*
Melhado et al JACS 133, pp. 3517-3527 (2011).*
Li et al. Synthetic Comm. 30(13), pp. 2317-2323 (2000).*
Yang et al. Youji Huaxue 22(7), pp. 525-527 (2002).*
Roger Ruggeri et al. JOC 1987 52, 5745-5746. (Year: 1987).*
Heathcock et al. JOC 1992, 57, 2585-2594. (Year: 1992).*
CAS Registry No. 1823805-71-5, Entered STN: Dec. 6, 2015, American Chemical Society. (Year: 2015).*
Bell, et al., "Organocatalytic asymmetric deconjugative Michael additions," J Org Chem, 71(14): 5407-5410 (2006).
International Search Report and Written Opinion for International Application No. PCT/US2016/024238 dated Jul. 11, 2016.
Johnson, et al., "Asymmetric carbon-carbon bond formations in conjugate additions of lithiated N-boc allylic and benzylic amines to nitroalkenes: Enantioselective synthesis of substituted piperidines, pyrrolidines, and pyrimidinones," J Am Chem Soc, 124(39): 11689-11698 (2002).
Korch et al., "Enantioselective Synthesis of alpha-Secondary and alpha-Tertiary Piperazin-2-ones and Piperazines by Catalytic Asymmetric Allyllic Alkylation," Angew Chem Int Ed., 54: 179-183 (2015).
Marziale et al., "An Efficient Protocol for the Palladium-Catalyzed Asymmetric Decarboxylative Alllyllic Alkylation Using Low Palladium Concentrations and a Palladium(II) Precatalyst," Adv Synth Catal, 357: 2238-2245 (2015).
Numajiri, et al., "Enantioselective Synthesis of Dialkylated N-Heterocycles by Palladium-Catalyzed Allylic Alkylation," Organic Letters, 2015 pp. 1082-1085.
Sherden, "Mechanistic investigations into the palladium-catalyzed decarboxylative allylic alkylation of ketone enolates using the PHOX ligand architecture," Chapter 1, Dissertation, California Institute of Technology (2011). Retrieved from the Internet: <http://thesis.library.caltech.edu/6476/2/03-Chpt_1_Intro.pdf.>.
Williams, et al., "Asymmetric synthesis of monosubstituted and alpha,alpha-disubstituted alpha-amino acids via diastereoselective glycine enolate alkylations," J Am Chem Soc, 113(24): 9276-9286 (1991).
Yendapally, et al., "Design, synthesis, and evaluation of novel ethambutol analogues," Bioorg Med Chem Lett, 18(5):1607-1611 (2008).
Zawisza, et al., "An unexpected palladium-catalyzed cyclization of bis-hydroxy allylic alcohols to dioxabicyclo[2.2.2]octanes," Tetrahedron Lett, 47(19): 3271-3274 (2006).
Zawisza, et al., "Palladium-catalyzed formation of cyclic ethers-regio-, stereo- and enantioselectivity of the reaction," Eur J Org Chem, 2007(14): 2296-2309 (2007).
Amat et al., "Enantioselective Synthesis of 3,3-Disubstituted Piperidine Derivatives by Enolate Dialkylation of Phenylglycinol-derived oxazolopiperidone Lactams," J. Org. Chem., 72:4431-4439 (2007).
Bach, T., "Regioselective Reducing Ring Opening of 2-(2-Hydroxyphenyl)-3-[(trimethylsilyl)oxy]oxetanes at the More Substituted C-2-Position", No. 7 (1997).
Badillo et al., "Enantioselective synthesis of substituted oxindoles and spirooxindoles with applications in drug discovery," Current Opinion in Drug Discovery & Development, 13(6):758-776 (2010).
Baussanne et al., "Diastereoselective Bis-Alkylation of Chiral Non-Racemic α,β-Unsaturated γ-Lactams," Tetrahedron Letters, 35(23):3931-3934 (1994).
Behenna and Stoltz, "The Enantioselective Tsuji Allylation," J. Am. Chem. Soc., 126(46):15044-15045 (2004).
Behenna et al., "Enantioselective construction of quaternary N-heterocycles by palladium-catalysed decarboxylative allylic alkylation of lactams", Nature Chem. 2012, 4, 130.
Behenna et al., "Enantioselective Decarboxylative Alkylation Reactions: Catalyst Developement, Substrate Scope, and Mechanistic Studies", Chem. Eur. J. 2011, 17, 14199.
Bennett et al., "A Unified Approach to the Daucane and Sphenolobane Bicyclo[5.3.0]decane Core: Enantioselective Total Synthesis of Daucene, Daucenal, Epoxydaucenal B, and 14-para-Anisoyloxydauc-4,8-diene", Chem. Eur. J. 2013, 52, 17745.
Bennett et al., "Expanding Insight into Asymmetric Palladium-Catalyzed Allylic Alklation of N-Heterocyclic Molecules and Cyclic Ketones", Chem. Eur. J. 2013, 19, 4414.
Bennett et al., Synthesis of enantioenriched γ-quaternary cycloheptenones using a combined allylic alkylation/Stork-Danheiser approach: preparation of mono-, bi-, and tricyclic systems, Org. Biomol. Chem. 2012, 10, 56.
Bobranski et al., Hydration of Phenyldiallylacetamide, 7, Bulletin De L'Academie Polonaise De Sciences, Serie Des Sciences, Chimiques, Geologiques Et Geographiques, pp. 399-401 (1959) (CAS Abstract).
Bulman et al., "Short and Versatile Route to a Key Intermediate for Lactacystin Synthesis", Organic Letters, vol. 5, No. 3, pp. 353-355 (2003).
Coates et al., "Efficient synthesis of 3-substituted lactams using Meerwein Eschenmoser Claisen [3,3] sigmatropic rearrangements", 32(33) Tetrahedron Letts. 4199-202 (1991) (CAS Abstract).
Day et al., "The Catalytic Enantioselective Total Synthesis of (+)-Liphagal," Angew. Chem. Int. Ed., 50:6814-6818 (2011).
Desmaele et al., "Stereocontrolled Elaboration of Quaternary Carbon Centers through the Asymmetric Michael-Type Alkylation of Chiral Imines/Secondary Enamines: Enantioselective Synthesis of (+)-Vincamine,", J. Org. Chem., 62:3890-3901 (1997).
Enders et al., "Asymmetric Electrophilic Substitutions at the α-Position of γ- and δ-Lactams," Eur. J. Org. Chem., pp. 4463-4477 (2001).
Enquist and Stolz, "The total synthesis of (−)-cyanthiwigin F by means of double catalytic enantioselective alkylation," Nature, 453:1228-1231 (2008).
Enquist et al., "Total Syntheses of Cyanthiwigins B, F, and G", Chem. Eur. J. 2011, 17, 9957.
Ezquerra et al., "Stereoselective Double Alkylation of Ethyl N-Boc-pyroglutamate," J. Org. Chem., 59(15):4327-4331 (1994).
Fuji et al., "Addition-elimination strategy for asymmetric induction: a chiral sulfoxide as a leaving group", 31 (17) Tetrahedron Letts. 2419-22 (1990) (CAS abstract).
Gartshore et al., "Enantioselective Palladium-Catalyzed Decarboxylative Allylation of Carbazolones and Indolones: Formal Synthesis of (+)-Kopsihainanine A", Angew Chem. Int. Ed. 2013, 52, 4113.
Groaning and Meyers, "Chiral Non-Racemic Bicyclic Lactams. Auxiliary-Based Asymmetric Reactions," Tetrahedron, 56(549):9843-9873 (2000).
Helmchen and Pfaltz, "Phosphinooxazolines—A New Class of Versatile, Modular P,N-Ligands for Asymmetric Catalysis," Acc. Chem. Res., 33(6):336-345 (2000).
Hong et al., "Biosynthesis and Chemical Synthesis of Presilphiperfolanol Natural Products", Angew. Chem. Int. Ed. 2014, 53, 5248.
Hong et al., "Enantioselective Total Synthesis of the Reported Structures of (−)-9-epi-Presilphiperfolan-1-ol and (−)-Presilphiperfolan-1-ol: Structural Confirmation and Reassignment and Biosynthetic Insights", Angew. Chem. Int. Ed. 2012, 51, 9674.
Hong et al., "Palladium-catalyzed asymmetric alkylation in the synthesis of cyclopentanoid and cycloheptanoid core structures bearing all-carbon quaternary stereocenters", Tetrahedron 2011, 67, 10234.

(56) References Cited

OTHER PUBLICATIONS

Hong et al., "The Construction of All-Carbon Quaternary Stereocenters by Use of Pd-Catalyzed Asymmetric Allylic Alkylation Reactions in Total Synthesis", Eur. J. Org. Chem. 2013, 14, 2745.
Imao et al., "Easy Access to Esters with a Benzylic Quaternary Carbon Center from Diallyl Malonates by Palladium-Catalyzed Decarboxylative Allylation," J. Org. Chem., 72:1652-1658 (2007).
Jakubec et al., "Enantio- and diastereoselective Michael additions of C-succinimidyl esters to nitro olefins using cinchonine-derived bifunctional organocatalysts," Tetrahedron: Asymmetry, 22:1147-1155 (2011).
Jing et al., " Total Synthesis of (+)-Kopsihainanine A", Chem. Eur. J. 2012, 18, 6729.
Juaristi et al., Enantioselective synthesis of β-amino acids. Part 9: Preparation of enantiopure α,α-disubstituted α-amino acids from 1-benzoyl-2(S)-tert-butyl-3-methylperhydropyrimidin-4-one1,2, Tetrahedron: Asymmetry, 9:3881-3888 (1998).
Keith et al., "The Reaction Mechanism of the Enantioselective Tsuji Allylation: Inner-Sphere and Outer-Sphere Pathways, Internal Rearrangements, and Asymmetric C—C Bond Formation", J. Am. Chem. Soc. 2012, 134, 19050.
Kim et al., An Asymmetric Synthesis of (+)-Isonitramine by 'Triple Allylic Strain-Controlled' Intramolecular SN2' Alkylation, Tetrahedron Letters, 37(9):1433-1434 (1996).
Li et al., "Enantioselective Palladium-Catalyzed Decarboxylative Allylation of Carbazolones: Total Synthesis of (−)-Aspidospermidine and (+)-Kopsihainanine A", Angew Chem. Int. Ed. 2013, 52, 4117.
Liu et al., "Construction of Vicinal Tertiary and All-Carbon Quaternary Stereocenters via Ir-Catalyzed Regio-, Diastereo-, and Enantioselective Allylic Alkylation and Applications in Sequential Pd Catalysis", J. Am. Chem. Soc. 2013, 135, 10626.
Lu and Ma, "Metal-Catalyzed Enantioselective Allylation in Asymmetric Synthesis," Angew. Chem. Int. Ed., 47:258-297 (2008).
Ma et al., "Palladium-catalyzed decarboxylative allylic alkylation of diastereomeric β-ketoesters", Tetrahedron 2014, 70, 4208.
McDougal et al., "High-Throughput Screening of the Asymmetric Decarboxylative Alkylation Reaction of Enolate-Stabilized Enol Carbonates," Synlett, 11:1712-1716 (2010).
McDougal et al., "Rapid synthesis of an electron-deficient t-BuPHOX ligand: cross-coupling of aryl bromides with secondary phosphine oxides," Tetrahedron Letters, 51:5550-5554 (2010).
McFadden and Stoltz, "The Catalytic Enantioselective, Protecting Group-Free Total Synthesis of (+)-Dichroanone," J. Am. Chem. Soc., 128:7738-7739 (2006).
Mertes et al., "Glutarimides", J.Am.Pharma. Assoc. vol. 67, pp. 882-885, (1912-1977) (1958) (CAS Abstract).
Meyers et al., "Stereoselective Alkylations in Rigid Systems. Effect of Remote Substituents on π-Facial Additions to Lactam Enolates. Stereoelectronic and Steric Effects," J. Am. Chem. Soc., 120:7429-7438 (1998).
Mohr and Stoltz, "Enantioselective Tsuji Allylations," Chem. Asian J., 2:1476-1491 (2007).
Mohr et al., "Deracemization of Quaternary Stereocenters by Pd-Catalyzed Enantioconvergent Decarboxylative Allylation of Racemic β-Ketoesters," Angew. Chem. Int. Ed., 44:6924-6927 (2005).
Moss et al., "Catalytic Enantio- and Diastereoselective Alkylations with Cyclic Sulfamidates," Angew. Chem. Int. Ed., 49:568-571 (2010).
Numajiri et al., "Enantioselective synthesis of a-quaternary mannich adducts by palladium-catalyzed allylic alkylation: Total synthesis of (+)-sibirinine," J Am Chem Soc, 137:1040-3 (2015).
Ojima and Pei, "Asymmetric Synthesis with Chiral β-Lactams. Highly Stereoselective Alkylation and Aldol Reaction of a Chiral 3-Amino-4-Styryl-β-Lactam," Tetrahedron Letters, 31(7):977-980 (1990).
Padwa et al., "A Novel Cycloaddition Reaction of α-Diazo-γ-amido Ketones Catalyzed by Rhodium (II) Acetate. Scope and Mechanistic Details of the Process", 61(7) J. Org. Chem. 2283-92 (1996) (CAS Abstract).

Park et al., "Highly Enantioselective Phase-Transfer Catalytic α-Alkylation of α-tert-Butoxycarbonyllactams: Construction of β-Quaternary Chiral Pyrrolidine and Piperidine Systems," Adv. Synth. Catal., 353:3313-3318 (2011).
Reeves et al., "Development of (Trimethylsilyl)ethyl Ester Protected Enolates and Applications in Palladium-Catalyzed Enantioselective Allylic Alkylation: Intermolecular Cross-Coupling of Functionalized Electrophiles", Org. Lett. 2014, 16, 2314.
Reeves, et al., "Enantioselective Construction of α-Quaternary Cyclobutanones by Catalytic Asymmetric Allylic Alkylation", Angew. Chem. Int. Ed. 2013, 52, 6718.
Rodriguez et al., "Carba Peptide Bond Surrogates/Different Approaches to Gly-(CH2—CH2)-D,L-XAA Pseudopeptide Units", International Journal of Peptide and Protein Research, vol. 39, No. 3, pp. 273-277 (1992).
Schwarz and Meyers, "Tandem α-Cyano Enamine/Enolate Alkylations on Bicyclic Lactams: Asymmetric Carbocycle and Heterocycle Synthesis," J. Org. Chem., 63(5):1619-1629 (1998).
Search Report from International Application No. PCT/US2012/043904 dated Feb. 1, 2013.
Seto et al., "Catalytic Enantioselective Alkylation of Substituted Dioxanone Enol Ethers: Ready Access to C(α)-Tetrasubstituted Hydroxyketones, Acids, and Esters," Angew. Chem. Int. Ed., 47:6873-6876 (2008).
Shibuya et al., "Enantioselective Synthesis of 5-6-7 Carbocyclic Core of the Gagunin Diterpenoids", Org. Lett. 2013, 15, 3480.
Streuff et al., "A palladium-catalysed enolate alkylation cascade for the formation of adjacent quaternary and tertiary sterocentres," Nature Chemistry, 2:192-196 (2010).
Takahashi et al., "Atropisomeric lactam chemistry: catalytic enantioselective synthesis, application to asymmetric enolate chemistry and synthesis of key intermediates for NET inhibitors," Tetrahedron, 66:288-296 (2010).
Tani et al., "A Facile and Modular Synthesis of Phosphinooxazoline Ligands," Organic Letters, 9(13):2529-2531 (2007).
Tari et al., "Recoverable Cinchona ammonium salts as organocatalysts in the enantioselective Michael addition of β-Keto esters," Tetrahedron: Asymmetry, 21:2872-2878 (2010).
Trost and Brennan, "Asymmetric Synthesis of Oxindole and Indole Spirocyclic Alkaloid Natural Products," Synthesis, 18:3003-3025 (2009).
Trost et al., "Enantioselective Synthesis of [alpha]-Tertiary Hydroxyaldehydes by Palladium-Catalyzed Asymmetric Allylic Alkylation of Enolates", Journal of the American Chemical Society, vol. 129, No. 2, pp. 282-283 (2007).
Trost, Barry M., "Asymmetric Allylic Alkylation, an Enabling Methodology," J. Org. Chem., 69(18):5813-5837 (2004).
Varea et al., "Asymmetric Synthesis. XXXV1. Synthesis of 2-Methyl 5-Substituted Piperidines from Chiral Non-racemic Lactams," Tetrahedron Letters, 36(7):1035-1038 (1995).
Vijn et al., "Highly Enantioselective Synthesis of a 2,3-Dihydroindole Mediated by N-Methylephedrine," Angew. Chem. Int. Ed. Engl., 23(2):165-166 (1984).
Weaver et al., "Transition Metal-Catalyzed Decarboxylative Allylation and Benzylation Reactions," Chem. Rev., 111:1846-1913 (2011).
White et al., "The Catalytic Asymmetric Total Synthesis of Elatol," J. Am. Chem. Soc., 130(3):810-811 (2008).
Written Opinion from International Application No. PCT/US2012/043904 dated Feb. 1, 2013.
Zhou et al., "Catalytic Asymmetric Synthesis of Oxindoles Bearing a Tetrasubstituted Stereocenter at the C-3 Position," Adv. Synth. Catal., 352:1381-1407 (2010).
Hayashi et al., "Ni-Catalyzed Enantioselective C-Acylation of a-Substituted Lactams," J Am Chem Soc, 138(29):8997-9000 (2016).
International Search Report and Written Opinion for International Application No. PCT/US2017/021528 dated May 25, 2017.
Tasker et al., "Recent advances in homogeneous nickel catalysis," Nature, 509(7500): 299-309 (2014).
Zhang et al., "Direct N-Acylation of Lactams, Oxazolidinones, and Imidazolidinones with Aldehydes by Shvo's Catalyst," Org Lett, 14(17): 4646-4649 (2012).
U.S. Appl. No. 13/531,485, Granted.
U.S. Appl. No. 13/797,736, Abandoned.

(56) References Cited

OTHER PUBLICATIONS

U.S. Appl. No. 15/366,590, Granted.
U.S. Appl. No. 16/049,434, Pending.
U.S. Appl. No. 14/514,001, Granted.
U.S. Appl. No. 14/877,496, Abandoned.
U.S. Appl. No. 15/081,157, Granted.
U.S. Appl. No. 16/166,893, Pending.
U.S. Appl. No. 15/454,198, Granted.
U.S. Appl. No. 16/055,559, Pending.

* cited by examiner

ENANTIOSELECTIVE SYNTHESIS OF α-QUATERNARY MANNICH ADDUCTS BY PALLADIUM-CATALYZED ALLYLIC ALKYLATION

RELATED APPLICATIONS

This application claims the benefit of U.S. Provisional Application 62/093,982, filed Dec. 18, 2014, the content of which is incorporated herein by reference.

GOVERNMENT SUPPORT

This invention was made with Government support under Grant Number R01GM080269, awarded by the National Institutes of Health. The Government has certain rights in the invention.

BACKGROUND OF THE INVENTION

The Mannich reaction, first discovered in the early 20th century, is among the most robust reactions known to produce nitrogen-containing compounds. In a classic intermolecular Mannich reaction, an aldehyde, an amine and an α-acidic carbonyl compound react to form a β-amino carbonyl compound. Recent progress in this area, including modified imine donors and well-explored catalyst systems, has made available a wide variety of asymmetric α-functionalizations of carbonyl compounds. However, to date, asymmetric Mannich-type reactions to establish α-quaternary carbonyl compounds have been limited to specialized substrate classes.

There exists a need for methods that enable access to α-quaternary Mannich Adducts, particularly enantioselective methods to provide enantioenriched products.

SUMMARY OF THE INVENTION

In one aspect, the present invention provides methods for preparing a compound of formula (I):

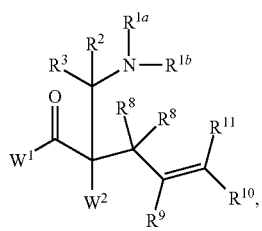

(I)

comprising treating a compound of formula (II):

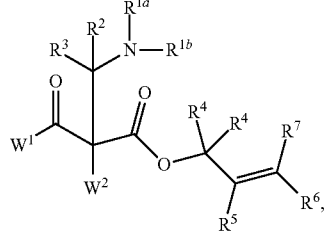

(II)

with a transition metal catalyst under alkylation conditions, wherein, as valence and stability permit, $R^{1a}$ and $R^{1b}$ each independently represent hydrogen or optionally substituted alkyl, cycloalkyl, (cycloalkyl)alkyl, aryl, aralkyl, heteroaryl, heteroaralkyl, alkenyl, alkynyl, —C(O)alkyl, —C(O)aryl, —C(O)aralkyl, —C(O)heteroaryl, —C(O)heteroaralkyl, —C(O)O(alkyl), —C(O)O(aryl), —C(O)O(aralkyl), —C(O)O(heteroaryl), —C(O)O(heteroaralkyl), —S(O)$_2$(aryl), —S(O)$_2$(alkyl), —S(O)$_2$(haloalkyl), —OR$^{14}$, —SR$^{14}$, or —NR$^{14}$R$^{15}$;

$R^2$ and $R^3$ each independently represent hydrogen or substituted or unsubstituted alkyl, aralkyl, aryl, heteroaralkyl, heteroaryl, (cycloalkyl)alkyl, cycloalkyl, (heterocycloalkyl)alkyl, heterocycloalkyl, alkenyl, alkynyl, alkylamino, hydroxyalkyl, alkoxyalkyl, aminoalkyl, or thioalkyl;

or wherein $R^{1a}$ and $R^2$ are taken together with the intervening atoms to form an optionally substituted heterocyclic ring;

$R^4$, $R^5$, $R^6$, $R^7$, $R^8$, $R^9$, $R^{10}$, and $R^{11}$ are each independently selected for each occurrence from hydrogen, hydroxyl, halogen, nitro, alkyl, alkenyl, alkynyl, cyano, carboxyl, sulfate, amino, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, acyl, acyloxy, acylamino, aryl, heteroaryl, cycloalkyl, heterocycloalkyl, aralkyl, arylalkoxy, heteroaralkyl, (cycloalkyl)alkyl, and (heterocycloalkyl)alkyl;

$W^1$ and $W^2$ are each independently selected from alkyl, alkenyl, alkynyl, OR$^{12}$, SR$^{12}$, or NR$^{12}$R$^{13}$; or $W^1$ and $W^2$, taken together with the intervening atoms, form an optionally substituted heterocycloalkyl, cycloalkyl, heterocycloalkenyl, or cycloalkenyl group;

$R^{12}$ and $R^{13}$ are independently selected for each occurrence from hydrogen or substituted or unsubstituted alkyl, aralkyl, aryl, heteroaralkyl, heteroaryl, (cycloalkyl)alkyl, cycloalkyl, (heterocycloalkyl)alkyl, heterocycloalkyl, alkenyl, alkynyl, hydroxyalkyl, alkoxyalkyl, aminoalkyl, and thioalkyl; and $R^{14}$ and $R^{15}$ are independently selected for each occurrence from hydrogen or substituted or unsubstituted alkyl, aralkyl, aryl, heteroaralkyl, heteroaryl, (cycloalkyl)alkyl, cycloalkyl, (heterocycloalkyl)alkyl, heterocycloalkyl, alkenyl, and alkynyl.

In another aspect, the present invention provides an α-quaternary Mannich type product having the structure of formula (I),

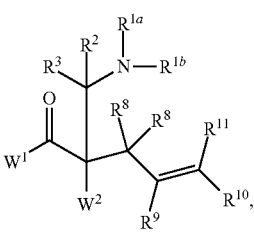

(I)

or a salt thereof;
wherein:
$R^{1a}$ and $R^{1b}$ each independently represent hydrogen or optionally substituted alkyl, cycloalkyl, (cycloalkyl)alkyl, aryl, aralkyl, heteroaryl, heteroaralkyl, alkenyl, alkynyl, —C(O)alkyl, —C(O)aryl, —C(O)aralkyl, —C(O)heteroaryl, —C(O)heteroaralkyl, —C(O)O(alkyl), —C(O)O(aryl), —C(O)O(aralkyl), —C(O)O(heteroaryl), —C(O)O(heteroaralkyl), —S(O)$_2$(aryl), —S(O)$_2$(alkyl), —S(O)$_2$(haloalkyl), —OR$^{14}$, —SR$^{14}$, or —NR$^{14}$R$^{15}$;

R$^2$ and R$^3$ each independently represent hydrogen or substituted or unsubstituted alkyl, aralkyl, aryl, heteroaralkyl, heteroaryl, (cycloalkyl)alkyl, cycloalkyl, (heterocycloalkyl)alkyl, heterocycloalkyl, alkenyl, alkynyl, alkylamino, hydroxyalkyl, alkoxyalkyl, aminoalkyl, or thioalkyl;

or wherein R$^{1a}$ and R$^2$ are taken together with the intervening atoms to form an optionally substituted heterocyclic ring;

R$^8$, R$^9$, R$^{10}$, and R$^{11}$ are independently selected for each occurrence from hydrogen, hydroxyl, halogen, nitro, alkyl, alkenyl, alkynyl, cyano, carboxyl, sulfate, amino, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, acyl, acyloxy, acylamino, aryl, heteroaryl, cycloalkyl, heterocycloalkyl, aralkyl, arylalkoxy, heteroaralkyl, (cycloalkyl)alkyl, and (heterocycloalkyl)alkyl;

W$^1$ and W$^2$ are each independently selected from alkyl, alkenyl, alkynyl, OR$^{12}$, SR$^{12}$, or NR$^{12}$R$^{13}$; or W$^1$ and W$^2$, taken together with the intervening atoms, form an optionally substituted heterocycloalkyl, cycloalkyl, heterocycloalkenyl, or cycloalkenyl group;

R$^{12}$ and R$^{13}$ are independently selected for each occurrence from hydrogen or substituted or unsubstituted alkyl, aralkyl, aryl, heteroaralkyl, heteroaryl, (cycloalkyl)alkyl, cycloalkyl, (heterocycloalkyl)alkyl, heterocycloalkyl, alkenyl, alkynyl, hydroxyalkyl, alkoxyalkyl, aminoalkyl, and thioalkyl; and R$^{14}$ and R$^{15}$ are independently selected for each occurrence from hydrogen or substituted or unsubstituted alkyl, aralkyl, aryl, heteroaralkyl, heteroaryl, (cycloalkyl)alkyl, cycloalkyl, (heterocycloalkyl)alkyl, heterocycloalkyl, alkenyl, and alkynyl.

In another aspect, the present invention provides a compound having the structure of formula (II),

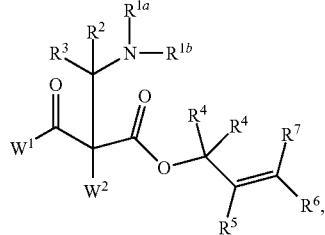

(II)

or a salt thereof;
wherein:

R$^{1a}$ and R$^{1b}$ each independently represent hydrogen or optionally substituted alkyl, cycloalkyl, (cycloalkyl)alkyl, aryl, aralkyl, heteroaryl, heteroaralkyl, alkenyl, alkynyl, —C(O)alkyl, —C(O)aryl, —C(O)aralkyl, —C(O)heteroaryl, —C(O)heteroaralkyl, —C(O)O(alkyl), —C(O)O(aryl), —C(O)O(aralkyl), —C(O)O(heteroaryl), —C(O)O(heteroaralkyl), —S(O)$_2$(aryl), —S(O)$_2$(alkyl), —S(O)$_2$(haloalkyl), —OR$^{14}$, —SR$^{14}$, or —NR$^{14}$R$^{15}$;

R$^2$ and R$^3$ each independently represent hydrogen or substituted or unsubstituted alkyl, aralkyl, aryl, heteroaralkyl, heteroaryl, (cycloalkyl)alkyl, cycloalkyl, (heterocycloalkyl)alkyl, heterocycloalkyl, alkenyl, alkynyl, alkylamino, hydroxyalkyl, alkoxyalkyl, aminoalkyl, or thioalkyl;

or wherein R$^{1a}$ and R$^2$ are taken together with the intervening atoms to form an optionally substituted heterocyclic ring;

R$^4$, R$^5$, R$^6$, and R$^7$ are independently selected for each occurrence from hydrogen, hydroxyl, halogen, nitro, alkyl, alkenyl, alkynyl, cyano, carboxyl, sulfate, amino, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, acyl, acyloxy, acylamino, aryl, heteroaryl, cycloalkyl, heterocycloalkyl, aralkyl, arylalkoxy, heteroaralkyl, (cycloalkyl)alkyl, and (heterocycloalkyl)alkyl;

W$^1$ and W$^2$ are each independently selected from alkyl, alkenyl, alkynyl, OR$^{12}$, SR$^{12}$, or NR$^{12}$R$^{13}$; or W$^1$ and W$^2$, taken together with the intervening atoms, form an optionally substituted heterocycloalkyl, cycloalkyl, heterocycloalkenyl, or cycloalkenyl group;

R$^{12}$ and R$^{13}$ are independently selected for each occurrence from hydrogen or substituted or unsubstituted alkyl, aralkyl, aryl, heteroaralkyl, heteroaryl, (cycloalkyl)alkyl, cycloalkyl, (heterocycloalkyl)alkyl, heterocycloalkyl, alkenyl, alkynyl, hydroxyalkyl, alkoxyalkyl, aminoalkyl, and thioalkyl; and R$^{14}$ and R$^{15}$ are independently selected for each occurrence from hydrogen or substituted or unsubstituted alkyl, aralkyl, aryl, heteroaralkyl, heteroaryl, (cycloalkyl)alkyl, cycloalkyl, (heterocycloalkyl)alkyl, heterocycloalkyl, alkenyl, and alkynyl.

DETAILED DESCRIPTION OF THE INVENTION

I. Definitions

The definitions for the terms described below are applicable to the use of the term by itself or in combination with another term.

The term "acyl" is art-recognized and refers to a group represented by the general formula hydrocarbyl-C(O)—, preferably alkyl-C(O)—.

The term "acylamino" is art-recognized and refers to an amino group substituted with an acyl group and may be represented, for example, by the formula hydrocarbyl-C(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond that is straight chained or branched and has from 1 to about 20 carbon atoms, preferably from 1 to about 10 unless otherwise defined. The term "alkenyl" is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl such as an alkylC(O)), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a silyl ether, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthiols, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-tirfluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkyl-S—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

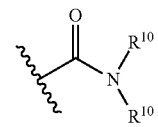

wherein each $R^{10}$ independently represent a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

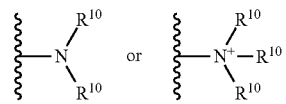

wherein each $R^{10}$ independently represents a hydrogen or a hydrocarbyl group, or two $R^{10}$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group. An aralkyl group is connected to the rest of the molecule through the alkyl component of the aralkyl group.

The term "aryl" as used herein include substituted or unsubstituted single-ring aromatic groups in which each atom of the ring is carbon. Preferably the ring is a 5- to 10-membered ring, more preferably a 6- to 10-membered ring or a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like. Exemplary substitution on an aryl group can include, for example, a halogen, a haloalkyl such as trifluoromethyl, a hydroxyl, a carbonyl (such as a carboxyl, an alkoxycarbonyl, a formyl, or an acyl such as an alkylC(O)), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a silyl ether, a sulfhydryl, an alkylthio, a sulfate, a sulfonate, a sulfamoyl, a sulfonamido, a sulfonyl, a heterocyclyl, an aralkyl, or an aromatic or heteroaromatic moiety The term "carbamate" is art-recognized and refers to a group

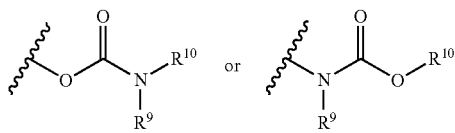

wherein $R^9$ and $R^{10}$ independently represent hydrogen or a hydrocarbyl group, such as an alkyl group, or $R^9$ and $R^{10}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be susbstituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group $-OCO_2-R^{10}$, wherein $R^{10}$ represents a hydrocarbyl group.

The term "carboxyl", as used herein, refers to a group represented by the formula $-CO_2H$.

The term "ester", as used herein, refers to a group $-C(O)OR^{10}$ wherein $R^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a heteroaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include 5- to 10-membered cyclic or polycyclic ring systems, including, for example, pyrrole, furan, thiophene, imidazole, oxazole, thiazole, pyrazole, pyridine, pyrazine, pyridazine, and pyrimidine, and the like. Exemplary optional substituents on heteroaryl groups include those substituents put forth as exemplary substituents on aryl groups, above.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto. A "silyl ether" refers to a silyl group linked through an oxygen to a hydrocarbyl group. Exemplary silyl ethers include —OSi(CH$_3$)$_3$ (—OTMS), —OSi(CH$_3$)$_2$t-Bu (—OTBS), —OSi(Ph)$_2$t-Bu (—OTBDPS), and —OSi(iPr)$_3$ (—OTIPS).

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a haloalkyl, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

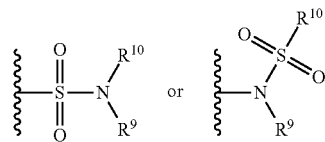

wherein R$^9$ and R$^{10}$ independently represents hydrogen or hydrocarbyl, such as alkyl, or R$^9$ and R$^{10}$ taken together with the intervening atom(s) complete a heterocycle having from 4 to 8 atoms in the ring structure.

The term "sulfoxide" is art-recognized and refers to the group —S(O)—R$^{10}$, wherein R$^{10}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—R$^{10}$, wherein R$^{10}$ represents a hydrocarbyl.

The term "thioalkyl", as used herein, refers to an alkyl group substituted with a thiol group.

The term "thioester", as used herein, refers to a group —C(O)SR$^{10}$ or —SC(O)R$^{10}$ wherein R$^{10}$ represents a hydrocarbyl.

The term "thioether", as used herein, is equivalent to an ether, wherein the oxygen is replaced with a sulfur.

The term "urea" is art-recognized and may be represented by the general formula

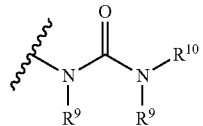

wherein R$^9$ and R$^{10}$ independently represent hydrogen or a hydrocarbyl, such as alkyl, or either occurrence of R$^9$ taken together with R$^{10}$ and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

II. Description of the Invention

This invention is based on the discovery that enantioenriched α-quaternary Mannich adducts of α-alkyl-substituted ketones could be accessed via aminomethylation followed by allylic alkylation (Scheme 1). Introduction of an aminomethyl group to β-keto ester V using classical Mannich chemistry (V to VI), followed by an asymmetric allylic alkylation reaction would provide the enantioenriched α-quaternary ketone product VII. Compound VII can be thought of as an α-aminomethylation product of the so-called "thermodynamic" enolate.

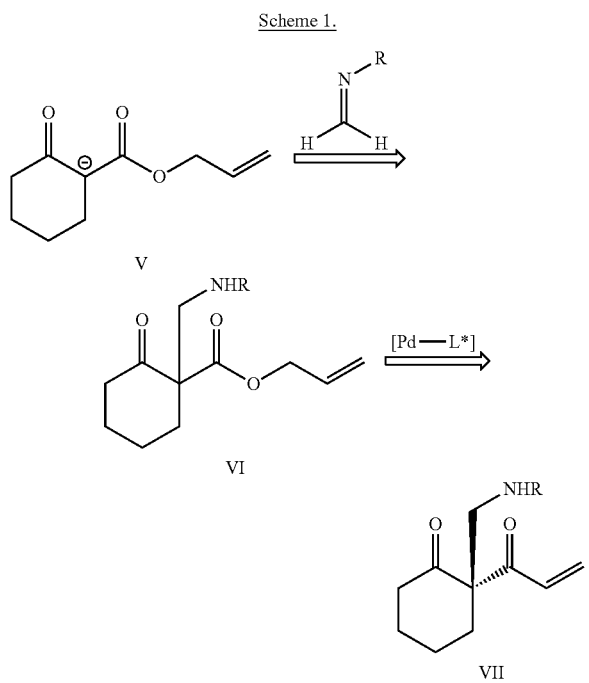

The use of β-oxo esters circumvents any undesired regioselectivity in the aminomethylation step. Next, a palladium-catalyzed decarboxylation event furnishes the desired enolate intermediate under conditions amenable to enantioinduction. As demonstrated herein, these reactions proceed in high yield and enantioselectivity. The decarboxylative allylic alkylation reaction is catalyzed by a transition metal catalyst and a chiral ligand, and the products can be quickly and efficiently elaborated into complex products exhibiting biological activity.

According to embodiments of the present invention, a wide range of structurally-diverse, functionalized α-quaternary Mannich-type products are prepared in a two-step sequence by (i) Mannich reaction followed by (ii) a stereoselective method of palladium-catalyzed enantioselective enolate allylic alkylation. In effect, the methods enable access to asymmetric Mannich-type products of "thermodynamic" enolates of substrates possessing additional enolizable positions and acidic protons. Palladium-catalyzed decarboxylative allylic alkylation enables the enantioselective synthesis of five-, six-, and seven-membered ketone, lactam, and other heterocyclic systems. The mild reaction conditions are notable given the free N—H groups and high functional group tolerance in each of the substrates. Indeed, the utility of this method is highlighted in the first total synthesis of (+)-sibirinine.

In some embodiments of the present invention, a method of making an α-quaternary Mannich-type product comprises reacting a substrate compound with a ligand in the presence of a palladium-based catalyst and a solvent. The palladium-based catalysts, ligands and solvents useful in this reaction are described in more detail below in Section IV.

III. Compounds of the Invention

In certain embodiments, the invention relates to a compound of formula (I),

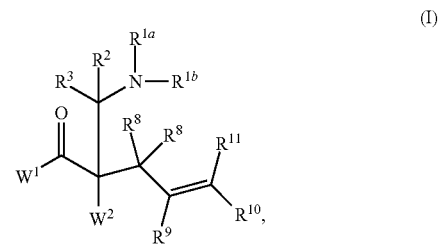

or a salt thereof;
wherein:
$R^{1a}$ and $R^{1b}$ each independently represent hydrogen or optionally substituted alkyl, cycloalkyl, (cycloalkyl)alkyl, aryl, aralkyl, heteroaryl, heteroaralkyl, alkenyl, alkynyl, —C(O)alkyl, —C(O)aryl, —C(O)aralkyl, —C(O)heteroaryl, —C(O)heteroaralkyl, —C(O)O(alkyl), —C(O)O(aryl), —C(O)O(aralkyl), —C(O)O(heteroaryl), —C(O)O(heteroaralkyl), —S(O)$_2$(aryl), —S(O)$_2$(alkyl), —S(O)$_2$(haloalkyl), —OR$^{14}$, —SR$^{14}$, or —NR$^{14}$R$^{15}$;

$R^2$ and $R^3$ each independently represent hydrogen or substituted or unsubstituted alkyl, aralkyl, aryl, heteroaralkyl, heteroaryl, (cycloalkyl)alkyl, cycloalkyl, (heterocycloalkyl)alkyl, heterocycloalkyl, alkenyl, alkynyl, alkylamino, hydroxyalkyl, alkoxyalkyl, aminoalkyl, or thioalkyl;

or wherein $R^{1a}$ and $R^2$ are taken together with the intervening atoms to form an optionally substituted heterocyclic ring;

$R^8$, $R^9$, $R^{10}$, and $R^{11}$ are independently selected for each occurrence from hydrogen, hydroxyl, halogen, nitro, alkyl, alkenyl, alkynyl, cyano, carboxyl, sulfate, amino, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, acyl, acyloxy, acylamino, aryl, heteroaryl, cycloalkyl, heterocycloalkyl, aralkyl, arylalkoxy, heteroaralkyl, (cycloalkyl)alkyl, and (heterocycloalkyl) alkyl;

$W^1$ and $W^2$ are each independently selected from alkyl, alkenyl, alkynyl, OR$^{12}$, SR$^{12}$, or NR$^{12}$R$^{13}$; or $W^1$ and $W^2$, taken together with the intervening atoms, form an optionally substituted heterocycloalkyl, cycloalkyl, heterocycloalkenyl, or cycloalkenyl group;

$R^{12}$ and $R^{13}$ are independently selected for each occurrence from hydrogen or substituted or unsubstituted alkyl, aralkyl, aryl, heteroaralkyl, heteroaryl, (cycloalkyl)alkyl, cycloalkyl, (heterocycloalkyl)alkyl, heterocycloalkyl, alkenyl, alkynyl, hydroxyalkyl, alkoxyalkyl, aminoalkyl, and thioalkyl; and $R^{14}$ and $R^{15}$ are independently selected for each occurrence from hydrogen or substituted or unsubstituted alkyl, aralkyl, aryl, heteroaralkyl, heteroaryl, (cycloalkyl)alkyl, cycloalkyl, (heterocycloalkyl)alkyl, heterocycloalkyl, alkenyl, and alkynyl.

In certain embodiments, $W^1$ and $W^2$, taken together with the intervening atoms, form an optionally substituted heterocycloalkyl, cycloalkyl, heterocycloalkenyl, or cycloalkenyl group.

In certain embodiments, the compound of formula (I) is represented by formula (Ia),

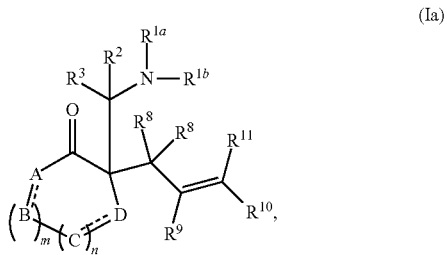

(Ia)

wherein:

A, B, C, and D each independently represent, as valence permits, NR', CR"R'", C(O), O, S, CR", or N; provided that no two adjacent occurrences of A, B, C, and D are NR', O, S, or N;

R' represents hydrogen or optionally substituted alkyl, cycloalkyl, (cycloalkyl)alkyl, aryl, aralkyl, heteroaryl, heteroaralkyl, alkenyl, alkynyl, —C(O)alkyl, —C(O)aryl, —C(O)aralkyl, —C(O)heteroaryl, —C(O)heteroaralkyl, —C(O)O(alkyl), —C(O)O(aryl), —C(O)O(aralkyl), —C(O)O(heteroaryl), —C(O)O(heteroaralkyl), —S(O)$_2$(aryl), —S(O)$_2$(alkyl), —S(O)$_2$(haloalkyl), —OR$^{14}$, —SR$^{14}$, or —NR$^{14}$R$^{15}$;

R" and R'" each independently represent hydrogen, hydroxyl, halogen, nitro, alkyl, cycloalkyl, (cycloalkyl)alkyl, aryl, aralkyl, heteroaryl, heteroaralkyl, (heterocycloalkyl)alkyl, heterocycloalkyl, alkenyl, alkynyl, cyano, carboxyl, sulfate, amino, alkoxy, aryloxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, acyl, acyloxy, or acylamino;

or any two occurrences of R', R", and R'" on adjacent A, B, C, or D groups, taken together with the intervening atoms, form an optionally substituted aryl, heteroaryl, cycloalkyl, cycloalkenyl, heterocycloalkyl, or heterocycloalkenyl group;

each occurrence of === independently represents a double bond or a single bond as permitted by valence; and m and n are integers each independently selected from 0, 1, and 2.

In certain embodiments, the sum of m and n is 0, 1, 2, or 3.

In certain embodiments, each occurrence of A, B, C, and D is each independently CR"R'" or CR".

In certain embodiments, each occurrence of A, B, C, and D is CR"R'".

In certain such embodiments, R" and R'" are each independently selected for each occurrence from hydrogen, hydroxyl, halogen, alkyl, cycloalkyl, (cycloalkyl)alkyl, aryl, aralkyl, heteroaryl, heteroaralkyl, (heterocycloalkyl)alkyl, heterocycloalkyl, alkenyl, alkynyl, amino, alkoxy, aryloxy, and alkylamino.

In certain preferred embodiments, each occurrence of A, B, C, and D is CH$_2$.

In certain embodiments, at least two adjacent occurrences of A, B, C, and D are CR". In accordance with valence requirements, there exists a double bond between the two adjacent occurrences of CR".

In certain embodiments, A and B are each CR" and m is 1. In such embodiments, there exists a double bond between A and B.

In certain such embodiments, R" is independently selected for each occurrence from hydrogen, hydroxyl, halogen, alkyl, cycloalkyl, (cycloalkyl)alkyl, aryl, aralkyl, heteroaryl, heteroaralkyl, (heterocycloalkyl)alkyl, heterocycloalkyl, alkenyl, alkynyl, amino, alkoxy, aryloxy, and alkylamino.

In alternative embodiments, the occurrence of R" on A and the occurrence of R" on B are taken together to form an optionally substituted aryl, heteroaryl, cycloalkenyl, or heterocycloalkenyl group. In certain preferred embodiments, the occurrence of R" on A and the occurrence of R" on B are taken together to form an optionally substituted aryl or heteroaryl group.

In certain embodiments, at least one occurrence of A, B, C, and D is NR'.

In certain such embodiments, at least one occurrence of the remaining A, B, C, and D is NR' or O.

In certain such embodiments, R' represents independently for each occurrence hydrogen or optionally substituted alkyl, aralkyl, heteroaralkyl, —C(O)alkyl, —C(O)aryl, —C(O)aralkyl, —C(O)O(alkyl), —C(O)O(aryl), —C(O)O(aralkyl), or —S(O)$_2$(aryl).

For embodiments of the compound of formula (Ia) having two or more A, B, C, or D groups, no two adjacent A groups, B groups, C groups, or D groups are NR', O, S, or N.

In certain embodiments, $R^8$, $R^9$, $R^{10}$, and $R^{11}$ are each independently selected for each occurrence from hydrogen, halogen, cyano, alkyl, alkoxy, alkylthio, aryl, aralkyl, alkenyl, alkynyl, heteroaryl, and heteroaralkyl.

In certain embodiments, $R^8$, $R^9$, $R^{10}$, and $R^{11}$ are each independently selected for each occurrence from hydrogen, alkyl, aryl, aralkyl, alkenyl, alkynyl, heteroaryl, and heteroaralkyl.

In certain embodiments, $R^8$, $R^9$, $R^{10}$, and $R^{11}$ are each hydrogen.

In certain embodiments, $R^2$ and $R^3$ are each independently selected from hydrogen and alkyl.

In certain embodiments, $R^2$ and $R^3$ are each hydrogen.

In certain embodiments, $R^{1a}$ represents hydrogen or optionally substituted alkyl, aralkyl, heteroaralkyl, —C(O)alkyl, —C(O)aryl, —C(O)aralkyl, —C(O)O(alkyl), —C(O)O(aryl), —C(O)O(aralkyl), or —S(O)$_2$(aryl). In certain such embodiments, $R^{1b}$ is H.

In certain preferred embodiments, $R^{1a}$ represents hydrogen or optionally substituted alkyl, —C(O)alkyl, —C(O)aryl, —C(O)aralkyl, —C(O)O(alkyl), —C(O)O(aryl), —C(O)O(aralkyl), or —S(O)$_2$(aryl). In certain such embodiments, $R^{1b}$ is H.

In some embodiments, $R^{1a}$ and $R^{1b}$ both are H.

In certain preferred embodiments, the compound of formula (I) or (Ia) is enantioenriched.

In certain embodiments, the compound of formula (I) or (Ia) has more than one stereogenic center. An exemplary compound having more than one stereogenic center may occur when $R^{1a}$ and $R^2$ are taken together with the intervening atoms to form an optionally substituted heterocyclic ring. In certain such embodiments, the compound of formula (I) or (Ia) is enantioenriched, diastereoenriched, or both.

In certain embodiments, the invention relates to a compound of formula (II),

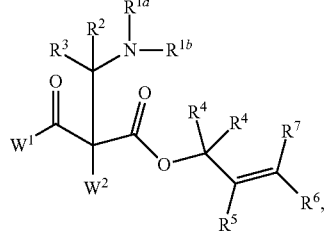

(II)

or a salt thereof;
wherein:
$R^{1a}$ and $R^{1b}$ each independently represent hydrogen or optionally substituted alkyl, cycloalkyl, (cycloalkyl)alkyl, aryl, aralkyl, heteroaryl, heteroaralkyl, alkenyl, alkynyl, —C(O)alkyl, —C(O)aryl, —C(O)aralkyl, —C(O)heteroaryl, —C(O)heteroaralkyl, —C(O)O(alkyl), —C(O)O(aryl), —C(O)O(aralkyl), —C(O)O(heteroaryl), —C(O)O(heteroaralkyl), —S(O)₂(aryl), —S(O)₂(alkyl), —S(O)₂(haloalkyl), —$OR^{14}$, —$SR^{14}$, or —$NR^{14}R^{15}$;
$R^2$ and $R^3$ each independently represent hydrogen or substituted or unsubstituted alkyl, aralkyl, aryl, heteroaralkyl, heteroaryl, (cycloalkyl)alkyl, cycloalkyl, (heterocycloalkyl)alkyl, heterocycloalkyl, alkenyl, alkynyl, alkylamino, hydroxyalkyl, alkoxyalkyl, aminoalkyl, or thioalkyl;
or wherein $R^{1a}$ and $R^2$ are taken together with the intervening atoms to form an optionally substituted heterocyclic ring;
$R^4$, $R^5$, $R^6$, and $R^7$ are independently selected for each occurrence from hydrogen, hydroxyl, halogen, nitro, alkyl, alkenyl, alkynyl, cyano, carboxyl, sulfate, amino, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, acyl, acyloxy, acylamino, aryl, heteroaryl, cycloalkyl, heterocycloalkyl, aralkyl, arylalkoxy, heteroaralkyl, (cycloalkyl)alkyl, and (heterocycloalkyl)alkyl;
$W^1$ and $W^2$ are each independently selected from alkyl, alkenyl, alkynyl, $OR^{12}$, $SR^{12}$, or $NR^{12}R^{13}$; or $W^1$ and $W^2$, taken together with the intervening atoms, form an optionally substituted heterocycloalkyl, cycloalkyl, heterocycloalkenyl, or cycloalkenyl group;
$R^{12}$ and $R^{13}$ are independently selected for each occurrence from hydrogen or substituted or unsubstituted alkyl, aralkyl, aryl, heteroaralkyl, heteroaryl, (cycloalkyl)alkyl, cycloalkyl, (heterocycloalkyl)alkyl, heterocycloalkyl, alkenyl, alkynyl, hydroxyalkyl, alkoxyalkyl, aminoalkyl, and thioalkyl; and
$R^{14}$ and $R^{15}$ are independently selected for each occurrence from hydrogen or substituted or unsubstituted alkyl, aralkyl, aryl, heteroaralkyl, heteroaryl, (cycloalkyl)alkyl, cycloalkyl, (heterocycloalkyl)alkyl, heterocycloalkyl, alkenyl, and alkynyl.

In certain embodiments, the compound of formula (II) is represented by formula (IIa),

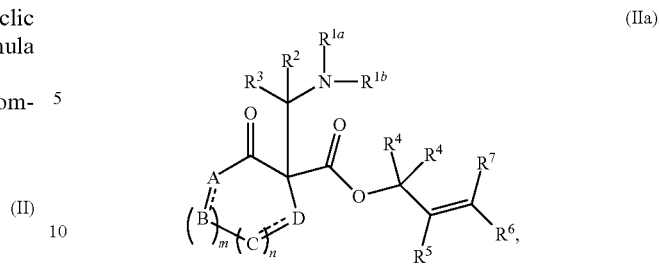

(IIa)

wherein:
A, B, C, and D each independently represent, as valence permits, NR', CR"R''', C(O), O, S, CR", or N; provided that no two adjacent occurrences of A, B, C, and D are NR', O, S, or N;
R' represents hydrogen or optionally substituted alkyl, cycloalkyl, (cycloalkyl)alkyl, aryl, aralkyl, heteroaryl, heteroaralkyl, alkenyl, alkynyl, —C(O)alkyl, —C(O)aryl, —C(O)aralkyl, —C(O)heteroaryl, —C(O)heteroaralkyl, —C(O)O(alkyl), —C(O)O(aryl), —C(O)O(aralkyl), —C(O)O(heteroaryl), —C(O)O(heteroaralkyl), —S(O)₂(aryl), —S(O)₂(alkyl), —S(O)₂(haloalkyl), —$OR^{14}$, —$SR^{14}$, or —$NR^{14}R^{15}$;
R" and R''' each independently represent hydrogen, hydroxyl, halogen, nitro, alkyl, cycloalkyl, (cycloalkyl)alkyl, aryl, aralkyl, heteroaryl, heteroaralkyl, (heterocycloalkyl)alkyl, heterocycloalkyl, alkenyl, alkynyl, cyano, carboxyl, sulfate, amino, alkoxy, aryloxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, acyl, acyloxy, or acylamino;
or any two occurrences of R', R", and R''' on adjacent A, B, C, or D groups, taken together with the intervening atoms, form an optionally substituted aryl, heteroaryl, cycloalkyl, cycloalkenyl, heterocycloalkyl, or heterocycloalkenyl group;
each occurrence of ═══ independently represents a double bond or a single bond as permitted by valence; and
m and n are integers each independently selected from 0, 1, and 2.

In certain embodiments, the sum of m and n is 0, 1, 2, or 3.

In certain embodiments, each occurrence of A, B, C, and D is each independently CR"R''' or CR".

In certain embodiments, each occurrence of A, B, C, and D is CR"R'''.

In certain such embodiments, R" and R''' are each independently selected for each occurrence from hydrogen, hydroxyl, halogen, alkyl, cycloalkyl, (cycloalkyl)alkyl, aryl, aralkyl, heteroaryl, heteroaralkyl, (heterocycloalkyl)alkyl, heterocycloalkyl, alkenyl, alkynyl, amino, alkoxy, aryloxy, and alkylamino.

In certain preferred embodiments, each occurrence of A, B, C, and D is $CH_2$.

In certain embodiments, at least two adjacent occurrences of A, B, C, and D are CR". In accordance with valence requirements, there exists a double bond between the two adjacent occurrences of CR".

In certain embodiments, A and B are each CR" and m is 1. In such embodiments, there exists a double bond between A and B.

In such embodiments, R" is independently selected for each occurrence from hydrogen, hydroxyl, halogen, alkyl, cycloalkyl, (cycloalkyl)alkyl, aryl, aralkyl, heteroaryl, heteroaralkyl, (heterocycloalkyl)alkyl, heterocycloalkyl, alkenyl, alkynyl, amino, alkoxy, aryloxy, and alkylamino.

In alternative embodiments, the occurrence of R" on A and the occurrence of R" on B are taken together to form an optionally substituted aryl, heteroaryl, cycloalkenyl, or heterocycloalkenyl group. In certain preferred embodiments, the occurrence of R" on A and the occurrence of R" on B are taken together to form an optionally substituted aryl or heteroaryl group.

In certain embodiments, at least one occurrence of A, B, C, and D is NR'.

In certain such embodiments, at least one occurrence of the remaining A, B, C, and D is NR' or O.

In certain such embodiments, R' represents independently for each occurrence hydrogen or optionally substituted alkyl, aralkyl, heteroaralkyl, —C(O)alkyl, —C(O)aryl, —C(O)aralkyl, —C(O)O(alkyl), —C(O)O(aryl), —C(O)O(aralkyl), or —S(O)$_2$(aryl).

For embodiments of the compound of formula (IIa) having two or more A, B, C, or D groups, no two adjacent A groups, B groups, C groups, or D groups are NR', O, S, or N.

In certain embodiments, $R^4$, $R^5$, $R^6$, and $R^7$ are each independently selected for each occurrence from hydrogen, halogen, cyano, alkyl, alkoxy, alkylthio, aryl, aralkyl, alkenyl, alkynyl, heteroaryl, and heteroaralkyl.

In certain embodiments, $R^4$, $R^5$, $R^6$, and $R^7$ are each independently selected for each occurrence from hydrogen, alkyl, aryl, aralkyl, alkenyl, alkynyl, heteroaryl, and heteroaralkyl.

In certain embodiments, $R^4$, $R^5$, $R^6$, and $R^7$ are each hydrogen.

In certain embodiments, $R^2$ and $R^3$ are each independently selected from hydrogen and alkyl.

In certain embodiments, $R^2$ and $R^3$ are each hydrogen.

In certain embodiments, $R^{1a}$ represents hydrogen or optionally substituted alkyl, aralkyl, heteroaralkyl, —C(O)alkyl, —C(O)aryl, —C(O)aralkyl, —C(O)O(alkyl), —C(O)O(aryl), —C(O)O(aralkyl), or —S(O)$_2$(aryl). In certain such embodiments, $R^{1b}$ is H.

In certain preferred embodiments, $R^{1a}$ represents hydrogen or optionally substituted alkyl, —C(O)alkyl, —C(O)aryl, —C(O)aralkyl, —C(O)O(alkyl), —C(O)O(aryl), —C(O)O(aralkyl), or —S(O)$_2$(aryl). In certain such embodiments, $R^{1b}$ is H.

In some embodiments, $R^{1a}$ and $R^{1b}$ both are H.

IV. Methods of the Invention

In certain embodiments, the invention provides methods for the preparation of a compound of formula (I):

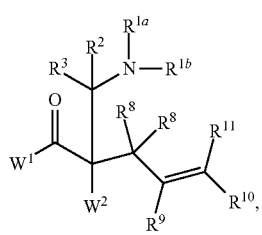

(I)

comprising treating a compound of formula (II):

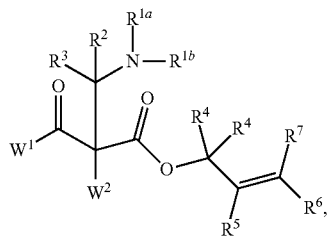

(II)

with a transition metal catalyst under alkylation conditions, wherein, as valence and stability permit, $R^{1a}$ and $R^{1b}$ each independently represent hydrogen or optionally substituted alkyl, cycloalkyl, (cycloalkyl)alkyl, aryl, aralkyl, heteroaryl, heteroaralkyl, alkenyl, alkynyl, —C(O)alkyl, —C(O)aryl, —C(O)aralkyl, —C(O)heteroaryl, —C(O)heteroaralkyl, —C(O)O(alkyl), —C(O)O(aryl), —C(O)O(aralkyl), —C(O)O(heteroaryl), —C(O)O(heteroaralkyl), —S(O)$_2$(aryl), —S(O)$_2$(alkyl), —S(O)$_2$(haloalkyl), —OR$^{14}$, —SR$^{14}$, or —NR$^{14}$R$^{15}$;

$R^2$ and $R^3$ each independently represent hydrogen or substituted or unsubstituted alkyl, aralkyl, aryl, heteroaralkyl, heteroaryl, (cycloalkyl)alkyl, cycloalkyl, (heterocycloalkyl)alkyl, heterocycloalkyl, alkenyl, alkynyl, alkylamino, hydroxyalkyl, alkoxyalkyl, aminoalkyl, or thioalkyl;

or wherein $R^{1a}$ and $R^2$ are taken together with the intervening atoms to form an optionally substituted heterocyclic ring;

$R^4$, $R^5$, $R^6$, $R^7$, $R^8$, $R^9$, $R^{10}$, and $R^{11}$ are each independently selected for each occurrence from hydrogen, hydroxyl, halogen, nitro, alkyl, alkenyl, alkynyl, cyano, carboxyl, sulfate, amino, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, acyl, acyloxy, acylamino, aryl, heteroaryl, cycloalkyl, heterocycloalkyl, aralkyl, arylalkoxy, heteroaralkyl, (cycloalkyl)alkyl, and (heterocycloalkyl)alkyl;

$W^1$ and $W^2$ are each independently selected from alkyl, alkenyl, alkynyl, OR$^{12}$, SR$^{12}$, or NR$^{12}$R$^{13}$; or $W^1$ and $W^2$, taken together with the intervening atoms, form an optionally substituted heterocycloalkyl, cycloalkyl, heterocycloalkenyl, or cycloalkenyl group;

$R^{12}$ and $R^{13}$ are independently selected for each occurrence from hydrogen or substituted or unsubstituted alkyl, aralkyl, aryl, heteroaralkyl, heteroaryl, (cycloalkyl)alkyl, cycloalkyl, (heterocycloalkyl)alkyl, heterocycloalkyl, alkenyl, alkynyl, hydroxyalkyl, alkoxyalkyl, aminoalkyl, and thioalkyl; and $R^{14}$ and $R^{15}$ are independently selected for each occurrence from hydrogen or substituted or unsubstituted alkyl, aralkyl, aryl, heteroaralkyl, heteroaryl, (cycloalkyl)alkyl, cycloalkyl, (heterocycloalkyl)alkyl, heterocycloalkyl, alkenyl, and alkynyl.

In certain embodiments, $W^1$ and $W^2$, taken together with the intervening atoms, form an optionally substituted heterocycloalkyl, cycloalkyl, heterocycloalkenyl, or cycloalkenyl group.

In certain embodiments, formula (I) is represented by formula (Ia),

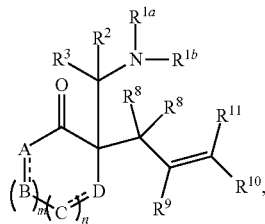

(Ia)

and formula (II) is represented by formula (IIa),

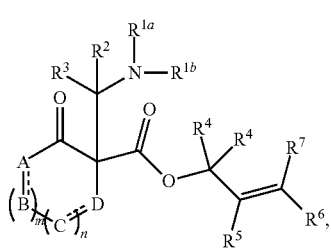

(IIa)

wherein:
A, B, C, and D each independently represent, as valence permits, NR', CR"R'", C(O), O, S, CR", or N; provided that no two adjacent occurrences of A, B, C, and D are NR', O, S, or N;
R' represents hydrogen or optionally substituted alkyl, cycloalkyl, (cycloalkyl)alkyl, aryl, aralkyl, heteroaryl, heteroaralkyl, alkenyl, alkynyl, —C(O)alkyl, —C(O)aryl, —C(O)aralkyl, —C(O)heteroaryl, —C(O)heteroaralkyl, —C(O)O(alkyl), —C(O)O(aryl), —C(O)O(aralkyl), —C(O)O(heteroaryl), —C(O)O(heteroaralkyl), —S(O)$_2$(aryl), —S(O)$_2$(alkyl), —S(O)$_2$(haloalkyl), —OR$^{14}$, —SR$^{14}$, or —NR$^{14}$R$^{15}$;
R" and R'" each independently represent hydrogen, hydroxyl, halogen, nitro, alkyl, cycloalkyl, (cycloalkyl)alkyl, aryl, aralkyl, heteroaryl, heteroaralkyl, (heterocycloalkyl)alkyl, heterocycloalkyl, alkenyl, alkynyl, cyano, carboxyl, sulfate, amino, alkoxy, aryloxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, acyl, acyloxy, or acylamino;
or any two occurrences of R', R", and R'" on adjacent A, B, C, or D groups, taken together with the intervening atoms, form an optionally substituted aryl, heteroaryl, cycloalkyl, cycloalkenyl, heterocycloalkyl, or heterocycloalkenyl group;
each occurrence of === independently represents a double bond or a single bond as permitted by valence; and
m and n are integers each independently selected from 0, 1, and 2.

In certain embodiments, the sum of m and n is 0, 1, 2, or 3.

In certain embodiments, each occurrence of A, B, C, and D is each independently CR"R'" or CR".

In certain embodiments, each occurrence of A, B, C, and D is CR"R'".

In certain such embodiments, R" and R'" are each independently selected for each occurrence from hydrogen, hydroxyl, halogen, alkyl, cycloalkyl, (cycloalkyl)alkyl, aryl, aralkyl, heteroaryl, heteroaralkyl, (heterocycloalkyl)alkyl, heterocycloalkyl, alkenyl, alkynyl, amino, alkoxy, aryloxy, and alkylamino.

In certain preferred embodiments, each occurrence of A, B, C, and D is CH$_2$.

In certain embodiments, at least two adjacent occurrences of A, B, C, and D are CR".

In certain embodiments, A and B are each CR" and m is 1.

In certain such embodiments, R" is independently selected for each occurrence from hydrogen, hydroxyl, halogen, alkyl, cycloalkyl, (cycloalkyl)alkyl, aryl, aralkyl, heteroaryl, heteroaralkyl, (heterocycloalkyl)alkyl, heterocycloalkyl, alkenyl, alkynyl, amino, alkoxy, aryloxy, and alkylamino.

In alternative embodiments, the occurrence of R" on A and the occurrence of R" on B are taken together to form an optionally substituted aryl, heteroaryl, cycloalkenyl, or heterocycloalkenyl group.

In certain embodiments, at least one occurrence of A, B, C, and D is NR'.

In certain such embodiments, at least one occurrence of the remaining A, B, C, and D is NR' or O.

In certain such embodiments, R' represents independently for each occurrence hydrogen or optionally substituted alkyl, aralkyl, heteroaralkyl, —C(O)alkyl, —C(O)aryl, —C(O)aralkyl, —C(O)O(alkyl), —C(O)O(aryl), —C(O)O(aralkyl), or —S(O)$_2$(aryl).

For embodiments of the compound of formula (Ia) or (IIa) having two or more A, B, C, or D groups, no two adjacent A groups, B groups, C groups, or D groups are NR', O, S, or N.

In certain embodiments, R$^4$, R$^5$, R$^6$, R$^7$, R$^8$, R$^9$, R$^{10}$, and R$^{11}$ are each independently selected for each occurrence from hydrogen, halogen, cyano, alkyl, alkoxy, alkylthio, aryl, aralkyl, alkenyl, alkynyl, heteroaryl, and heteroaralkyl.

In certain embodiments, R$^4$, R$^5$, R$^6$, R$^7$, R$^8$, R$^9$, R$^{10}$, and R$^{11}$ are each independently selected for each occurrence from hydrogen, alkyl, aryl, aralkyl, alkenyl, alkynyl, heteroaryl, and heteroaralkyl.

In certain embodiments, R$^4$, R$^5$, R$^6$, R$^7$, R$^8$, R$^9$, R$^{10}$, and R$^{11}$ are each hydrogen.

In certain embodiments, R$^2$ and R$^3$ are each independently selected from hydrogen and alkyl.

In certain embodiments, R$^2$ and R$^3$ are each hydrogen.

In certain embodiments, R$^{1a}$ represents hydrogen or optionally substituted alkyl, aralkyl, heteroaralkyl, —C(O) alkyl, —C(O)aryl, —C(O)aralkyl, —C(O)O(alkyl), —C(O)O(aryl), —C(O)O(aralkyl), or —S(O)$_2$(aryl). In certain such embodiments, R$^{1b}$ is H.

In certain preferred embodiments, R$^{1a}$ represents hydrogen or optionally substituted alkyl, —C(O)alkyl, —C(O) aryl, —C(O)aralkyl, —C(O)O(alkyl), —C(O)O(aryl), —C(O)O(aralkyl), or —S(O)$_2$(aryl). In certain such embodiments, R$^{1b}$ is H.

In some embodiments, R$^{1a}$ and R$^{1b}$ both are H.

In certain preferred embodiments of the methods described herein, the compound of formula (I) generated by the methods is enantioenriched.

In certain embodiments of the methods, the compound of formula (I) generated by the methods of the invention has more than one stereogenic center. In certain such embodiments, the compound of formula (I) is enantioenriched, diastereoenriched, or both.

In certain embodiments, the method further comprises contacting a compound of formula (III):

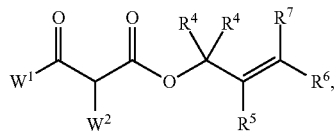

(III)

with an imine of formula (IV):

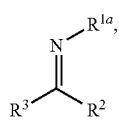

(IV)

under conditions sufficient to produce a compound of formula (II).

In certain embodiments, the step of contacting a compound of formula (III) with an imine of formula (IV) occurs under basic conditions.

In certain embodiments, the imine of formula (IV) is generated in situ. For example, the starting material can be a sulfonylmethyl carbamate, which eliminates a hydrogen sulfone under basic conditions, generating the imine in situ. Without being bound to theory, this basic environment can also promote the subsequent Mannich reaction.

In certain embodiments, the method of preparing a compound of formula (I) from the compound of formula (III) occurs in a two-step, two-pot synthetic procedure.

Alternatively, the method of preparing a compound of formula (I) from the compound of formula (III) occurs in a one-pot synthetic procedure that begins with (i) a Mannich reaction followed by (ii) a decarboxylative allylic alkylation reaction.

Transition Metal Catalysts

Preferred transition metal catalysts of the invention are complexes of transition metals wherein the metal is selected from Groups 6, 8, 9 and 10 in the periodic table. In preferred embodiments, the metal of the transition metal catalyst is selected from molybdenum, tungsten, iridium, rhenium, ruthenium, nickel, platinum, and palladium. In more preferred embodiments, the transition metal catalyst comprises a transition metal selected from palladium, nickel, and platinum, most preferably palladium.

In certain embodiments of the invention, the transition metal complex utilized in the reaction includes a transition metal that has a low oxidation state, typically (O) or (I). A low oxidation state enables the metal to undergo oxidative addition to the substrate. It should be appreciated that the air- and moisture-sensitivity of many such complexes of transition metals will necessitate appropriate handling precautions. This may include the following precautions without limitation: minimizing exposure of the reactants to air and water prior to reaction; maintaining an inert atmosphere within the reaction vessel; properly purifying all reagents; and removing water from reaction vessels prior to use.

Exemplary transition metal catalysts include, without limitation, $Mo(CO)_6$, $Mo(MeCN)_3(CO)_3$, $W(CO)_6$, $W(MeCN)_3(CO)_3$, $[Ir(1,5-cyclooctadiene)Cl]_2$, $[Ir(1,5-cyclooctadiene)Cl]_2$, $[Ir(1,5-cyclooctadiene)Cl]_2$, $Rh(PPh_3)_3Cl$, $[Rh(1,5-cyclooctadiene)Cl]_2$, Ru(pentamethylcyclopentadienyl)(MeCN)_3PF_6$, $Ni(1,5-cyclooctadiene)_2$, $Ni[P(OEt)_3]_4$, tris(dibenzylideneacetone)dipalladium(O), tris(dibenzylideneacetone)dipalladium(O)-chloroform adduct, tris(bis(4-methoxybenzylidene)acetone)dipalladium (O), $Pd(OC(=O)CH_3)_2$ [$Pd(OAc)_2$], Pd(3,5-dimethyloxy-dibenzylideneacetone)$_2$, $PdCl_2(R^{23}CN)_2$; $PdCl_2(PR^{24}R^{25}R^{26})_2$, $[Pd(\eta^3\text{-allyl})Cl]_2$; and $Pd(PR^{24}R^{25}R^{26})_4$, wherein $R^{23}$, $R^{24}$, $R^{25}$, and $R^{26}$ are independently selected from hydrocarbyl, substituted hydrocarbyl, heteroatom-containing hydrocarbyl, and substituted heteroatom-containing hydrocarbyl. In particular embodiments, the transition metal catalyst tris(dibenzylideneacetone)dipalladium, $Pd_2(dba)_3$, or tris(bis(4-methoxybenzylidene)acetone) dipalladium, $Pd_2(pmdba)_3$, is preferred.

To improve the effectiveness of the catalysts discussed herein, additional reagents may be employed as needed, including, without limitation, salts, solvents, and other small molecules. Preferred additives include $AgBF_4$, $AgOSO_2CF_3$, $AgOC(=O)CH_3$, and bipyridine. These additives are preferably used in an amount that is in the range of about 1 equivalent to about 5 equivalents relative to the amount of the catalyst.

A low oxidation state of a transition metal, i.e., an oxidation state sufficiently low to undergo oxidative addition, can also be obtained in situ, by the reduction of transition metal complexes that have a high oxidation state. Reduction of the transition metal complex can be achieved by adding nucleophilic reagents including, without limitation, $NBu_4OH$, tetrabutylammonium difluorotriphenylsilicate (TBAT), tetrabutylammonium fluoride (TBAF), 4-dimethylaminopyridine (DMAP), $NMe_4OH(H_2O)_5$, KOH/1,4,7,10,13,16-hexaoxacyclooctadecane, EtONa, TBAT/trimethyl-(2-methyl-cyclohex-1-enyloxy)-silane, and mixtures thereof. When a nucleophilic reagent is needed for the reduction of the metal complex, the nucleophilic reagent is used in an amount in the range of about 1 mol % to about 20 mol % relative to the reactant, more preferably in the range of about 1 mol % to about 10 mol % relative to the substrate, and most preferably in the range of about 5 mol % to about 8 mol % relative to the substrate.

In certain embodiments, a Pd(II) complex can be reduced in situ to form a Pd(O) catalyst. Exemplary transition metal complexes that may be reduced in situ, include, without limitation, allylchloro[1,3-bis(2,6-di-i-propylphenyl)imidazol-2-ylidene]palladium(II), ([2S,3S]-bis[diphenylphosphino]butane)($\eta^3$-allyl)palladium(II) perchlorate, [S]-4-tert-butyl-2-(2-diphenylphosphanyl-phenyl)-4,5-dihydro-oxazole($\eta^3$-allyl)palladium(II) hexafluorophosphate (i.e., [Pd(S-tBu-PHOX)(allyl)]$PF_6$), and cyclopentadienyl($\eta^3$-allyl) palladium(II), with [Pd(s-tBu-PHOX)(allyl)]$PF_6$ and cyclopentadienyl($\eta^3$-allyl)palladium(II) being most preferred.

In certain embodiments, the transition metal is palladium. In certain embodiments, the transition metal catalyst is a dimer of a transition metal. Exemplary dimeric transition metal catalysts include $Pd_2(dba)_3$ and $Pd_2(pmdba)_3$. In certain preferred embodiments, the transition metal catalyst is $Pd_2(dba)_3$ or $Pd_2(pmdba)_3$. In embodiments of the method wherein the transition metal catalyst is a dimer, the amount of total transition metal present in the reaction is twice the amount of the transition metal catalytic complex.

Accordingly, when describing the amount of transition metal catalyst used in the methods of the invention, the following terminology applies. The amount of transition metal catalyst present in a reaction is alternatively referred to herein as "catalyst loading". Catalyst loading may be expressed as a percentage that is calculated by dividing the moles of catalyst complex by the moles of the substrate present in a given reaction. Catalyst loading is alternatively expressed as a percentage that is calculated by dividing the moles of total transition metal (for example, palladium) by the moles of the substrate present in a given reaction. For example, in a reaction that uses 5 mol % dimeric catalyst (e.g, $Pd_2(dba)_3$), this amount of transition metal catalyst can be alternatively expressed as 10 mol % total transition metal (e.g., Pd(O)).

In certain embodiments, the transition metal catalyst is present under the conditions of the reaction from an amount of about 0.1 mol % to about 20 mol % total palladium relative to the substrate, which is the compound of formula (II) or (IIa). In certain embodiments, the catalyst loading is from about 1 mol % to about 15 mol % total palladium relative to the substrate. For example, in certain embodiments, the catalyst loading is about 1 mol %, about 2 mol %, about 3 mol %, about 5 mol %, about 6 mol %, about 8 mol %, about 9 mol %, about 10 mol %, about 11 mol %, about 12 mol %, or about 15 mol % total palladium.

Ligands

One aspect of the invention relates to the enantioselectivity of the methods. Enantioselectivity results from the use of chiral ligands during the allylic alkylation reaction. Accordingly, in certain embodiments, the transition metal catalyst further comprises a chiral ligand. Without being bound by theory, the asymmetric environment that is created around the metal center by the presence of chiral ligands produces an enantioselective reaction. The chiral ligand forms a complex with the transition metal, thereby occupying one or more of the coordination sites on the metal and creating an asymmetric environment around the metal center. This complexation may or may not involve the displacement of achiral ligands already complexed to the metal. When displacement of one or more achiral ligands occurs, the displacement may proceed in a concerted fashion, i.e., with both the achiral ligand decomplexing from the metal and the chiral ligand complexing to the metal in a single step. Alternatively, the displacement may proceed in a stepwise fashion, i.e., with decomplexing of the achiral ligand and complexing of the chiral ligand occurring in distinct steps. Complexation of the chiral ligand to the transition metal may be allowed to occur in situ, i.e., by admixing the ligand and metal before adding the substrate. Alternatively, the ligand-metal complex can be formed separately, and the complex isolated before use in the alkylation reactions of the present invention.

Once coordinated to the transition metal center, the chiral ligand influences the orientation of other molecules as they interact with the transition metal catalyst. Coordination of the metal center with a π-allyl group and reaction of the substrate with the π-allyl-metal complex are dictated by the presence of the chiral ligand. The orientation of the reacting species determines the stereochemistry of the products.

Chiral ligands of the invention may be bidentate or monodentate or, alternatively, ligands with higher denticity (e.g., tridentate, tetradentate, etc.) can be used. Preferably, the ligand will be substantially enantiopure. By "enantiopure" is meant that only a single enantiomer is present. In many cases, substantially enantiopure ligands can be purchased from commercial sources, obtained by successive recrystallizations of an enantioenriched substance, or by other suitable means for separating enantiomers.

Exemplary chiral ligands may be found in U.S. Pat. No. 7,235,698, the entirely of which is incorporated herein by reference. In certain embodiments, the chiral ligand is an enantioenriched phosphine ligand. In certain embodiments, the enantioenriched phosphine ligand is a P,N-ligand such as a phosphinooxazoline (PHOX) ligand. Preferred chiral ligands of the invention include the PHOX-type chiral ligands such as (R)-2-[2-(diphenylphosphino)phenyl]-4-iso-propyl-2-oxazoline, (R)-2-[2-(diphenylphosphino)phenyl]-4-phenyl-2-oxazoline, (S)-2-[2-(diphenylphosphino)phenyl]-4-benzyl-2-oxazoline, (S)-2-[2-(diphenylphosphino)phenyl]-4-tert-butyl-2-oxazoline ((S)-t-BuPHOX) and (S)-2-(2-(bis(4-(Trifluoromethyl)phenyl)phosphino)-5-(trifluoromethyl)phenyl)-4-(tert-butyl)-4,5-dihydrooxazole ((S)—$(CF_3)_3$-t-BuPHOX). In preferred embodiments, the PHOX type chiral ligand is selected from (S)-t-BuPHOX and (S)—$(CF_3)_3$-t-BuPHOX). The ligand structures are depicted below.

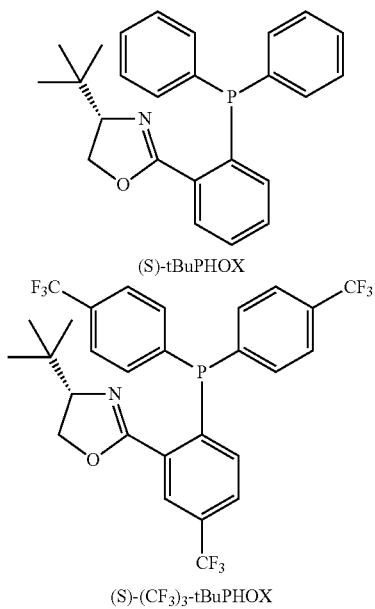

(S)-tBuPHOX (S)-$(CF_3)_3$-tBuPHOX

Generally, the chiral ligand is present in an amount in the range of about 0.75 equivalents to about 10 equivalents relative to the amount of total metal from the catalyst, preferably in the range of about 0.75 to about 5 equivalents relative to the amount of total metal from the catalyst, and most preferably in the range of about 0.75 to about 1.25, such as about 1.25 equivalents relative to the amount of total metal from the catalyst. Alternatively, the amount of the chiral ligand can be measured relative to the amount of the substrate.

In certain embodiments, the ligand is present under the conditions of the reaction from an amount of about 0.5 mol % to about 30 mol % relative to the substrate, which is the compound of formula (II) or (IIa). The amount of ligand present in the reaction is alternatively referred to herein as "ligand loading" and is expressed as a percentage that is calculated by dividing the moles of ligand by the moles of the substrate present in a given reaction. In certain embodiments, the ligand loading is from about 5 mol % to about 15 mol %. For example, in certain embodiments, the ligand loading is about 5 mol %, about 6 mol %, about 7.5 mol %, about 9 mol %, about 10 mol %, about 11 mol %, about 12 mol %, about 12.5 mol %, about 13 mol %, about 14 mol %, or about 15 mol %. In certain embodiments, the ligand is in excess of the transition metal catalyst. In certain embodiments, the ligand loading is about 1.25 times the transition metal catalyst loading. In embodiments in which the transition metal catalyst is a dimer, the ligand loading is about 2.5 times the loading of the dimeric transition metal catalyst.

Where a chiral ligand is used, the reactions of the invention may enrich the stereocenter a to the carbonyl (i.e., bearing $C(R^2)(R^3)NH(R^1)$) in the product relative to the enrichment at this center, if any, of the starting material. In certain embodiments, the chiral ligand used in the methods of the invention yields a compound of formula (I) or (Ia) that is enantioenriched. The level of enantioenrichment of a compound may be expressed as enantiomeric excess (ee). The ee of a compound may be measured by dividing the difference in the fractions of the enantiomers by the sum of the fractions of the enantiomers. For example, if a compound is found to comprise 98% (S)-enantiomer, and 2% (R) enantiomer, then the ee of the compound is (98−2)/(98+2), or 96%. In certain embodiments, the compound of formula (I) or (Ia) has about 30% ee or greater, 40% ee or greater, 50% ee or greater, 60% ee or greater, 70% ee or greater, about 80% ee, about 85% ee, about 88% ee, about 90% ee, about 91% ee, about 92% ee, about 93% ee, about 94% ee, about 95% ee, about 96% ee, about 97% ee, about 98% ee, about 99% ee, or above about 99% ee, even where this % ee is greater than the % ee of the starting material, such as 0% ee (racemic). In certain embodiments, the compound of formula (I) or (Ia) is enantioenriched. In certain embodiments, the compound of formula (I) or (Ia) is enantiopure. In embodiments where the starting material has more than one stereocenter, reactions of the invention may enrich the stereocenter a to the carbonyl relative to the enrichment at this center, if any, of the starting material, and substantially independently of the stereochemical disposition/enrichment of any other stereocenters of the molecule. For example, a product of the methods described herein may have 30% de or greater, 40% de or greater, 50% de or greater, 60% de or greater, 70% de or greater, 80% de or greater, 90% de or greater, 95% de or greater, or even 98% de or greater at the stereocenter a to the carbonyl.

In certain embodiments, the invention also relates to methods that utilize an achiral ligand. Exemplary achiral ligands include triphenylphosphine, tricyclohexylphosphine, tri-(ortho-tolyl)phosphine, trimethylphosphite, and triphenylphosphite.

Alkylation Conditions

In certain embodiments, the methods of the invention include treating a compound of formula (II) or (IIa) with a transition metal catalyst under alkylation conditions. In certain embodiments, alkylation conditions of the reaction include one or more organic solvents. In certain embodiments, organic solvents include aromatic or non-aromatic hydrocarbons, ethers, alkylacetates, nitriles, or combinations thereof. In certain embodiments, organic solvents include hexane, pentane, benzene, toluene, xylene, cyclic ethers such as optionally substituted tetrahydrofuran and dioxane, acyclic ethers such as dimethoxyethane, diethyl ether, methyl tertbutyl ether, and cyclopentyl methyl ether, acetonitrile, isobutyl acetate, ethyl acetate, isopropyl acetate, or combinations thereof. In certain preferred embodiments, the solvent is toluene, methyl tertbutyl ether, cyclopentyl methyl ether, 2-methyltetrahydrofuran, isobutyl acetate, ethyl acetate, or isopropyl acetate. In certain other preferred embodiments, the solvent is toluene.

In certain embodiments, alkylation conditions of the reaction include a reaction temperature. In certain embodiments, the reaction temperature is ambient temperature (about 20° C. to about 26° C.). In certain embodiments, the reaction temperature is higher than ambient temperature, such as, for example, about 30° C., about 35° C., about 40° C., about 45° C., about 50° C., about 55° C., or about 60° C. In certain embodiments, the reaction temperature is lower than ambient temperature, such as, for example, about 0° C.

EXEMPLIFICATION

The invention described generally herein will be more readily understood by reference to the following examples, which are included merely for purposes of illustration of certain aspects and embodiments of the present invention, and are not intended to limit the invention.

Example 1. Representative Synthesis for Preparation of α-Aminomethyl 1,3-Dicarbonyl Substrate To introduce the aminomethyl moiety, sulfonylmethyl carbamates (e.g., 2a) were employed as versatile and readily available imine precursors. In the presence of $Cs_2CO_3$, the Boc-protected imine generated from 2 reacted with β-keto ester 1 to smoothly afford β-aminoketone 3a, quantitatively, at ambient temperature. In a similar manner, other protected aminoketones 3b-g were obtained in good to excellent yields.

Representative Procedure A

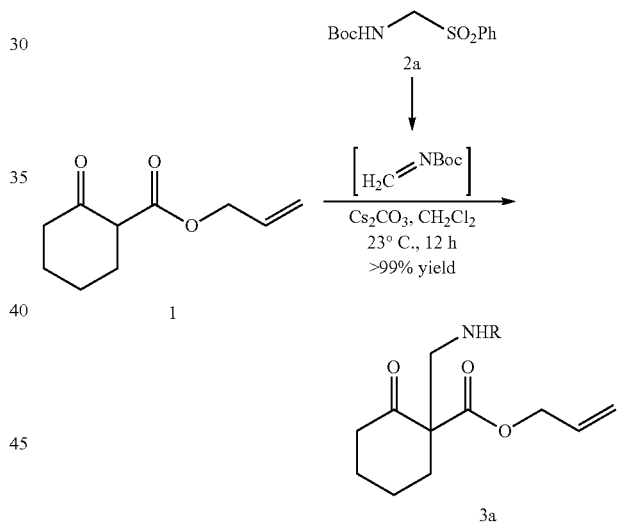

Allyl 1-(((tert-butoxycarbonyl)amino)methyl)-2-oxocyclohexane-1-carboxylate (3a)

To a stirred solution of β-keto ester 1 (0.91 g, 5.0 mmol, 1 equiv) in $CH_2Cl_2$ (25 mL) was added sulfonylmethyl carbamate 2a (1.63 g, 6.0 mmol, 1.2 equiv) in one portion at ambient temperature. After stirring for 5 min, $Cs_2CO_3$ (4.70 g, 12.5 mmol, 2.5 equiv) was added in one portion. After 12 h, full consumption of starting material was determined by TLC analysis. Saturated aqueous ammonium chloride was added slowly, and the biphasic mixture was stirred at ambient temperature for 20 min and extracted with $CH_2Cl_2$ (3×25 mL). The combined organic layers were dried over $Na_2SO_4$, filtered, and concentrated in vacuo. Flash column chromatography ($SiO_2$, 10% EtOAc in hexanes) afforded α-aminomethyl β-keto ester 3a (1.55 g, 99% yield) as a faintly yellow oil. $R_f$=0.55 (25% EtOAc in hexanes); $^1$H NMR (500

MHz, CDCl$_3$) δ 5.91 (ddt, J=16.5, 10.4, 5.8 Hz, 1H), 5.33 (m, 1H), 5.25 (m, 1H), 5.17 (m, 1H), 4.63 (m, 2H), 3.54 (dd, J=13.9, 7.7 Hz, 1H), 3.40 (dd, J=13.9, 5.7 Hz, 1H), 2.59-2.41 (m, 3H), 1.99 (m, 1H), 1.81 (m, 1H), 1.73-1.51 (m, 3H), 1.40 (s, 9H); $^{13}$C NMR (126 MHz, CDCl$_3$) δ 209.0, 171.0, 156.0, 131.6, 119.2, 79.4, 66.4, 62.4, 44.4, 40.9, 33.9, 28.5, 27.3, 22.2; IR (Neat Film, NaCl) 3461, 3404, 2976, 2939, 2867, 1713, 1501, 1452, 1366, 1247, 1229, 1168, 1141 cm$^{-1}$; HRMS (FAB+) m/z calc'd for C$_{16}$H$_{26}$NO$_5$ [M+H]$^+$: 312.1811. found 312.1824.

Allyl 1-(benzyloxycarbonylaminomethyl)-2-oxocyclohexane-1-carboxylate (3b)

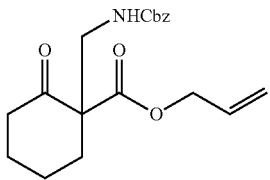 [SMILES: C=CCOC(=O)C1(CNC(=O)OCc2ccccc2)CCCCC1=O]

The reaction was conducted according to representative procedure A. Keto ester 1 (1.66 g, 9.09 mmol); sulfonylmethyl carbamate 2b (3.33 g, 10.9 mmol); Cs$_2$CO$_3$ (7.40 g, 22.7 mmol). The reaction mixture was stirred for 18 h. Flash column chromatography (SiO$_2$, 15% EtOAc in hexanes) afforded α-aminomethyl β-keto ester 3b (2.95 g, 8.54 mmol, 94% yield) as a colorless oil. R$_f$=0.27 (20% EtOAc in hexanes); $^1$H NMR (500 MHz, CDCl$_3$) δ 7.38-7.28 (m, 5H), 5.86 (ddt, J=16.6, 10.5, 5.9 Hz, 1H), 5.41 (m, 1H), 5.32 (m, 1H), 5.23 (m, 1H), 5.11-5.01 (m, 2H), 4.63-4.52 (m, 2H), 3.62 (dd, J=13.8, 7.7 Hz, 1H), 3.46 (dd, J=13.8, 5.6 Hz, 1H), 2.59-2.42 (m, 3H), 2.00 (m, 1H), 1.81 (m, 1H), 1.72-1.53 (m, 3H); $^{13}$C NMR (126 MHz, CDCl$_3$) δ 208.8, 170.7, 156.5, 136.6, 131.5, 128.6, 128.2, 128.1, 119.3, 66.8, 66.4, 62.2, 44.8, 40.9, 33.9, 27.2, 22.1; IR (Neat Film, NaCl) 3450, 3394, 2943, 1724, 1711, 1509, 1453, 1265 1219, 1141, 981 cm$^{-1}$; HRMS (ESI+) m/z calc'd for C$_{19}$H$_{24}$NO$_5$ [M+H]$^+$: 346.1649. found 346.1634.

Allyl 1-((4-methoxyphenoxy)carbonylaminomethyl)-2-oxocyclohexane-1-carboxylate (3c)

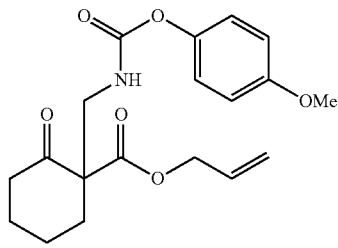 [SMILES: C=CCOC(=O)C1(CNC(=O)Oc2ccc(OC)cc2)CCCCC1=O]

The reaction was conducted according to representative procedure A. Keto ester 1 (182 mg, 1.00 mmol); sulfonylmethyl carbamate 2c (386 mg, 1.20 mmol); Cs$_2$CO$_3$ (910 mg, 2.50 mmol). The reaction mixture was stirred for 24 h. Flash column chromatography (SiO$_2$, 15% EtOAc in hexanes) afforded α-aminomethyl β-keto ester 3c (265 mg, 0.733 mmol, 73% yield) as a colorless oil. R$_f$=0.18 (20% EtOAc in hexanes); $^1$H NMR (500 MHz, CDCl$_3$) δ 7.01-6.97 (m, 2H), 6.88-6.82 (m, 2H), 5.91 (m, 1H), 5.67 (m, 1H), 5.34 (m, 1H), 5.26 (m, 1H), 4.67-4.64 (m, 2H), 3.78 (s, 3H), 3.67 (dd, J=13.9, 7.7 Hz, 1H), 3.53 (dd, J=13.9, 5.6 Hz, 1H), 2.62-2.46 (m, 3H), 2.03 (m, 1H), 1.84 (m, 1H), 1.76-1.58 (m, 3H); $^{13}$C NMR (126 MHz, CDCl$_3$) δ 208.9, 170.7, 157.0, 155.3, 144.7, 131.5, 122.4, 119.4, 114.4, 66.5, 62.2, 55.7, 45.0, 40.9, 34.0, 27.2, 22.1; IR (Neat Film, NaCl) 3377, 2943, 1742, 1732, 1709, 1498, 1201, 1055 cm$^{-1}$; HRMS (ESI+) m/z calc'd for C$_{19}$H$_{24}$NO$_6$ [M+H]$^+$: 362.1598. found 362.1601.

Allyl 1-(phenoxycarbonylaminomethyl)-2-oxocyclohexane-1-carboxylate (3d)

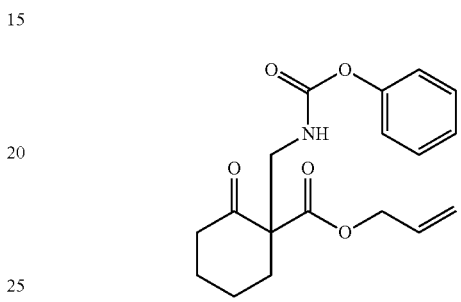

The reaction was conducted according to representative procedure A. Keto ester 1 (182 mg, 1.00 mmol); sulfonylmethyl carbamate 2d (350 mg, 1.20 mmol); Cs$_2$CO$_3$ (910 mg, 2.50 mmol). The reaction mixture was stirred for 24 h. Flash column chromatography (SiO$_2$, 15% EtOAc in hexanes) afforded α-aminomethyl β-keto ester 3d (310 mg, 0.936 mmol, 94% yield) as a colorless oil. R$_f$=0.25 (20% EtOAc in hexanes); $^1$H NMR (500 MHz, CDCl$_3$) δ 7.37-7.29 (m, 2H), 7.18 (m, 1H), 7.12-7.05 (m, 2H), 5.92 (ddt, J=17.3, 10.5, 5.9 Hz, 1H), 5.71 (m, 1H), 5.34 (m, 1H), 5.26 (m, 1H), 4.71-4.62 (m, 2H), 3.68 (dd, J=13.9, 7.8 Hz, 1H), 3.53 (dd, J=13.9, 5.6 Hz, 1H), 2.64-2.47 (m, 3H), 2.04 (m, 1H), 1.84 (m, 1H), 1.77-1.58 (m, 3H); $^{13}$C NMR (126 MHz, CDCl$_3$) δ 208.9, 170.7, 154.8, 151.1, 131.5, 129.3, 125.4, 121.6, 119.5, 66.5, 62.1, 45.0, 40.9, 34.0, 27.3, 22.1; IR (Neat Film, NaCl) 3377, 2943, 1745, 1728, 1709, 1514, 1489, 1202, 1143 cm$^{-1}$; HRMS (ESI+) m/z calc'd for C$_{18}$H$_{22}$NO$_5$ [M+H]$^+$: 332.1492. found 332.1483.

Allyl 1-((4-fluorophenoxy)carbonylaminomethyl)-2-oxocyclohexane-1-carboxylate (3e)

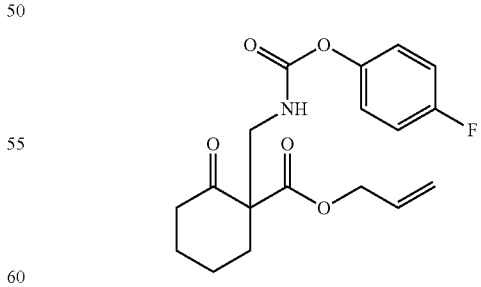

The reaction was conducted according to representative procedure A. Keto ester 1 (182 mg, 1.00 mmol); sulfonylmethyl carbamate 2e (371 mg, 1.20 mmol); Cs$_2$CO$_3$ (910 mg, 2.50 mmol). The reaction mixture was stirred for 24 h. Flash column chromatography (SiO$_2$, 15% EtOAc in hexanes) afforded α-aminomethyl β-keto ester 3e (278 mg, 0.796 mmol, 80% yield) as a colorless oil. $R_f$=0.28 (25% EtOAc in hexanes); $^1$H NMR (500 MHz, CDCl$_3$) δ 7.08-6.98 (m, 4H), 5.91 (ddt, J=17.2, 10.5, 5.9 Hz, 1H), 5.72 (m, 1H), 5.34 (m, 1H), 5.26 (m, 1H), 4.68-4.60 (m, 2H), 3.67 (dd, J=13.9, 7.8 Hz, 1H), 3.52 (dd, J=13.9, 5.5 Hz, 1H), 2.64-2.46 (m, 3H), 2.04 (m, 1H), 1.83 (m, 1H), 1.76-1.57 (m, 3H); $^{13}$C NMR (126 MHz, CDCl$_3$) δ 208.9, 170.7, 160.0 (J=243 Hz), 154.8, 147.0 (J=4 Hz), 131.4, 123.0 (J=9 Hz), 119.5, 115.9 (J=23 Hz), 66.6, 62.1, 45.1, 40.9, 34.0, 27.3, 22.1; IR (Neat Film, NaCl) 3377, 2944, 1746, 1732, 1711, 1497, 1219, 1193, 1147 cm$^{-1}$; HRMS (ESI+) m/z calc'd for C$_{18}$H$_{21}$FNO$_5$ [M+H]$^+$: 350.1398. found 350.1392.

Allyl 1-(benzamidomethyl)-2-oxocyclohexane-1-carboxylate (3f)

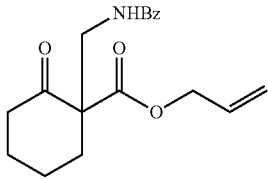

The reaction was conducted according to representative procedure A. Keto ester 1 (182 mg, 1.00 mmol); sulfonylmethyl carbamate 2f (413 mg, 1.50 mmol); Cs$_2$CO$_3$ (977 mg, 3.0 mmol). The reaction mixture was stirred for 24 h. Flash column chromatography (SiO$_2$, 15% EtOAc in hexanes) afforded α-aminomethyl β-keto ester 3f (250 mg, 0.793 mmol, 79% yield) as a white amorphous solid. $R_f$=0.30 (40% EtOAc in hexanes); $^1$H NMR (500 MHz, CDCl$_3$) δ 7.72-7.67 (m, 2H), 7.49-7.44 (m, 1H), 7.42-7.36 (m, 2H), 6.96-6.87 (m, 1H), 5.83 (ddt, J=17.2, 10.4, 6.0 Hz, 1H), 5.27 (dq, J=17.1, 1.4 Hz, 1H), 5.18 (dq, J=10.4, 1.2 Hz, 1H), 4.65-4.52 (m, 2H), 3.96 (dd, J=13.6, 7.7 Hz, 1H), 3.65 (dd, J=13.6, 5.2 Hz, 1H), 2.61-2.49 (m, 3H), 2.05-1.97 (m, 1H), 1.87-1.81 (m, 1H), 1.75-1.58 (m, 3H); $^{13}$C NMR (126 MHz, CDCl$_3$) δ 209.5, 170.8, 167.4, 134.4, 131.6, 131.4, 128.6, 127.0, 119.5, 66.6, 62.2, 43.3, 40.9, 34.2, 27.2, 22.1; IR (Neat Film, NaCl) 3447, 3356, 3061, 3028, 2943, 2866, 1712, 1667, 1651, 1602, 1580, 1519, 1488, 1450, 1307, 1280, 1203, 1142 cm$^{-1}$; FIRMS (ESI+) m/z calc'd for C$_{18}$H$_{22}$NO$_4$ [M+H]$^+$: 316.1543. found 316.1559.

Allyl 1-(((4-methylphenyl)sulfonamido)methyl)-2-oxocyclohexane-1-carboxylate (3g)

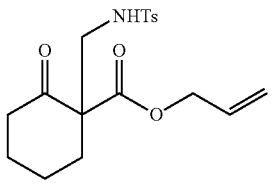

The reaction was conducted according to representative procedure A. Keto ester 1 (182 mg, 1.00 mmol); sulfonylmethyl carbamate 2g (488 mg, 1.50 mmol); Cs$_2$CO$_3$ (977 mg, 3.0 mmol). The reaction mixture was stirred for 24 h. Flash column chromatography (SiO$_2$, 25% EtOAc in hexanes) afforded α-aminomethyl β-keto ester 3g (365 mg, 0.999 mmol, >99% yield) as a clear colorless oil. $R_f$=0.25 (25% EtOAc in hexanes); $^1$H NMR (500 MHz, CDCl$_3$) δ 7.73-7.69 (m, 2H), 7.30 (dd, J=8.4, 1.0 Hz, 2H), 5.88 (ddt, J=17.2, 10.4, 5.9 Hz, 1H), 5.32 (dq, J=17.2, 1.5 Hz, 1H), 5.27 (dq, J=10.4, 1.2 Hz, 1H), 5.20 (dd, J=8.3, 5.8 Hz, 1H), 4.61 (dt, J=5.9, 1.3 Hz, 2H), 3.21 (dd, J=12.5, 8.4 Hz, 1H), 3.06 (dd, J=12.5, 5.8 Hz, 1H), 2.65-2.56 (m, 1H), 2.46-2.36 (m, 4H), 2.06-1.97 (m, 1H), 1.82-1.76 (m, 1H), 1.72-1.58 (m, 4H); $^{13}$C NMR (126 MHz, CDCl$_3$) δ 209.0, 170.4, 143.6, 137.0, 131.4, 129.9, 127.1, 119.6, 66.6, 61.6, 47.2, 40.9, 34.1, 27.0, 22.1, 21.7; IR (Neat Film, NaCl) 3289, 2942, 2867, 1728, 1709, 1451, 1335, 1206, 1163, 1092 cm$^{-1}$; HRMS (FAB+) m/z calc'd for C$_{18}$H$_{24}$NO$_5$S [M+H]$^+$: 366.1375. found 366.1367.

2-Phenylallyl 1-(((tert-butoxycarbonyl)amino)methyl)-2-oxocyclohexane-1-carboxylate (6a)

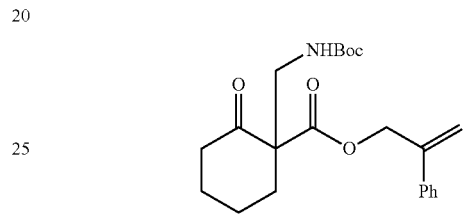

The reaction was conducted according to representative procedure A. Keto ester 5a (311 mg, 1.2 mmol); sulfonylmethyl carbamate 2a (392 mg, 1.44 mmol); Cs$_2$CO$_3$ (977 mg, 3.0 mmol). The reaction mixture was stirred for 24 h. Flash column chromatography (SiO$_2$, 15% EtOAc in hexanes) afforded α-aminomethyl β-keto ester 6a (368 mg, 0.95 mmol, 79% yield) as a pale yellow oil. $R_f$=0.5 (25% EtOAc in hexanes); $^1$H NMR (500 MHz, CDCl$_3$) δ 7.42-7.38 (m, 2H), 7.36-7.32 (m, 2H), 7.31-7.27 (m, 1H), 5.53 (d, J=0.9 Hz, 1H), 5.37 (q, J=1.1 Hz, 1H), 5.1 (d, J=13.0 Hz, 1H), 5.07 (t, J=7.0 Hz, 1H), 5.01 (d, J=13.0, 1H), 3.48 (dd, J=13.9, 7.6 Hz, 1H), 3.35 (dd, J=13.9, 5.8 Hz, 1H), 2.38-2.27 (m, 2H), 2.26-2.18 (m, 1H), 1.81 (m, 1H), 1.69-1.63 (m, 1H), 1.60-1.50 (m, 1H), 1.49-1.41 (m, 2H), 1.39 (s, 9H); $^{13}$C NMR (126 MHz, CDCl$_3$) δ 208.7, 170.8, 155.0, 142.4, 137.9, 128.7, 128.3, 126.3, 116.3, 79.4, 66.9, 62.3, 44.3, 40.6, 33.7, 28.4, 27.2, 21.9; IR (Neat Film, NaCl) 3458, 3411, 2975, 2938, 2866, 1715, 1499, 1365, 1167, 1141 cm$^{-1}$; HRMS (ESI+) m/z calc'd for C$_{22}$H$_{29}$NO$_5$Na [M+Na]$^+$: 410.1938. found 410.1923.

Allyl 1-(t-butoxycarbonylaminomethyl)-2-oxocycloheptane-1-carboxylate (6b)

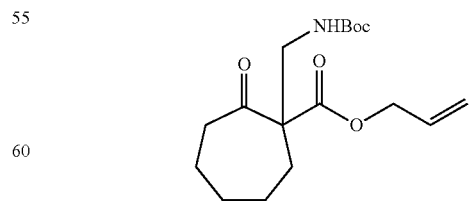

The reaction was conducted according to representative procedure A. Keto ester 5b (196 mg, 1.00 mmol); sulfonylmethyl carbamate 2a (326 mg, 1.20 mmol); Cs$_2$CO$_3$ (815 mg, 2.50 mmol). The reaction mixture was stirred for 24 h.

Flash column chromatography (SiO$_2$, 15% EtOAc in hexanes) afforded α-aminomethyl β-keto ester 6b (234 mg, 0.719 mmol, 72% yield) as a colorless oil. R$_f$=0.47 (20% EtOAc in hexanes); $^1$H NMR (500 MHz, CDCl$_3$) δ 5.90 (m, 1H), 5.32 (m, 1H), 5.25 (m, 1H), 5.18 (m, 1H), 4.68-4.56 (m, 2H), 3.56 (dd, J=14.0, 7.7 Hz, 1H), 3.50 (dd, J=14.0, 5.8 Hz, 1H), 2.68 (m, 1H), 2.56 (ddd, J=13.0, 8.3, 3.3 Hz, 1H), 2.08 (m, 1H), 1.86-1.76 (m, 2H), 1.73-1.48 (m, 5H), 1.40 (s, 9H); $^{13}$C NMR (126 MHz, CDCl$_3$) δ 210.2, 171.7, 156.1, 131.7, 119.0, 79.4, 66.2, 63.9, 45.3, 42.7, 31.7, 30.1, 28.4, 25.7, 25.3; IR (Neat Film, NaCl) 3461, 2976, 2933, 1718, 1501, 1456, 1366, 1248 m 1225, 1169 cm$^{-1}$; HRMS (ESI+) m/z calc'd for C$_{17}$H$_{27}$NO$_5$Na [M+Na]$^+$: 348.1781. found 348.1772.

Allyl 1-(t-butoxycarbonylaminomethyl)-2-oxocyclopentane-1-carboxylate (6c)

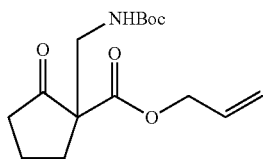 [SMILES: C=CCOC(=O)C1(CNC(=O)OC(C)(C)C)CCCC1=O]

The reaction was conducted according to representative procedure A. Keto ester 5c (168 mg, 1.00 mmol); sulfonylmethyl carbamate 2a (326 mg, 1.20 mmol); Cs$_2$CO$_3$ (815 mg, 2.50 mmol). The reaction mixture was stirred for 24 h. Flash column chromatography (SiO$_2$, 15% EtOAc in hexanes) afforded α-aminomethyl β-keto ester 6c (255 mg, 0.858 mmol, 86% yield) as a colorless oil. R$_f$=0.50 (33% EtOAc in hexanes); $^1$H NMR (500 MHz, CDCl$_3$) δ 5.87 (ddt, J=17.2, 10.4, 5.6 Hz, 1H), 5.29 (m, 1H), 5.24 (m, 1H), 5.13 (m, 1H), 4.67-4.55 (m, 2H), 3.50 (dd, J=14.0, 7.0 Hz 1H), 3.46 (dd, J=14.0, 6.0 Hz, 1H), 2.49-2.34 (m, 3H), 2.16-1.98 (m, 3H), 1.42 (s, 9H); $^{13}$C NMR (126 MHz, CDCl$_3$) δ 213.7, 171.3, 156.3, 131.5, 118.8, 79.7, 66.1, 61.5, 42.1, 38.2, 31.7, 28.4, 19.8; IR (Neat Film, NaCl) 3394, 2976, 1749, 1715, 1504, 1454, 1366, 1249, 1229, 1168, 966 cm$^{-1}$; HRMS (ESI+) m/z calc'd for C$_{15}$H$_{23}$NO$_5$Na [M+Na]$^+$: 320.1468. found 320.1467.

Allyl 1-(((tert-butoxycarbonyl)amino)methyl)-4-isobutoxy-2-oxocyclohept-3-ene-1-carboxylate (6d)

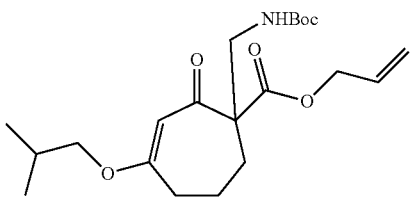 [SMILES: C=CCOC(=O)C1(CNC(=O)OC(C)(C)C)CCCC(OCC(C)C)=CC1=O]

The reaction was conducted according to representative procedure A. Keto ester 5d (100 mg, 0.375 mmol); sulfonylmethyl carbamate 2a (122 mg, 0.45 mmol); Cs$_2$CO$_3$ (305 mg, 0.936 mmol). The reaction mixture was stirred for 10 h. Flash column chromatography (SiO$_2$, 15% EtOAc in hexanes) afforded α-aminomethyl β-keto ester 6d (123 mg, 0.311 mmol, 83% yield) as a clear oil. R$_f$=0.5 (25% EtOAc in hexanes); $^1$H NMR (500 MHz, CDCl$_3$) δ 5.87 (ddt, J=17.3, 10.5, 5.7 Hz, 1H), 5.38 (s, 1H), 5.29 (dq, J=17.2, 1.6 Hz, 1H), 5.27 (m, 1H), 5.21 (dq, J=10.5, 1.3 Hz, 1H), 4.63 (ddt, J=13.2, 5.9, 1.4 Hz, 1H), 4.56 (ddt, J=13.3, 5.8, 1.4 Hz, 1H), 3.64 (dd, J=13.7, 7.8 Hz, 1H), 3.51-3.44 (m, 3H), 2.55 (ddd, J=17.9, 10.0, 4.2 Hz, 1H), 2.44 (ddd, J=17.8, 7.1, 3.8 Hz, 1H), 2.36 (m, 1H), 2.03-1.94 (m, 2H), 1.89-1.76 (m, 2H), 1.40 (s, 9H), 0.94 (dd, J=6.7, 1.5 Hz, 6H); $^{13}$C NMR (126 MHz, CDCl$_3$) δ 198.1, 174.9, 172.1, 156.1, 131.7, 118.8, 105.3, 79.3, 74.9, 66.2, 63.9, 46.4, 34.2, 29.3, 28.5, 27.9, 21.3, 19.2; IR (Neat Film, NaCl) 3459, 3394, 3083, 2961, 2934, 2874, 1734, 1718, 1636, 1610, 1499, 1388, 1366, 1232, 1171 cm$^{-1}$; HRMS (ESI+) m/z calc'd for C$_{21}$H$_{33}$NO$_6$Na [M+Na]$^+$: 418.2200. found 418.2192.

Allyl 2-(((tert-butoxycarbonyl)amino)methyl)-1-oxo-1,2,3,4-tetrahydronaphthalene-2-carboxylate (6e)

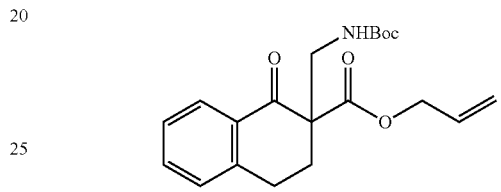

The reaction was conducted according to representative procedure A. Keto ester 5e (230.3 mg, 1.0 mmol); sulfonylmethyl carbamate 2a (326 mg, 1.2 mmol); Cs$_2$CO$_3$ (815 mg, 2.5 mmol). The reaction mixture was stirred for 24 h. Flash column chromatography (SiO$_2$, 15% EtOAc in hexanes) afforded α-aminomethyl β-keto ester 6e (395 mg, 0.999 mmol, >99% yield) as a pale yellow oil. R$_f$=0.5 (25% EtOAc in hexanes); $^1$H NMR (500 MHz, CDCl$_3$) δ 8.03 (dd, J=8.0, 1.4 Hz, 1H), 7.49 (td, J=7.5, 1.5 Hz, 1H), 7.34-7.29 (m, 1H), 7.23 (dq, J=7.8, 0.7 Hz, 1H), 5.86-5.76 (m, 1H), 5.33-5.27 (m, 1H), 5.22-5.14 (m, 2H), 4.61 (dt, J=2.4, 1.4 Hz, 1H), 4.59 (dt, J=2.4, 1.4 Hz, 1H), 3.79 (dd, J=13.9, 7.9 Hz, 1H), 3.56 (dd, J=13.9, 5.4 Hz, 1H), 3.10 (dt, J=17.5, 5.4 Hz, 1H), 3.02 (ddd, J=17.4, 9.4, 4.8 Hz, 1H), 2.57 (dt, J=13.8, 5.3 Hz, 1H), 2.20 (ddd, J=14.1, 9.5, 5.0 Hz, 1H), 1.41 (s, 9H); $^{13}$C NMR (126 MHz, CDCl$_3$) δ 195.6, 171.0, 156.1, 143.4, 134.1, 131.9, 131.5, 129.0, 128.0, 127.0, 118.7, 79.5, 66.1, 59.4, 43.6, 29.3, 28.5, 25.8; IR (Neat Film, NaCl) 3454, 3395, 2977, 2934, 1731, 1717, 1683, 1601, 1505, 1456, 1366, 1235, 1170 cm$^{-1}$; FIRMS (FAB+) m/z calc'd for C$_{20}$H$_{26}$NO$_5$ [M+H]$^+$: 360.1811. found 360.1801.

Allyl 1-benzyl-3-(((tert-butoxycarbonyl)amino)methyl)-4-oxopiperidine-3-carboxylate (6f)

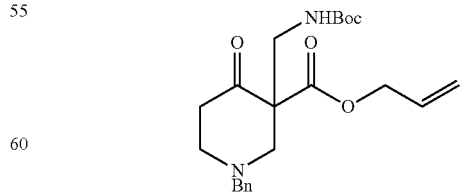

The reaction was conducted according to representative procedure A. Keto ester 5f (296 mg, 1.08 mmol); sulfonylmethyl carbamate 2a (353 mg, 1.296 mmol); Cs$_2$CO$_3$ (882 mg, 2.7 mmol). The reaction mixture was stirred for 24 h.

Flash column chromatography (SiO₂, 15% EtOAc in hexanes) afforded α-aminomethyl β-keto ester 6f (349 mg, 0.867 mmol, 80% yield) as a clear colorless oil. $R_f$=0.45 (25% EtOAc in hexanes); ¹H NMR (500 MHz, C₆D₆) δ 7.20-7.12 (m, 4H), 7.11-7.05 (m, 1H), 5.71 (ddt, J=16.5, 10.9, 5.7 Hz, 1H), 5.37 (t, J=6.8 Hz, 1H), 5.09 (dd, J=17.2, 1.6 Hz, 1H), 4.94 (dq, J=10.4, 1.3 Hz, 1H), 4.47 (d, J=5.8, 1.4 Hz, 2H), 3.63 (dd, J=13.9, 6.0 Hz, 1H), 3.57 (dd, J=13.9, 7.4 Hz, 1H), 3.23-3.20 (m, 1H), 3.19 (d, J=13.5 Hz, 1H), 3.10 (d, J=13.4 Hz, 1H), 2.65 (ddd, J=14.3, 10.0, 6.7 Hz, 1H), 2.37-2.29 (m, 2H), 1.99 (d, J=11.6 Hz, 1H), 1.93-1.87 (m, 1H), 1.37 (s, 9H); ¹³C NMR (126 MHz, C₆D₆) δ 205.9, 170.5, 155.9, 138.3, 132.2, 129.0, 128.7, 127.6, 118.4, 79.0, 66.1, 62.9, 61.9, 58.9, 53.1, 43.0, 40.3, 28.4; IR (Neat Film, NaCl) 3457, 2976, 2925, 2811, 1718, 1499, 1366, 1250, 1225, 1169 cm⁻¹; HRMS (FAB+) m/z calc'd for C₂₂H₃₁N₂O₅ [M+H]⁺: 403.2233. found 403.2238.

Allyl 1-benzoyl-3-(tert-butoxycarbonylaminomethyl)-2-oxopiperidine-3-carboxylate (6g)

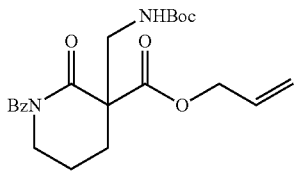

The reaction was conducted according to representative procedure A. Amido ester 5g (231 mg, 0.800 mmol); sulfonylmethyl carbamate 2a (261 mg, 0.960 mmol); Cs₂CO₃ (652 mg, 2.00 mmol). The reaction mixture was stirred for 24 h. Flash column chromatography (SiO₂, 15→20% EtOAc in hexanes) afforded α-aminomethyl amido ester 6g (245 mg, 0.588 mmol, 74% yield) as a colorless oil. $R_f$=0.36 (33% EtOAc in hexanes); ¹H NMR (500 MHz, CDCl₃) δ 7.81-7.74 (m, 2H), 7.50 (m, 1H), 7.44-7.36 (m, 2H), 5.97 (ddt, J=16.6, 10.4, 6.0 Hz, 1H), 5.40 (m, 1H), 5.33 (m, 1H), 5.15 (m, 1H), 4.82-4.63 (m, 2H), 3.91-3.74 (m, 2H), 3.71 (dd, J=13.9, 7.5 Hz, 1H), 3.50 (dd, J=13.9, 5.9 Hz, 1H), 2.43 (m, 1H), 2.12-1.91 (m, 3H), 1.41 (s, 9H); ¹³C NMR (126 MHz, CDCl₃) δ 174.9, 172.2, 170.7, 156.1, 135.6, 132.1, 131.3, 128.3, 128.3, 119.9, 79.7, 66.8, 58.4, 46.8, 44.7, 29.1, 28.4, 20.0; IR (Neat Film, NaCl) 3446, 2976, 1714, 1684, 1500, 1449, 1391, 1366, 1271, 1249, 1164, 1141, 939 cm⁻¹; HRMS (ESI+) m/z calc'd for C₂₂H₂₈N₂O₆Na [M+Na]⁺: 439.1840. found 439.1854.

Allyl 4-benzoyl-2-(tert-butoxycarbonylaminomethyl)-3-oxomorpholine-2-carboxylate (6h)

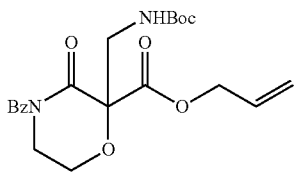

The reaction was conducted according to representative procedure A. Morpholinone 5h (100 mg, 0.346 mmol); sulfonylmethyl carbamate 2a (188 mg, 0.691 mmol); Cs₂CO₃ (338 mg, 1.04 mmol). The reaction mixture was stirred for 24 h. Flash column chromatography (SiO₂, 20→25% EtOAc in hexanes) afforded α-aminomethyl morpholinone 6h (132 mg, 0.315 mmol, 91% yield) as a colorless oil. $R_f$=0.34 (10% EtOAc in toluene); ¹H NMR (500 MHz, CDCl₃) δ 7.67-7.65 (m, 2H), 7.52 (m, 1H), 7.43-7.38 (m, 2H), 5.97 (m, 1H), 5.41 (m, 1H), 5.33 (m, 1H), 5.00 (brs, 1H), 4.76-4.73 (m, 2H), 4.30-4.17 (m, 2H), 4.05-3.90 (m, 2H), 3.87-3.72 (m, 2H), 1.42 (s, 9H); ¹³C NMR (126 MHz, CDCl₃) δ 172.7, 167.7, 167.5, 155.8, 134.7, 132.5, 131.0, 128.5, 128.3, 119.9, 83.1, 79.9, 67.2, 62.1, 45.0, 44.8, 28.4; IR (Neat Film, NaCl) 3388, 2977, 2934, 1746, 1714, 1693, 1507, 1449, 1367, 1317, 1279, 1233, 1165, 1066, 944, 757, 727, 693 cm⁻¹; HRMS (ESI+) m/z calc'd for C₂₁H₂₆N₂O₇Na [M+Na]⁺: 441.1632. found 441.1636.

Allyl 3-(((tert-butoxycarbonyl)amino)methyl)-4-oxo-9-tosyl-2,3,4,9-tetrahydro-1H-carbazole-3-carboxylate (6i)

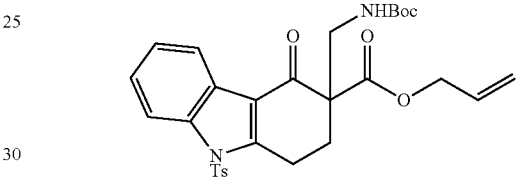

The reaction was conducted according to representative procedure A. Keto ester 5i (400 mg, 0.994 mmol); sulfonylmethyl carbamate 2a (307 mg, 1.13 mmol); Cs₂CO₃ (770 mg, 2.36 mmol). The reaction mixture was stirred for 24 h. Flash column chromatography (SiO₂, 15% EtOAc in hexanes) afforded α-aminomethyl β-keto ester 6i (418 mg, 0.756 mmol, 80% yield) as a clear colorless oil. $R_f$=0.33 (25% EtOAc in hexanes); ¹H NMR (500 MHz, CDCl₃) δ 8.21-8.17 (m, 1H), 8.15-8.12 (m, 1H), 7.78 (d, J=8.4 Hz, 2H), 7.38-7.31 (m, 2H), 7.27 (d, J=8.4 Hz, 2H), 5.80 (m, 1H), 5.25-5.17 (m, 2H), 5.15 (m, 1H), 4.58 (dt, J=5.8, 1.4 Hz, 2H), 3.74 (dd, J=14.0, 7.7 Hz, 1H), 3.59 (m, 2H), 3.41 (ddd, J=19.2, 8.3, 5.2 Hz, 1H), 2.67 (dt, J=13.9, 5.4 Hz, 1H), 2.37 (s, 3H), 2.28 (m, 1H), 1.42 (s, 9H); ¹³C NMR (126 MHz, CDCl₃) δ 191.4, 170.6, 156.1, 150.7, 146.1, 136.2, 135.3, 131.5, 130.4, 126.9, 125.8, 125.7, 125.2, 121.9, 118.9, 117.1, 114.0, 79.6, 66.2, 59.3, 43.3, 29.2, 28.5, 22.1, 21.8; IR (Neat Film, NaCl) 3445, 3054, 2977, 2933, 2254, 1733, 1713, 1596, 1558, 1505, 1481, 1451, 1410, 1380, 1244, 1174, 1090 cm⁻¹; HRMS (ESI+) m/z calc'd for C₂₉H₃₃N₂O₇S [M+H]⁺: 553.2003. found 553.1994.

Example 2. Representative Procedure for Palladium-Catalyzed Allelic Alkylation

With β-keto esters 3a-g in hand, this substrate class was investigated in the context of palladium-catalyzed allylic alkylation as shown in Table 1. Exposure of Boc-protected substrate 3a to a catalytic phosphinooxazoline-palladium(O) complex in toluene at ambient temperature afforded the desired product 4a in 94% yield and 86% ee (entry 1). Cbz-protected 3b also gave excellent yield and ee (entry 2). It is important to note that no N-alkylated side products were detected, a result that highlights the mild nature of these reaction conditions. Arylcarbamates 3c-e gave slightly decreased enantioselectivities in the products (entries 3-5). We also examined benzoyl and tosyl protecting groups.

TABLE 1

Optimization of the Amine Protecting Group.[a]

| entry | R (3→4) | | yield (%) | ee (%)[b] |
|---|---|---|---|---|
| 1 | Boc (3a→4a) | | 94 | 86 |
| 2 | Cbz (3b→4b) | | 96 | 86 |
| 3 | | X = OMe (3c→4c) | 91 | 83 |
| 4 | | X = H (3d→4d) | 90 | 77 |
| 5 | | X = F (3e→4e) | 84 | 77 |
| 6 | Bz (3f→4t) | | ND[c] | 56 |
| 7 | Ts (39→4g) | | 54 | 24 |

[a]Reaction performed with 0.2 mmol of 3, 5 mol % of Pd$_2$(dba)$_3$ (dba = dibenzylideneacetone), 12.5 mol % of (S)-(CF$_3$)$_3$-t-BuPHOX L1 at 0.033M in toluene at 23° C.
[b]Determined by chiral SFC analysis. Absolute stereochemistry has been assigned by analogy, except in entry 2, which was assigned by conversion into (−)-isonitramine.
[c]A yield was not determined.

Please note that the absolute configuration of all products 4 and 7 has been inferred from previous studies (Behenna, D. C., et al., *Chem. Eur. J.* 2011, 17, 14199-14223), with the exception of 4b, which was assigned by conversion to (−)-isonitramine.

Representative Procedure B

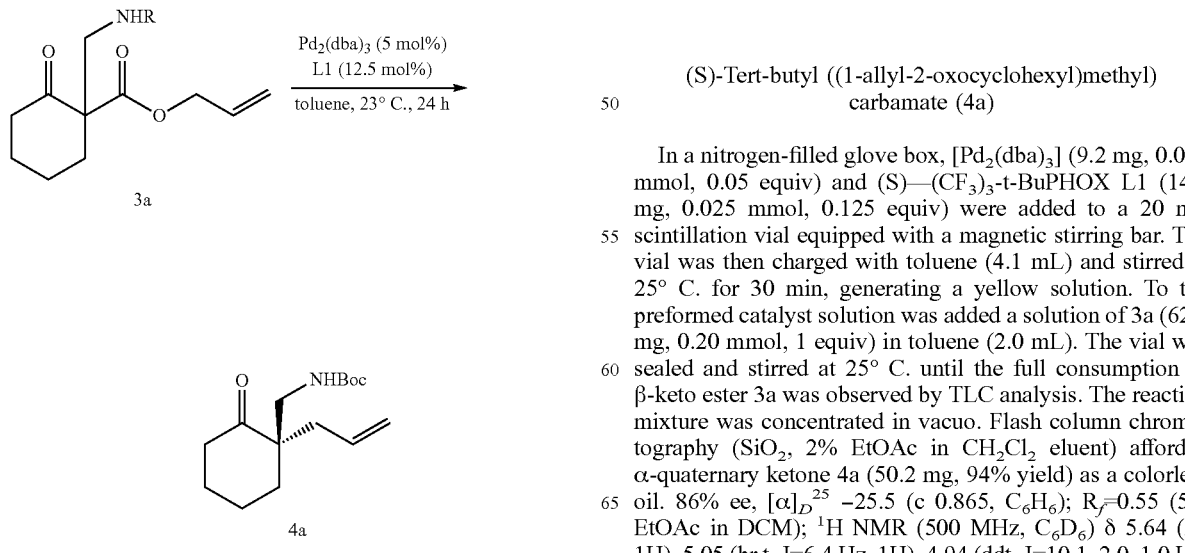

(S)-Tert-butyl ((1-allyl-2-oxocyclohexyl)methyl) carbamate (4a)

In a nitrogen-filled glove box, [Pd$_2$(dba)$_3$] (9.2 mg, 0.010 mmol, 0.05 equiv) and (S)—(CF$_3$)$_3$-t-BuPHOX L1 (14.8 mg, 0.025 mmol, 0.125 equiv) were added to a 20 mL scintillation vial equipped with a magnetic stirring bar. The vial was then charged with toluene (4.1 mL) and stirred at 25° C. for 30 min, generating a yellow solution. To the preformed catalyst solution was added a solution of 3a (62.3 mg, 0.20 mmol, 1 equiv) in toluene (2.0 mL). The vial was sealed and stirred at 25° C. until the full consumption of β-keto ester 3a was observed by TLC analysis. The reaction mixture was concentrated in vacuo. Flash column chromatography (SiO$_2$, 2% EtOAc in CH$_2$Cl$_2$ eluent) afforded α-quaternary ketone 4a (50.2 mg, 94% yield) as a colorless oil. 86% ee, [α]$_D^{25}$ −25.5 (c 0.865, C$_6$H$_6$); R$_f$=0.55 (5% EtOAc in DCM); $^1$H NMR (500 MHz, C$_6$D$_6$) δ 5.64 (m, 1H), 5.05 (br t, J=6.4 Hz, 1H), 4.94 (ddt, J=10.1, 2.0, 1.0 Hz, 1H), 4.87 (dq, J=17.0, 1.5 Hz, 1H), 3.30 (dd, J=13.9, 7.2 Hz, 1H), 3.24 (dd, J=13.9, 6.1 Hz, 1H), 2.15-2.08 (m, 2H), 2.01-1.91 (m, 2H), 1.44 (s, 9H), 1.41-1.30 (m, 2H), 1.25-1.12 (m, 2H); $^{13}$C NMR (126 MHz, C$_6$D$_6$) δ 213.5, 156.2, 133.3, 118.5, 78.7, 53.1, 45.2, 39.1, 37.9, 33.7, 28.5, 27.1, 20.6; IR (Neat Film, NaCl) 3462, 3395, 2977, 2939, 2867, 1718, 1499, 1167 cm$^{-1}$; HRMS (ESI+) m/z calc'd for C$_{15}$H$_{25}$NO$_3$Na [M+Na]$^+$: 290.1727. found 290.1718; SFC conditions: 10% IPA, 2.5 mL/min, Chiralpak AD-H column, λ=210 nm, t$_R$ (min): major=7.65, minor=8.46.

Spectroscopic Data for Exemplary Alkylation Products (S)-Benzyl (1-allyl-2-oxocyclohexyl)methylcarbamate (4b)

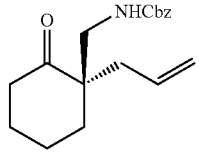

The reaction was conducted according to representative procedure B. Keto ester 3b (69.1 mg, 0.200 mmol). The reaction mixture was stirred at 23° C. for 14 h. Flash column chromatography (SiO$_2$, 10→15% EtOAc in hexanes) afforded ketone 4b (57.7 mg, 0.191 mmol, 96% yield) as a colorless oil. 86% ee, [α]$_D^{25}$ −38.6 (c 1.20, CHCl$_3$); R$_f$=0.44 (25% EtOAc in hexanes); $^1$H NMR (300 MHz, CDCl$_3$) δ 7.42-7.25 (m, 5H), 5.67 (m, 1H), 5.21 (m, 1H), 5.16-5.00 (m, 4H), 3.34 (dd, J=13.9, 5.9 Hz, 1H), 3.24 (dd, J=13.9, 7.4 Hz, 1H), 2.54-2.20 (m, 4H), 1.99 (m, 1H), 1.81-1.60 (m, 5H); $^{13}$C NMR (126 MHz, CDCl$_3$) δ 215.5, 156.9, 136.7, 132.2, 128.6, 128.2, 128.1, 119.2, 66.8, 53.2, 45.4, 39.3, 38.0, 33.7, 27.2, 20.6; IR (Neat Film, NaCl) 3351, 2937, 1722, 1702, 1510, 1454, 1234, 1134 cm$^{-1}$; HRMS (ESI+) m/z calc'd for C$_{18}$H$_{24}$NO$_3$ [M+H]$^+$: 302.1751. found 302.1756; SFC conditions: 5% IPA, 2.5 mL/min, Chiralpak AD-H column, λ=210 nm, t$_R$ (min): major=8.12, minor=9.06.

(S)-4-methoxyphenyl (1-allyl-2-oxocyclohexyl)methylcarbamate (4c)

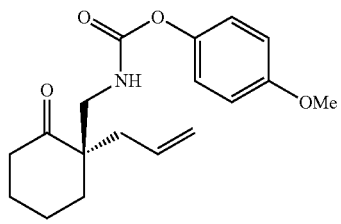 [SMILES: C=CC[C@]1(CNC(=O)Oc2ccc(OC)cc2)CCCCC1=O]

The reaction was conducted according to representative procedure B. Keto ester 3c (72.3 mg, 0.200 mmol). The reaction mixture was stirred at 23° C. for 24 h. Flash column chromatography (SiO$_2$, 15→20% EtOAc in hexanes) afforded ketone 4c (57.6 mg, 0.181 mmol, 91% yield) as a colorless oil. 83% ee, [α]$_D^{25}$ −29.3 (c 0.76, CHCl$_3$); R$_f$=0.25 (25% EtOAc in hexanes); $^1$H NMR (500 MHz, CDCl$_3$) δ 7.05-6.97 (m, 2H), 6.90-6.81 (m, 2H), 5.70 (m, 1H), 5.49 (m, 1H), 5.18-5.09 (m, 2H), 3.78 (s, 3H), 3.40 (dd, J=13.9, 6.0 Hz, 1H), 3.28 (dd, J=13.9, 7.2 Hz, 1H), 2.55-2.44 (m, 2H), 2.41-2.28 (m, 2H), 2.03 (m, 1H), 1.90-1.64 (m, 5H); $^{13}$C NMR (126 MHz, CDCl$_3$) δ 215.6, 157.0, 155.6, 144.8, 132.2, 122.5, 119.3, 114.4, 55.7, 53.2, 45.6, 39.4, 38.0, 33.8, 27.3, 20.6; IR (Neat Film, NaCl) 3345, 2937, 1740, 1700, 1501, 1201 cm$^{-1}$; HRMS (ESI+) m/z calc'd for C$_{18}$H$_{24}$NO$_4$ [M+H]$^+$: 318.1700. found 318.1705; SFC conditions: 10% IPA, 2.5 mL/min, Chiralcel OB-H column, λ=210 nm, t$_R$ (min): major=9.47, minor=11.13.

(S)-phenyl (1-allyl-2-oxocyclohexyl)methylcarbamate (4d)

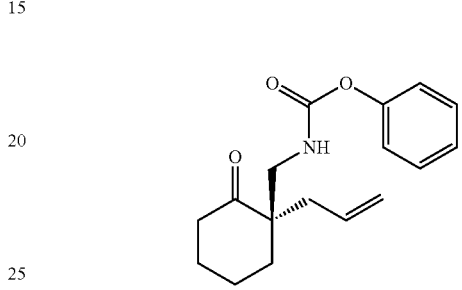

The reaction was conducted according to representative procedure B. Keto ester 3d (66.3 mg, 0.200 mmol). The reaction mixture was stirred at 23° C. for 24 h. Flash column chromatography (SiO$_2$, 1015% EtOAc in hexanes) afforded ketone 4d (51.5 mg, 0.179 mmol, 90% yield) as a colorless oil. 77% ee, [α]$_D^{25}$ −28.9 (c 0.40, CHCl$_3$); R$_f$=0.29 (25% EtOAc in hexanes); $^1$H NMR (500 MHz, CDCl$_3$) δ 7.34 (t, J=7.7 Hz, 2H), 7.17 (m, 1H), 7.11 (d, J=8.0 Hz, 2H), 5.70 (m, 1H), 5.53 (m, 1H), 5.20-5.11 (m, 2H), 3.41 (dd, J=14.0, 6.0 Hz, 1H), 3.29 (dd, J=14.0, 7.2 Hz, 1H), 2.55-2.45 (m, 2H), 2.42-2.29 (m, 2H), 2.03 (m, 1H), 1.90-1.65 (m, 5H); $^{13}$C NMR (126 MHz, CDCl$_3$) δ 215.7, 155.1, 151.2, 132.1, 129.3, 125.3, 121.6, 119.4, 53.2, 45.6, 39.4, 38.0, 33.8, 27.3, 20.6; IR (Neat Film, NaCl) 3346, 2937, 1743, 1701, 1490, 1203 cm$^{-1}$; HRMS (ESI+) m/z calc'd for C$_{17}$H$_{22}$NO$_3$ [M+H]$^+$: 288.1594. found 288.1589; SFC conditions: 10% IPA, 2.5 mL/min, Chiralcel OB-H column, λ=210 nm, t$_R$ (min): major=6.53, minor=8.13.

(S)-4-fluorophenyl (1-allyl-2-oxocyclohexyl)methylcarbamate (4e)

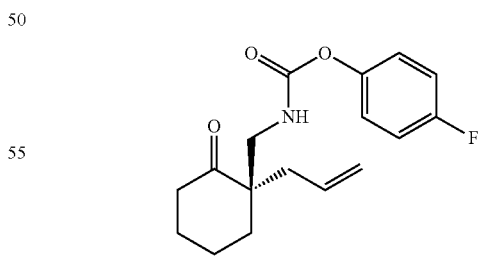

The reaction was conducted according to representative procedure B. Keto ester 3e (69.9 mg, 0.200 mmol). The reaction mixture was stirred at 23° C. for 24 h. Flash column chromatography (SiO$_2$, 10→15% EtOAc in hexanes) afforded ketone 4e (51.4 mg, 0.168 mmol, 84% yield) as a colorless oil. 77% ee, [α]$_D^{25}$ −27.4 (c 0.78, CHCl$_3$); R$_f$=0.37 (25% EtOAc in hexanes); $^1$H NMR (500 MHz, CDCl$_3$) δ

7.10-6.97 (m, 4H), 5.69 (m, 1H), 5.54 (m, 1H), 5.17-5.10 (m, 2H), 3.40 (dd, J=13.9, 6.0 Hz, 1H), 3.27 (dd, J=13.9, 7.2 Hz, 1H), 2.55-2.45 (m, 2H), 2.41-2.29 (m, 2H), 2.04 (m, 1H), 1.91-1.63 (m, 5H); $^{13}$C NMR (126 MHz, CDCl$_3$) δ 215.7, 160.0 (J=243 Hz), 155.1, 147.1 (J=4 Hz), 132.1, 123.1 (J=7 Hz), 119.4, 115.9 (J=24 Hz), 53.2, 45.6, 39.4, 37.9, 33.8, 27.3, 20.6; IR (Neat Film, NaCl) 3347, 2938, 1742, 1699, 1498, 1192 cm$^{-1}$; HRMS (ESI+) m/z calc'd for C$_{17}$H$_{21}$FNO$_3$ [M+H]$^+$: 306.1500. found 306.1493; SFC conditions: 10% IPA, 2.5 mL/min, Chiralpak AS-H column, λ=210 nm, t$_R$ (min): major=6.94, minor=8.24.

(S)—N-((1-allyl-2-oxocyclohexyl)methyl)benzamide (4f)

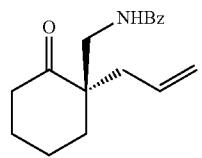

The reaction was conducted according to representative procedure B. Keto ester 3f (19.1 mg, 0.60 mmol). The reaction mixture was stirred at 23° C. for 20 h. Flash column chromatography (SiO$_2$, 10→15% EtOAc in hexanes) afforded ketone 4f as a colorless oil. 56% ee, R$_f$=0.23 (25% EtOAc in hexanes); $^1$H NMR (500 MHz, CDCl$_3$) δ 7.76-7.72 (m, 2H), 7.49 (m, 1H), 7.45-7.40 (m, 2H), 6.78 (m, 1H), 5.66 (m, 1H), 5.15 (d, J=1.2 Hz, 1H), 5.12 (m, 1H), 3.58 (dd, J=13.8, 6.1 Hz, 1H), 3.55 (dd, J=13.8, 6.1 Hz, 1H), 2.56-2.47 (m, 2H), 2.40-2.32 (m, 2H), 2.03 (m, 1H), 1.92-1.79 (m, 2H), 1.77-1.61 (m, 3H); $^{13}$C NMR (126 MHz, CDCl$_3$) δ 216.6, 167.5, 134.7, 132.3, 131.6, 128.7, 127.0, 119.4, 53.5, 43.9, 39.5, 38.3, 34.1, 27.4, 20.6; IR (Neat Film, NaCl) 3439, 3338, 3070, 2936, 2864, 1693, 1668, 1649, 1535, 1515, 1486, 1454, 1286, 1127 cm$^{-1}$; HRMS (ESI/APCI) m/z calc'd for C$_{17}$H$_{22}$NO$_2$ [M+H]$^+$: 272.1645. found 272.1638; SFC conditions: 20% IPA, 2.5 mL/min, Chiralpak AD-H column, λ=210 nm, t$_R$ (min): major=4.04, minor=4.91.

(S)—N-((1-allyl-2-oxocyclohexyl)methyl)-4-methylbenzenesulfonamide (4g)

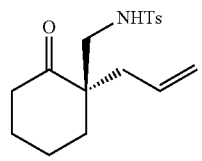

The reaction was conducted according to representative procedure B. Keto ester 3g (74.0 mg, 0.202 mmol). The reaction mixture was stirred at 23° C. for 20 h. Flash column chromatography (SiO$_2$, 15% EtOAc in hexanes) afforded ketone 4g (35.3 mg, 0.109 mmol, 54% yield) as a yellow oil. 24% ee, R$_f$=0.3 (25% EtOAc in hexanes); $^1$H NMR (500 MHz, CDCl$_3$) δ 7.71 (m, 2H), 7.30 (dd, J=8.3, 0.9 Hz, 2H), 5.61 (dddd, J=16.3, 10.8, 7.9, 6.9 Hz, 1H), 5.11-5.06 (m, 3H), 2.97 (dd, J=12.6, 6.7 Hz, 1H), 2.70 (dd, J=12.6, 7.5 Hz, 1H), 2.50-2.43 (m, 2H), 2.41 (s, 3H), 2.31-2.21 (m, 2H), 2.01 (m, 1H), 1.84-1.55 (m, 5H); $^{13}$C NMR (126 MHz, CDCl$_3$) δ 215.7, 143.4, 137.0, 131.5, 129.9, 127.0, 119.7, 52.5, 47.7, 39.2, 37.4, 33.4, 27.1, 21.6, 20.5; IR (Neat Film, NaCl) 3285, 3071, 2938, 2865, 1919, 1762, 1703, 1638, 1598, 1495, 1454, 1333, 1164, 1091 cm$^{-1}$; HRMS (ESI+) m/z calc'd for C$_{17}$H$_{24}$NO$_3$S [M+H]$^+$: 322.1471. found 322.1456; SFC conditions: 15% IPA, 2.5 mL/min, Chiralcel OJ-H column, λ=210 nm, t$_R$ (min): major=3.14, minor=3.85.

(S)-tert-butyl ((2-oxo-1-(2-phenylallyl)cyclohexyl)methyl)carbamate (7a)

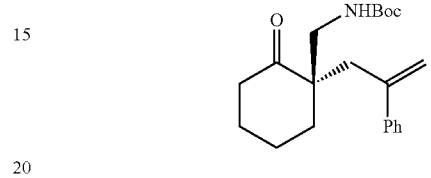

The reaction was conducted according to representative procedure B. Keto ester 6a (110 mg, 0.284 mmol); [Pd$_2$(pmdba)$_3$] (15.6 mg, 0.014 mmol, 0.05 equiv). The reaction mixture was stirred at 23° C. for 24 h. Flash column chromatography (SiO$_2$, 20% acetone in hexanes) afforded ketone 7a (88.7 mg, 0.258 mmol, 91% yield) as a yellow oil. 90% ee, [α]$_D^{25}$ −30.9 (c 4.45, CHCl$_3$); R$_f$=0.55 (25% EtOAc in hexanes); $^1$H NMR (500 MHz, CDCl$_3$) δ 7.32-7.26 (m, 5H), 5.23 (d, J=1.4 Hz, 1H), 5.08 (d, J=2.0 Hz, 1H), 4.67 (dd, J=8.3, 4.4 Hz, 1H), 3.16 (dd, J=14.0, 8.5 Hz, 1H), 3.09 (dd, J=13.9, 4.7 Hz, 1H), 2.99 (d, J=14.1 Hz, 1H), 2.71 (d, J=14.1 Hz, 1H), 2.38 (ddd, J=14.4, 10.8, 5.7 Hz, 1H), 2.30 (dt, J=13.9, 4.8 Hz, 1H), 1.87 (dt, J=15.3, 5.5 Hz, 1H), 1.77-1.60 (m, 5H), 1.38 (s, 9H); $^{13}$C NMR (126 MHz, CDCl$_3$) δ 214.9, 156.3, 144.9, 142.7, 128.6, 127.7, 126.7, 118.3, 79.1, 54.0, 44.9, 39.8, 39.7, 34.4, 28.5, 27.2, 20.9; IR (Neat Film, NaCl) 3463, 3374, 2975, 2935, 2865, 1713, 1703, 1699, 1505, 1455, 1365, 1247, 1169 cm$^{-1}$; HRMS (FAB+) m/z calc'd for C$_{21}$H$_{30}$NO$_3$ [M+H]$^+$: 344.2226. found 344.2236; SFC conditions: 15% IPA, 2.5 mL/min, Chiralpak AD-H column, λ=210 nm, t$_R$ (min): major=2.46, minor=2.78.

(S)-tert-Butyl (1-allyl-2-oxocycloheptyl)methylcarbamate (7b)

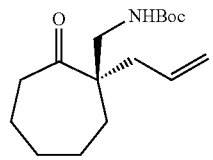 [SMILES: C=CC[C@]1(CNC(=O)OC(C)(C)C)CCCCCC1=O]

The reaction was conducted according to representative procedure B. Keto ester 6b (97.6 mg, 0.300 mmol). The reaction mixture was stirred at 23° C. for 20 h. Flash column chromatography (SiO$_2$, 10→15% EtOAc in hexanes) afforded ketone 7b (78.7 mg, 0.280 mmol, 93% yield) as a pale yellow oil. 87% ee, [α]$_D^{25}$ −22.7 (c 0.85, CHCl$_3$); R$_f$=0.53 (20% EtOAc in hexanes); $^1$H NMR (500 MHz, CDCl$_3$) δ 5.72 (ddt, J=17.3, 10.4, 7.5 Hz, 1H), 5.12-5.03 (m, 2H), 4.93 (brs, 1H), 3.31-3.19 (m, 2H), 2.65-2.56 (m, 1H), 2.46 (ddd, J=11.3, 8.8, 2.5 Hz, 1H), 2.35 (m, 1H), 2.20 (m, 1H), 1.79-1.41 (m, 8H), 1.41 (s, 9H); $^{13}$C NMR (126 MHz, CDCl$_3$) δ 217.1, 156.2, 133.2, 118.8, 79.3, 54.8, 45.2, 41.1, 39.4, 33.3, 30.8, 28.5, 26.7, 24.7; IR (Neat Film, NaCl) 3372, 2930, 1716, 1698, 1503, 1365, 1247, 1117 cm$^{-1}$; HRMS (ESI+) m/z calc'd for C$_{17}$H$_{28}$NO$_3$ [M+H]$^+$: 282.2064. found 282.2051; SFC conditions: 5% IPA, 2.5 mL/min, Chiralpak AD-H column, λ=210 nm, t$_R$ (min): major=4.25, minor=4.63.

(S)-tert-Butyl (1-allyl-2-oxocyclopentyl)methylcarbamate (7c)

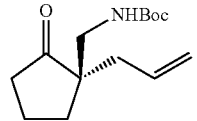 [SMILES: C=CC[C@]1(CNC(=O)OC(C)(C)C)CCCC1=O]

The reaction was conducted according to representative procedure B. Keto ester 6c (59.5 mg, 0.200 mmol). The reaction mixture was stirred at 23° C. for 20 h. Flash column chromatography (SiO$_2$, 10→15% EtOAc in hexanes) afforded ketone 7c (50.0 mg, 0.196 mmol, 98% yield) as a colorless oil. 82% ee, [α]$_D^{25}$ −12.8 (c 0.96, CHCl$_3$); R$_f$=0.38 (25% EtOAc in hexanes); $^1$H NMR (500 MHz, CDCl$_3$) δ 5.69 (ddt, J=17.4, 10.2, 7.4 Hz, 1H), 5.14-5.05 (m, 2H), 4.86 (brs, 1H), 3.25 (dd, J=13.9, 6.9 Hz, 1H), 3.14 (dd, J=13.9, 5.7 Hz, 1H), 2.30-2.23 (m, 2H), 2.20-2.13 (m, 2H), 1.99-1.79 (m, 4H), 1.43 (s, 9H); $^{13}$C NMR (126 MHz, CDCl$_3$) δ 222.6, 156.3, 133.0, 119.1, 79.5, 52.5, 44.0, 38.4, 37.5, 31.1, 28.5, 18.8; IR (Neat Film, NaCl) 3360, 2975, 1713, 1510, 1365, 1248, 1166 cm$^{-1}$; HRMS (ESI+) m/z calc'd for C$_{14}$H$_{23}$NO$_3$Na [M+Na]$^+$: 276.1570. found 276.1565; SFC conditions: 5% IPA, 2.5 mL/min, Chiralpak AD-H column, λ=210 nm, t$_R$ (min): major=2.97, minor=4.26.

(S)-tert-butyl ((1-allyl-4-isobutoxy-2-oxocyclohept-3-en-1-yl)methyl)carbamate (7d)

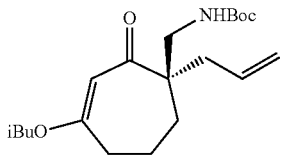

The reaction was conducted according to representative procedure B. Keto ester 6d (100 mg, 0.253 mmol); [Pd$_2$(pmdba)$_3$] (13.9 mg, 0.012 mmol). The reaction mixture was stirred at 23° C. for 24 h. Flash column chromatography (SiO$_2$, 10% EtOAc in hexanes) afforded ketone 7d (62.2 mg, 0.177 mmol, 70% yield) as a pale yellow oil. 92% ee, [α]$_D^{25}$ −28.7 (c 0.65, CHCl$_3$); R$_f$=0.6 (25% EtOAc in hexanes); $^1$H NMR (500 MHz, CDCl$_3$) δ 5.70 (ddt, J=17.5, 10.3, 7.4 Hz, 1H), 5.28 (s, 1H), 5.10-5.03 (m, 3H), 3.53-3.44 (m, 2H), 3.33 (dd, J=13.6, 6.4 Hz, 1H), 3.18 (dd, J=13.6, 6.4 Hz, 1H), 2.55-2.42 (m, 2H), 2.37-2.28 (m, 2H), 1.98 (dt, J=13.3, 6.7 Hz, 1H), 1.94-1.87 (m, 1H), 1.81-1.72 (m, 3H), 1.41 (s, 9H), 0.95 (d, J=6.7 Hz, 6H); $^{13}$C NMR (126 MHz, CDCl$_3$) δ 205.8, 172.7, 156.4, 133.4, 118.8, 104.9, 79.1, 74.7, 55.5, 47.1, 41.3, 36.1, 31.6, 28.6, 28.0, 20.5, 19.3; IR (Neat Film, NaCl) 3373, 3075, 2972, 2931, 2868, 1716, 1694, 1504, 1393, 1366, 1249, 1166 cm$^{-1}$; HRMS (FAB+) m/z calc'd for C$_{20}$H$_{34}$NO$_4$ [M+H]$^+$: 352.2488. found 352.2474; SFC conditions: 3% IPA, 2.5 mL/min, Chiralpak AS-H column, λ=254 nm, t$_R$ (min): major=4.41, minor=6.12.

(S)-tert-butyl ((2-allyl-1-oxo-1,2,3,4-tetrahydronaphthalen-2-yl)methyl)carbamate (7e)

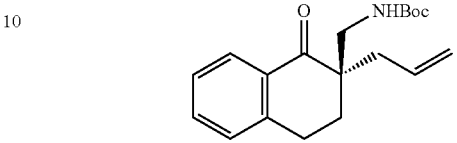

The reaction was conducted according to representative procedure B. Keto ester 6e (81 mg, 0.225 mmol); [Pd$_2$(pmdba)$_3$] (12.3 mg, 0.011 mmol, 0.05 equiv). The reaction mixture was stirred at 23° C. for 24 h. Flash column chromatography (SiO$_2$, 10% EtOAc in hexanes) afforded ketone 7e (52.2 mg, 0.167 mmol, 74% yield) as a pale yellow oil. 93% ee, [α]$_D^{25}$ −1.3 (c 1.32, CHCl$_3$); R$_f$=0.6 (25% EtOAc in hexanes); $^1$H NMR (500 MHz, CDCl$_3$) δ 8.00 (dd, J=8.0, 1.4 Hz, 1H), 7.48 (td, J=7.5, 1.5 Hz, 1H), 7.30 (td, J=7.6, 1.2 Hz, 1H), 7.23 (d, J=7.6 Hz, 1H), 5.79 (m, 1H), 5.15-5.05 (m, 3H), 3.50 (dd, J=13.9, 6.2 Hz, 1H), 3.29 (dd, J=13.9, 6.9 Hz, 1H), 3.11 (ddd, J=16.9, 11.1, 5.3 Hz, 1H), 2.94 (dt, J=17.5, 4.6 Hz, 1H), 2.37 (dd, J=14.2, 8.0 Hz, 1H), 2.28 (dd, J=14.2, 6.8 Hz, 1H), 2.11 (ddd, J=14.0, 11.1, 5.2 Hz, 1H), 2.03 (dt, J=14.0, 4.7 Hz, 1H), 1.41 (s, 9H); $^{13}$C NMR (126 MHz, CDCl$_3$) δ 202.2, 156.4, 143.5, 133.7, 132.7, 131.6, 129.0, 127.9, 126.9, 119.2, 79.2, 49.3, 44.8, 36.6, 28.9, 28.5, 25.0; IR (Neat Film, NaCl) 3449, 3378, 3073, 2976, 2930, 1716, 1699, 1678, 1600, 1505, 1455, 1365, 1232, 1170 cm$^{-1}$; HRMS (FAB+) m/z calc'd for C$_{19}$H$_{26}$NO$_3$ [M+H]$^+$: 316.1913. found 316.1920; SFC conditions: 15% IPA, 2.5 mL/min, Chiralpak AD-H column, λ=210 nm, t$_R$ (min): major=2.48, minor=2.80.

(S)-tert-butyl ((3-allyl-1-benzyl-4-oxopiperidin-3-yl)methyl)carbamate (7f)

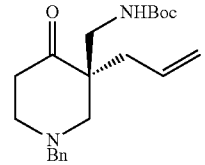 [SMILES: C=CC[C@]1(CNC(=O)OC(C)(C)C)CN(Cc2ccccc2)CCC1=O]

The reaction was conducted according to representative procedure B. Keto ester 6f (115 mg, 0.286 mmol); [Pd$_2$(pmdba)$_3$] (15.7 mg, 0.014 mmol, 0.05 equiv). The reaction mixture was stirred at 23° C. for 24 h. Flash column chromatography (SiO$_2$, 10% EtOAc in hexanes) afforded ketone 7f (79.3 mg, 0.223 mmol, 78% yield) as a pale yellow oil. 90% ee, [α]$_D^{25}$ −34.0 (c 1.58, CHCl$_3$); R$_f$=0.55 (25% EtOAc in hexanes); 1H NMR (500 MHz, CDCl$_3$) δ 7.37-7.27 (m, 5H), 5.61 (m, 1H), 5.07 (m, 1H), 5.04 (d, J=1.1 Hz, 1H), 5.00 (m, 1H), 3.58 (d, J=13.0 Hz, 1H), 3.53 (d, J=13.0 Hz, 1H), 3.37 (dd, J=14.0, 7.3 Hz, 1H), 3.19 (dd, J=14.0, 5.7 Hz, 1H), 2.84 (m, 1H), 2.69 (d, J=11.6 Hz, 1H), 2.63-2.50 (m, 3H), 2.48-2.36 (m, 3H), 1.41 (s, 9H); $^{13}$C NMR (126 MHz, CDCl$_3$) δ 212.8, 156.2, 138.3, 132.6, 129.0, 128.5, 127.4, 119.2, 79.3, 62.3, 59.7, 53.6, 53.1, 44.1, 39.5, 38.1, 28.5; IR (Neat Film, NaCl) 3452, 3373, 3063, 2976, 2929, 2807, 1713, 1638, 1504, 1453, 1391, 1365, 1248, 1170 cm$^{-1}$; HRMS (FAB+) m/z calc'd for C$_{21}$H$_{31}$N$_2$O$_3$ [M+H]$^+$: 359.2335. found 359.2345; SFC conditions: 8% IPA, 2.5 mL/min, Chiralpak AD-H column, λ=210 nm, t$_R$ (min): major=4.94, minor=6.46.

(S)-tert-Butyl ((3-allyl-1-benzoyl-2-oxopiperidin-3-yl)methyl)carbamate (7g)

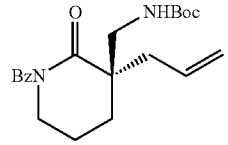

The reaction was conducted according to representative procedure B. Amido ester 6g (83.3 mg, 0.200 mmol). The reaction mixture was stirred at 40° C. for 20 h. Flash column chromatography (SiO$_2$, 15→20% EtOAc in hexanes) afforded lactam 7g (69.7 mg, 0.187 mmol, 94%) as a colorless oil. 90% ee, [α]$_D^{25}$ +33.6 (c 1.05, CHCl$_3$); R$_f$=0.29 (25% EtOAc in hexanes); 1H NMR (500 MHz, CDCl$_3$) δ 7.56-7.46 (m, 3H), 7.44-7.37 (m, 2H), 5.78 (m, 1H), 5.24-5.15 (m, 2H), 4.96 (m, 1H), 3.84 (m, 1H), 3.73 (ddd, J=12.7, 10.3, 4.3 Hz, 1H), 3.37 (dd, J=13.8, 6.5 Hz, 1H), 3.22 (dd, J=13.8, 6.5 Hz, 1H), 2.60 (dd, J=13.8, 8.0 Hz, 1H), 2.48 (dd, J=13.8, 6.7 Hz, 1H), 2.12-1.93 (m, 3H), 1.82 (m, 1H), 1.42 (s, 9H); $^{13}$C NMR (126 MHz, CDCl$_3$) δ 178.6, 175.4, 156.4, 136.3, 131.9, 131.8, 128.4, 127.6, 120.1, 79.5, 48.8, 47.2, 46.0, 39.7, 28.8, 28.5, 19.3; IR (Neat Film, NaCl) 3373, 2975, 1693, 1678, 1502, 1390, 1365, 1272, 1248, 1167 cm$^{-1}$; HRMS (ESI+) m/z calc'd for C$_{21}$H$_{28}$N$_2$O$_4$Na [M+Na]$^+$: 395.1941. found 395.1954; SFC conditions: 10% MeOH, 3.0 mL/min, Chiralpak AD-H column, λ=254 nm, t$_R$ (min): major=2.64, minor=3.12.

(R)-tert-Butyl ((2-allyl-4-benzoyl-3-oxomorpholin-2-yl)methyl)carbamate (7h)

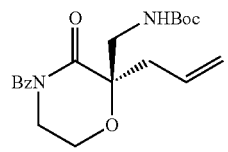

The reaction was conducted according to representative procedure B. Morpholinone 6h (33.0 mg, 0.079 mmol). The reaction mixture was stirred at 40° C. for 12 h. Flash column chromatography (SiO$_2$, 15→20% EtOAc in hexanes) afforded morpholinone 7h (27.3 mg, 0.073 mmol, 92%) as a colorless oil. 99% ee, [α]$_D^{25}$ +10.8 (c 0.93, CHCl$_3$); R$_f$=0.43 (33% EtOAc in hexanes); $^1$H NMR (500 MHz, CDCl$_3$) δ 7.57-7.48 (m, 3H), 7.43-7.38 (m, 2H), 5.89 (m, 1H), 5.23-5.17 (m, 2H), 4.88 (br s, 1H), 4.14-3.88 (m, 4H), 3.63 (m, 1H), 3.40 (dd, J=14.1, 5.6 Hz, 1H), 2.69 (dd, J=14.3, 7.4 Hz, 1H), 2.52 (dd, J=14.3, 7.0 Hz, 1H), 1.44 (s, 9H); $^{13}$C NMR (126 MHz, CDCl$_3$) δ 173.0, 172.6, 155.9, 135.6, 132.1, 131.7, 128.3, 128.1, 119.9, 82.2, 79.9, 60.6, 46.0, 45.5, 40.0, 28.5; IR (Neat Film, NaCl) 3382, 2978, 1707, 1689, 1509, 1367, 1281, 1250, 1225, 1166, 1091 cm$^{-1}$; HRMS (ESI+) m/z calc'd for C$_{20}$H$_{26}$N$_2$O$_5$Na [M+Na]$^+$: 397.1734. found 397.1728; SFC conditions: 3% MeOH, 2.5 mL/min, Chiralpak AS-H column, λ=254 nm, t$_R$ (min): major=4.06, minor=4.62.

(S)-tert-butyl ((3-allyl-4-oxo-9-tosyl-2,3,4,9-tetrahydro-1H-carbazol-3-yl)methyl)carbamate (7i)

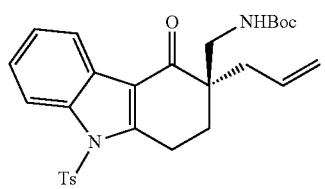 [SMILES: C=CC[C@]1(CNC(=O)OC(C)(C)C)CCc2c(c3ccccc3n2S(=O)(=O)c2ccc(C)cc2)C1=O]

The reaction was conducted according to representative procedure B. Keto ester 6i (100 mg, 0.181 mmol); [Pd$_2$(pmdba)$_3$] (10.0 mg, 0.009 mmol, 0.05 equiv). The reaction mixture was stirred at 40° C. for 48 h. Flash column chromatography (SiO$_2$, 10% EtOAc in hexanes) afforded ketone 7i (46.9 mg, 0.091 mmol, 51% yield) as a white foam. 92% ee, [α]$_D^{25}$ −13.3 (c 0.28, C$_6$H$_6$); R$_f$=0.45 (25% EtOAc in hexanes); $^1$H NMR (500 MHz, CDCl$_3$) δ 8.20 (m, 1H), 8.16 (dd, J=7.3, 1.8 Hz, 1H), 7.77 (d, J=8.4 Hz, 2H), 7.41-7.31 (m, 2H), 7.28 (m, 2H), 5.77 (m, 1H), 5.11 (m, 1H), 5.08 (dd, J=17.1, 1.8 Hz, 1H), 5.05 (br t, J=6.7 Hz, 1H), 3.49 (dd, J=13.9, 6.2 Hz, 1H), 3.44 (dt, J=19.2, 4.8 Hz, 1H), 3.33-3.28 (m, 1H), 3.27 (dd, J=13.9, 7.0 Hz, 1H), 2.38 (s, 3H), 2.32-2.28 (m, 2H), 2.16-2.11 (m, 2H), 1.40 (s, 9H); $^{13}$C NMR (126 MHz, CDCl$_3$) δ 199.1, 156.4, 150.1, 146.1, 136.4, 135.6, 132.9, 130.5, 126.8, 126.0, 125.6, 125.1, 121.9, 119.3, 116.6, 114.1, 79.4, 49.4, 44.6, 37.5, 29.5, 28.5, 21.8, 21.6; IR (Neat Film, NaCl) 3432, 3372, 3058, 2976, 2928, 1712, 1657, 1505, 1451, 1407, 1366, 1247, 1173 cm$^{-1}$; HRMS (ESI+) m/z calc'd for C$_{28}$H$_{33}$N$_2$O$_5$S [M+H]$^+$: 509.2105. found 509.2094; SFC conditions: 15% IPA, 2.5 mL/min, Chiralcel OB—H column, λ=210 nm, t$_R$ (min): major=7.21, minor=5.19.

TABLE 2

Two-step Synthesis of α-Aminomethyl Carbonyl Compounds from β-Oxo Esters.$^a$

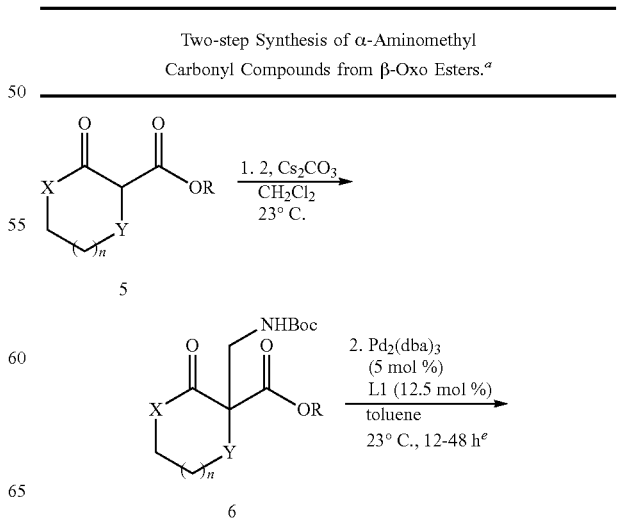

TABLE 2-continued

Two-step Synthesis of α-Aminomethyl Carbonyl Compounds from β-Oxo Esters.[a]

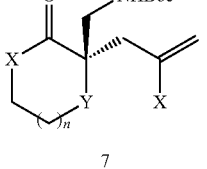

7

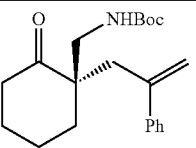

6a 79% yield
7a 91% yield, 90% ee[b,c]

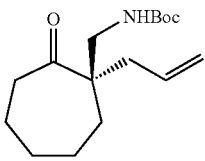 [SMILES: C=CC[C@]1(CNC(=O)OC(C)(C)C)CCCCCC1=O]

6b 72% yield
7b 93% yield, 87% ee

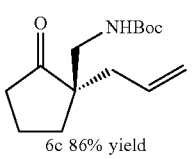

6c 86% yield
7c 98% yield, 82% ee

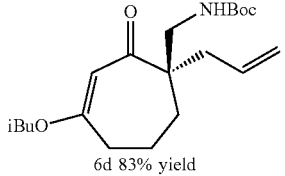

6d 83% yield
7d 70% yield, 92% ee[b]

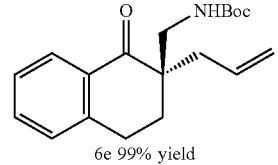

6e 99% yield
7e 74% yield, 93% ee[b]

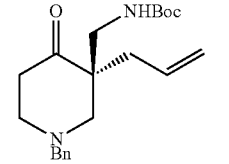 [SMILES: C=CC[C@]1(CNC(=O)OC(C)(C)C)CN(Cc2ccccc2)CCC1=O]

6f 80% yield
7f 78% yield, 90% ee[b]

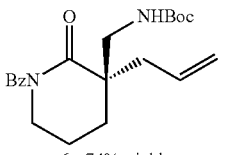

6g 74% yield

TABLE 2-continued

Two-step Synthesis of α-Aminomethyl Carbonyl Compounds from β-Oxo Esters.[a]

7g 97% yield, 90% ee[d]

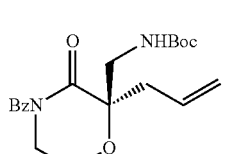

6h 80% yield
7h 92% yield, 99% ee[d]

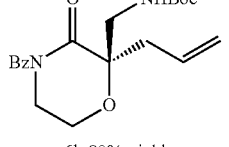

6i 80% yield
7i 51% yield, 92% ee[b,d]

[a]Reaction conditions for step 2: 6 (1 equiv), Pd$_2$(dba)$_3$ (5 mol %) and L1 (12.5 mol %) in toluene (0.033M) at 23° C. for 12-48 h.
[b]Pd$_2$(pmdba)$_3$ (pmdba = bis(4-methoxybenzylidene)acetone) was used instead of Pd$_2$(dba)$_3$.
[c]Enantiomeric excesses were determined by chiral SFC analysis.
[d]Reactions were performed on 6f, 6h, and 6i at 40° C.

As outlined in Table 2, a broad range of ketones and amides (e.g., 5) can easily be converted into enantioenriched tetrasubstituted Mannich-type products (e.g., 7a-i) with this two-step strategy. For all substrates, the first step proceeded in good to excellent yields (72-99%). In the allylic alkylation, 2-phenyl-2-propenyl-substituted 7a was obtained in high yield (91%) and excellent enantioselectivity (90% ee). Cycloheptanone 6b proved to be a good substrate and the corresponding α-quaternary cycloheptanone 7b was isolated in 93% yield and 87% ee, while cyclopentanone 6c gave slightly lower enantioselectivity (82% ee). Vinylogous ester 6d and tetralone 6e afforded α-quaternary vinylogous ester 7d and tetralone 7e in 70% yield and 92% ee, and 74% yield and 93% ee, respectively. Heterocyclic ketone scaffolds were found to be competent substrates for this transformation, as 4-piperidinone 7f was isolated in 78% yield and 90% ee. Lastly, we were pleased to find that under slightly elevated reaction temperatures (40° C.), the desired lactam 7g, morpholinone 7h, and carbazolone 7i were obtained in moderate to excellent yields (51-94%) and excellent enantioselectivities (90-99% ee).

Example 3. Methods for Determining Enantiomeric Excess and Optical Rotation of Alkylation Products

TABLE S-1

| entry | compound | analytic conditions | ee (%) | polarimetry |
|---|---|---|---|---|
| 1 | 4a | SFC: 5% IPA, 2.5 mL/min Chiralpak AD-H, λ = 210 nm $t_R$ (min): major 3.73, minor 4.30 | 86 | $[\alpha]_D^{25}$ −25.5 (c 0.865, $C_6H_6$) |
| 2 | 4b | SFC: 5% IPA, 2.5 mL/min Chiralpak AD-H, λ = 210 nm $t_R$ (min): major 8.12, minor 9.06 | 86 | $[\alpha]_D^{25}$ −38.6 (c 1.20, $CHCl_3$) |
| 3 | 4c | SFC: 10% IPA, 2.5 mL/min Chiralcel OB-H, λ = 210 nm $t_R$ (min): major 9.47, minor 11.13 | 83 | $[\alpha]_D^{25}$ −29.3 (c 0.76, $CHCl_3$) |
| 4 | 4d | SFC: 10% IPA, 2.5 mL/min Chiralcel OB-H, λ = 210 nm $t_R$ (min): major 6.53, minor 8.13 | 77 | $[\alpha]_D^{25}$ −28.9 (c 0.40, $CHCl_3$) |
| 5 | 4e | SFC: 10% IPA, 2.5 mL/min Chiralpak AS-H, λ = 210 nm $t_R$ (min): major 6.94, minor 8.24 | 77 | $[\alpha]_D^{25}$ −27.4 (c 0.78, $CHCl_3$) |
| 6 | 4f | SFC: 20% IPA, 2.5 mL/min Chiralpak AD-H, λ = 210 nm $t_R$ (min): major 4.04, minor 4.91 | 56 | Specific Rotation Not Determined |
| 7 | 4g | SFC: 15% IPA, 2.5 mL/min Chiralcel OJ-H, λ = 210 nm $t_R$ (min): major 3.14, minor 3.85 | 24 | Specific Rotation Not Determined |

TABLE S-2

| entry | compound | analytic conditions | ee (%) | polarimetry |
|---|---|---|---|---|
| 1 | 7a | SFC: 15% IPA, 2.5 mL/min<br>Chiralpak AD-H, λ = 210 nm<br>$t_R$ (min): major 2.46, minor 2.78 | 90 | $[\alpha]_D^{25}$ −30.87<br>(c 4.45, CHCl$_3$) |
| 2 | 7b | SFC: 5% IPA, 2.5 mL/min<br>Chiralpak AD-H, λ = 210 nm<br>$t_R$ (min): major 4.25, minor 4.63 | 87 | $[\alpha]_D^{25}$ −22.7<br>(c 0.85, CHCl$_3$) |
| 3 | 7c | SFC: 5% IPA, 2.5 mL/min<br>Chiralpak AD-H, λ = 210 nm<br>$t_R$ (min): major 2.97, minor 4.26 | 82 | $[\alpha]_D^{25}$ −12.8<br>(c 0.96, CHCl$_3$) |
| 4 | 7d | SFC: 3% IPA, 2.5 mL/min<br>Chiralpak AS-H, λ = 254 nm<br>$t_R$ (min): major 4.41, minor 6.12 | 92 | $[\alpha]_D^{25}$ −28.7<br>(c 0.65, CHCl$_3$) |
| 5 | 7e | SFC: 15% IPA, 2.5 mL/min<br>Chiralpak AD-H, λ = 210 nm<br>$t_R$ (min): major 2.48, minor 2.80 | 93 | $[\alpha]_D^{25}$ −1.3<br>(c 1.32, CHCl$_3$) |
| 6 | 7f | SFC: 8% IPA, 2.5 mL/min<br>Chiralpak AD-H, λ = 210 nm<br>$t_R$ (min): major 4.94, minor 6.46 | 90 | $[\alpha]_D^{25}$ −34.0<br>(c 1.58, CHCl$_3$) |
| 7 | 7g | SFC: 10% MeOH, 3.0 mL/min<br>Chiralpak AD-H, λ = 254 nm<br>$t_R$ (min): major 2.64, minor 3.12 | 90 | $[\alpha]_D^{25}$ +33.6<br>(c 1.05, CHCl$_3$) |
| 8 | 7h | SFC: 3% MeOH, 2.5 mL/min<br>Chiralpak AS-H, λ = 254 nm<br>$t_R$ (min): major 4.06, minor 4.62 | 99 | $[\alpha]_D^{25}$ +10.8<br>(c 0.93, CHCl$_3$) |

TABLE S-2-continued

| entry | compound | analytic conditions | ee (%) | polarimetry |
|---|---|---|---|---|
| 9 | 7i | SFC: 15% IPA, 2.5 mL/min<br>Chiralcel OB-H, λ = 210 nm<br>$t_R$ (min): major 7.21, minor 5.19 | 92 | $[\alpha]_D^{25}$ −13.3<br>(c 0.28, $C_6H_6$) |

Example 4. Total Synthesis of (−)-Isonitramine and (+)-Sibirinine

Scheme 2

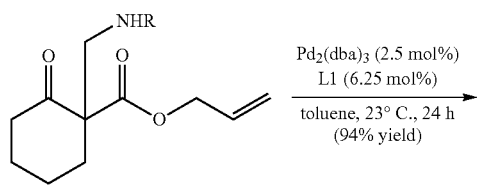

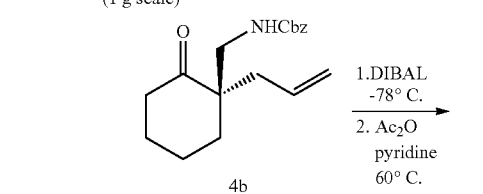

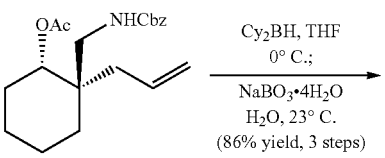

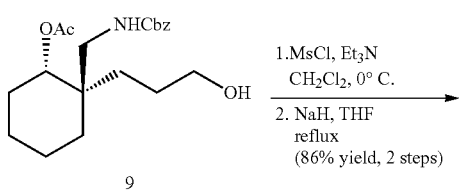

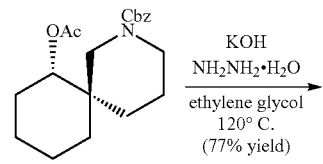

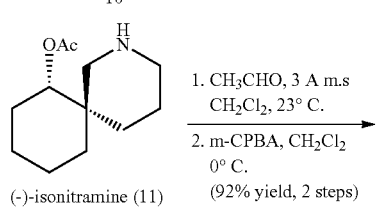

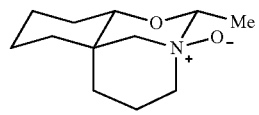

(+)-sibirinine (12)

In order to exhibit the utility of our method for generating interesting and useful chiral building blocks, the first total synthesis of (+)-sibirinine (12) was carried out using β-keto ester 3b as our starting material (Scheme 2). Asymmetric allylic alkylation using one gram of 3b proceeded with one half of the typical catalyst loading without any loss of enantioselectivity. Reduction of β-amino ketone 4b with diisobutylaluminum hydride (DIBAL), followed by acetylation of the resulting alcohol, yielded carbamate 8 as a single diastereomer. Hydroboration of the terminal alkene in carbamate 8 provided primary alcohol 9 in 86% yield over 3 steps. Cyclization of the mesylate derived from primary alcohol 9 smoothly delivered spirocycle 10. Removal of the acetyl and Cbz groups using potassium hydroxide furnished (−)-isonitramine (11) in 77% yield. Treatment of (−)-isonitramine 11 with excess acetaldehyde yielded the desired hemiaminal, which was smoothly oxidized by m-CPBA to give (+)-sibirinine (12) in 92% yield over two steps. Notably, conversion of (−)-isonitramine to (+)-sibirinine can be accomplished in one pot by forming the hemiaminal intermediate under an oxygen atmosphere, albeit in diminished yield. Spectral data of 11 and 12 were identical to those previously reported. Our synthesis of (−)-isonitramine confirms the absolute stereochemistry of 4b.

Synthesis of Alcohol 9

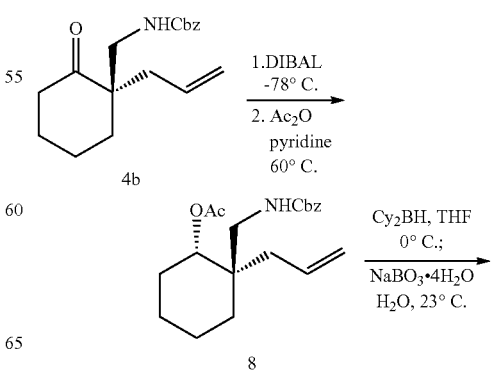

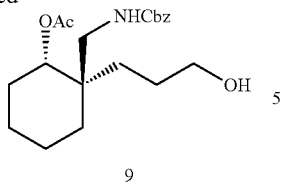

9

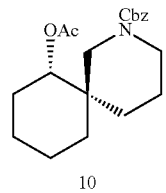

10

To a solution of enantioenriched ketone 4b (851 mg, 2.82 mmol) in CH$_2$Cl$_2$ (14.2 mL) was added DIBAL (6.21 mL, 1.0 M solution in CH$_2$Cl$_2$, 6.21 mmol, 2.20 equiv) dropwise at −78° C. After stirring at −78° C. for 15 min, the reaction mixture was quenched with saturated aqueous Rochelle's salt (20 mL) and stirred at 23° C. for 2 h. The phases were separated and the aqueous phase was extracted with CH$_2$Cl$_2$ (2×25 mL). The combined organic phases were dried over Na$_2$SO$_4$, filtered, and concentrated under reduced pressure. The crude product was used for the next reaction without further purification.

To a solution of the crude alcohol in Ac$_2$O (7.1 mL) was added pyridine (7.1 mL) at room temperature. After full consumption of the starting material was observed by TLC analysis, the reaction mixture was concentrated and azeotropically dried with toluene twice. The resulting residue was used in the next reaction without further purification.

To a flame-dried flask was added cyclohexene (1.43 mL, 14.1 mmol, 5.00 equiv), diethyl ether (10 mL), and BH$_3$·Me$_2$S (7.05 mL, 2.0 M solution in THF, 3.5 mmol, 1.24 equiv) at 0° C. The reaction mixture was stirred at 0° C. for 3 h, then the solid was allowed to settle without stirring, and the supernatant was removed using a syringe. To the resulting solid was added THF (8.0 mL) and a solution of acetate 8 in THF (6.2 mL) at 0° C. After full consumption of acetate 8 by TLC analysis, the reaction mixture was quenched with NaBO$_3$ (3.25 g, 21.2 mmol, 7.52 equiv) and H$_2$O (14 mL) and stirred at room temperature for 1 h. The reaction mixture was diluted with EtOAc, the phases were separated, and the aqueous phase was extracted with EtOAc (2×25 mL). The combined organic phases were dried over Na$_2$SO$_4$, filtered, and concentrated under reduced pressure. Flash column chromatography (SiO$_2$, 30→50% EtOAc in hexanes) afforded alcohol 9 (886 mg, 86% yield, over 3 steps) as a colorless oil. $[\alpha]_D^{25}$ +7.5 (c 0.95, CHCl$_3$); R$_f$=0.33 (50% EtOAc in hexanes); $^1$H NMR (500 MHz, CDCl$_3$) δ 7.39-7.28 (m, 5H), 5.35 (m, 1H), 5.14-5.02 (m, 2H), 4.77 (dd, J=9.7, 4.5 Hz, 1H), 3.68-3.58 (m, 2H), 3.30 (dd, J=14.3, 8.0 Hz, 1H), 2.88 (dd, J=14.2, 5.5 Hz, 1H), 2.05 (s, 3H), 1.71-1.16 (m, 12H); $^{13}$C NMR (126 MHz, CDCl$_3$) δ 171.4, 157.1, 136.7, 128.6, 128.3, 128.2, 75.3, 66.9, 63.5, 45.5, 40.9, 30.0, 26.9, 26.0, 25.3, 23.9, 21.4, 20.4; IR (Neat Film, NaCl) 3385, 2937, 2866, 1718, 1528, 1455, 1374, 1247, 1026 cm$^{-1}$; HRMS (ESI+) m/z calc'd for C$_{20}$H$_{30}$NO$_5$ [M+H]$^+$: 364.2118. found 364.2109.

Synthesis of Spiroamine 10

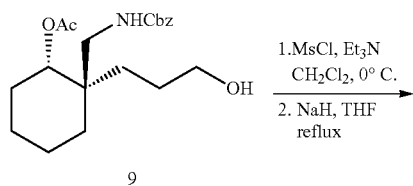

To a solution of primary alcohol 9 (865 mg, 2.38 mmol) in CH$_2$Cl$_2$ (12 mL) was added Et$_3$N (0.497 mL, 3.57 mmol, 1.50 equiv) and MsCl (0.203 mL, 2.63 mmol, 1.10 equiv) at 0° C. After full consumption of alcohol 9 was observed by TLC analysis, the reaction mixture was quenched with saturated aqueous NaHCO$_3$ (25 mL) and the phases were separated. The aqueous phase was extracted with CH$_2$Cl$_2$ (2×25 mL). The combined organic phases were dried over Na$_2$SO$_4$, filtered, and concentrated under reduced pressure. The crude product was used in the next reaction without further purification.

To a suspension of sodium hydride (114 mg, 60 wt % dispersion in mineral oil, 2.86 mmol) in THF (6 mL) was added a solution of the above methanesulfonate in THF (6 mL) at 0° C. The reaction mixture was stirred at reflux for 2 h. Upon cooling to 23° C., the reaction mixture was quenched with saturated aqueous NH$_4$Cl (20 mL) and diluted with CH$_2$Cl$_2$ (20 mL). The phases were separated, and the aqueous phase was extracted with CH$_2$Cl$_2$ (3×25 mL). The combined organic phases were dried over Na$_2$SO$_4$, filtered, and concentrated under reduced pressure. Flash column chromatography (SiO$_2$, 15% EtOAc in hexanes) afforded spirocyclic carbamate 10 (732 mg, 89% yield, over 2 steps) as a colorless oil. $[\alpha]_D^{25}$ +46.8 (c 0.97, CHCl$_3$); R$_f$=0.57 (33% EtOAc in hexanes); $^1$H NMR (500 MHz, CDCl$_3$, mixture of rotamers) δ 7.39-7.26 (m, 5H), 5.20-5.01 (m, 2H), 4.86-4.61 (m, 1H), 3.96-2.91 (m, 4H), 2.05 (s, 3H), 1.87-1.00 (m, 12H); $^{13}$C NMR (126 MHz, CDCl$_3$, mixture of rotamers) δ 170.6, 155.7, 137.0, 128.6, 128.1, 128.0, 75.2 (74.3), 67.2, 51.4 (50.7), 44.8, 37.0 (36.9), 30.6 (29.1), 30.2, 26.5, 22.4 (21.8), 21.3, 20.8 (20.7), 20.6 (20.5); IR (Neat Film, NaCl) 2938, 2861, 1732, 1699, 1434, 1242 cm$^{-1}$; HRMS (ESI+) m/z calc'd for C$_{20}$H$_{29}$NO$_4$ [M+H]$^+$: 346.2013. found 346.2016.

Synthesis of (−)-isonitramine (11)

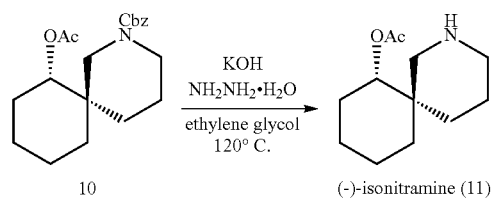 [SMILES: CC(=O)O[C@H]1CCCC[C@@]12CCCN(C(=O)OCc1ccccc1)C2 ; CC(=O)O[C@H]1CCCC[C@@]12CCCNC2]

To a solution of spirocyclice carbamate 10 (712 mg, 2.06 mmol) in ethylene glycol (13 mL) was added KOH (3.00 g, 53.4 mmol, 25.92 equiv) and hydrazine hydrate (0.51 mL) at 23° C. After stirring at 120° C. for 1.5 h, the reaction mixture cooled to 23° C. and diluted with H$_2$O (100 mL). The aqueous phase was extracted with CH$_2$Cl$_2$ (200 mL) using a continuous liquid/liquid extractor and the organic phase was concentrated under reduced pressure. Flash column chromatography (SiO$_2$, CHCl$_3$:MeOH:NH$_3$(aq)=46:50:4 eluent)

afforded (−)-isonitramine (11) (270 mg, 77% yield) as a white solid. $[\alpha]_D^{25}$ −4.1 (c 0.96, CHCl$_3$); Lit: $[\alpha]_D^{20}$ −5.0 (c 2.1, CHCl$_3$); $R_f$=0.30 (CHCl$_3$:MeOH:NH$_3$(aq)=46:50:4); m.p. 86.9-88.8° C.; $^1$H NMR (500 MHz, CDCl$_3$) δ 3.66 (dd, J=11.3, 3.7 Hz, 1H), 3.04 (m, 1H), 2.94 (m, 1H), 2.60 (ddd, J=11.3, 11.3, 3.4 Hz, 1H), 2.52 (d, J=11.3 Hz, 1H), 2.24 (m, 1H), 2.06 (m, 1H), 1.78-1.14 (m, 8H), 1.06 (ddd, J=13.3, 13.3, 5.5 Hz, 1H), 0.96 (m, 1H); $^{13}$C NMR (126 MHz, CDCl$_3$) δ 80.7, 61.0, 47.4, 36.9, 36.3, 29.9, 29.0, 24.4, 23.3, 20.4; IR (Neat Film, NaCl) 3292, 2929, 2858, 1539, 1457, 1419, 1282, 1064 cm$^{-1}$; HRMS (ESI+) m/z calc'd for C$_{10}$H$_{20}$NO [M+H]$^+$: 170.1539. found 170.1541.

Synthesis of (+)-sibirinine (12)

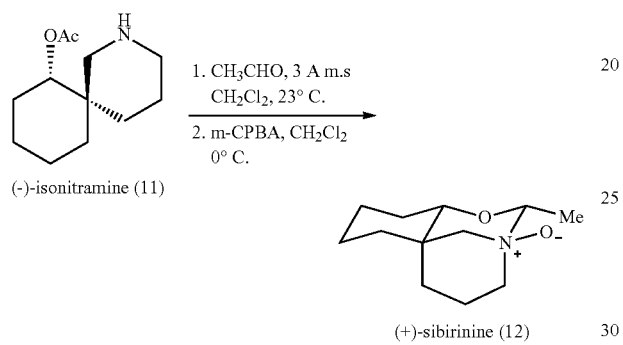

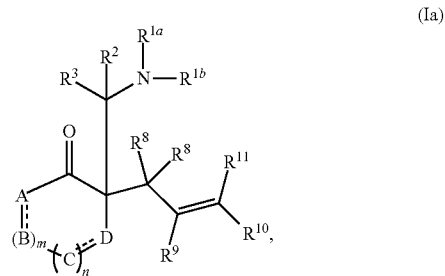

An oven-dried 1-dram vial was charged with a magnetic stirring bar, 11 (20 mg, 0.118 mmol), powdered 3 Å molecular sieves (40 mg), and CH$_2$Cl$_2$ (1.5 mL). To this stirring suspension was added acetaldehyde (0.133 mL, 2.36 mmol, 20.0 equiv). The vial was sealed with a teflon cap, and the reaction was stirred at 23° C. for 30 h. The reaction mixture was then filtered through celite, washing with CH$_2$Cl$_2$. The filtrate was concentrated under reduced pressure to yield a pale yellow oil, which was used in the subsequent reaction without further purification.

The above crude hemiaminal was dissolved in CH$_2$Cl$_2$ (1.2 mL) and cooled to 0° C. (water/ice bath). To this stirring solution was added m-CPBA (29 mg, 0.13 mmol) in one portion. After 15 min, full consumption of starting material was observed by TLC analysis. The reaction mixture was filtered through celite, washing with CH$_2$Cl$_2$, and concentrated under reduced pressure. Flash column chromatography (SiO$_2$, CH$_2$Cl$_2$: NH$_3$ (7N solution in MeOH)=92:8 eluent) afforded (+)-sibirinine (12) (22.9 mg, 92% yield, over 2 steps) as a colorless oil. $[\alpha]_D^{25}$ +10.3 (c 0.56, CHCl$_3$); $R_f$=0.40 (CH$_2$Cl$_2$: NH$_3$ (7N solution in MeOH)=9:1); $^1$H NMR (500 MHz, CDCl$_3$) δ 4.50 (qd, J=5.8, 1.5 Hz, 1H), 3.73 (dd, J=13.4, 7.1 Hz, 1H), 3.53 (ddd, J=12.0, 4.1, 1.5 Hz, 1H), 3.21 (d, J=12.2 Hz, 1H), 3.11 (dt, J=12.2, 2.5 Hz, 1H), 3.03 (dddd, J=14.7, 13.4, 5.5, 1.6 Hz, 1H), 2.45 (tdt, J=14.4, 13.5, 5.9 Hz, 1H), 2.32 (dd, J=14.1, 5.8 Hz, 1H), 1.87 (dtd, J=13.1, 3.8, 1.7 Hz, 1H), 1.79 (dq, J=12.3, 3.6 Hz, 1H), 1.65 (d, J=5.8 Hz, 3H), 1.64-1.60 (m, 1H), 1.57-1.46 (m, 2H), 1.46 (dt, J=13.0, 4.0 Hz, 1H), 1.41-1.31 (m, 2H), 1.23 (m, 1H), 1.17 (m, 1H); $^{13}$C NMR (126 MHz, CDCl$_3$) δ 102.2, 84.4, 77.8, 62.5, 38.2, 34.7, 27.0, 26.3, 24.7, 21.2, 19.6, 14.6; IR (Neat Film, NaCl) 2934, 2854, 1466, 1446, 1367, 1138, 1120, 1103, 961, 940 cm$^{-1}$; HRMS (ESI/APCI) m/z calc'd for C$_{12}$H$_{22}$NO$_2$ [M+H]$^+$: 212.1645. found 212.1640.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:
1. A compound represented by formula (Ia),

(Ia)

or a salt thereof;
wherein:
A, B, C, and D each independently represent, as valence permits, NR', CR"R'", C(O), O, S, CR", or N; provided that at least one occurrence of A, B, C, and D is NR' and at least one occurrence of the remaining A, B, C, and D is NR' or O; and provided that no two adjacent occurrences of A, B, C, and D are NR', O, S, or N;
R' represents hydrogen or optionally substituted alkyl, cycloalkyl, (cycloalkyl)alkyl, aryl, aralkyl, heteroaryl, heteroaralkyl, alkenyl, alkynyl, —C(O)alkyl, —C(O)aryl, —C(O)aralkyl, —C(O)heteroaryl, —C(O)heteroaralkyl, —C(O)O(alkyl), —C(O)O(aryl), —C(O)O(aralkyl), —C(O)O(heteroaryl), —C(O)O(heteroaralkyl), —S(O)$_2$(aryl), —S(O)$_2$(alkyl), —S(O)$_2$(haloalkyl), —OR$^{14}$, —SR$^{14}$, or —NR$^{14}$R$^{15}$;
R" and R'" each independently represent hydrogen, hydroxyl, halogen, nitro, alkyl, cycloalkyl, (cycloalkyl)alkyl, aryl, aralkyl, heteroaryl, heteroaralkyl, (heterocycloalkyl)alkyl, heterocycloalkyl, alkenyl, alkynyl, cyano, carboxyl, sulfate, amino, alkoxy, aryloxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, acyl, acyloxy, or acylamino;
or any two occurrences of R', R", and R'" on adjacent A, B, C, or D groups, taken together with the intervening atoms, form an optionally substituted aryl, heteroaryl, cycloalkyl, cycloalkenyl, heterocycloalkyl, or heterocycloalkenyl group;
each occurrence of ═══ independently represents a double bond or a single bond as permitted by valence;

m and n are integers each independently selected from 0, 1, and 2, wherein the sum of m and n is 1, 2, 3, or 4;

$R^{1a}$ and $R^{1b}$ each independently represent hydrogen or optionally substituted alkyl, cycloalkyl, (cycloalkyl)alkyl, aryl, aralkyl, heteroaryl, heteroaralkyl, alkenyl, alkynyl, —C(O)alkyl, —C(O)aryl, —C(O)aralkyl, —C(O)heteroaryl, —C(O)heteroaralkyl, —C(O)O(alkyl), —C(O)O(aryl), —C(O)O(aralkyl), —C(O)O(heteroaryl), —C(O)O(heteroaralkyl), —S(O)$_2$(aryl), —S(O)$_2$(alkyl), —S(O)$_2$(haloalkyl), —OR$^{14}$, —SR$^{14}$, or —NR$^{14}$R$^{15}$;

$R^2$ and $R^3$ each independently represent hydrogen or substituted or unsubstituted alkyl, aralkyl, aryl, heteroaralkyl, heteroaryl, (cycloalkyl)alkyl, cycloalkyl, (heterocycloalkyl)alkyl, heterocycloalkyl, alkenyl, alkynyl, alkylamino, hydroxyalkyl, alkoxyalkyl, aminoalkyl, or thioalkyl;

$R^8$, $R^9$, $R^{10}$, and $R^{11}$ are independently selected for each occurrence from hydrogen, hydroxyl, halogen, nitro, alkyl, alkenyl, alkynyl, cyano, carboxyl, sulfate, amino, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, acyl, acyloxy, acylamino, aryl, heteroaryl, cycloalkyl, heterocycloalkyl, aralkyl, arylalkoxy, heteroaralkyl, (cycloalkyl)alkyl, and (heterocycloalkyl)alkyl; and $R^{14}$ and $R^{15}$ are independently selected for each occurrence from hydrogen or substituted or unsubstituted alkyl, aralkyl, aryl, heteroaralkyl, heteroaryl, (cycloalkyl)alkyl, cycloalkyl, (heterocycloalkyl)alkyl, heterocycloalkyl, alkenyl, and alkynyl, wherein the compound represented by formula (Ia) is enantioenriched.

2. The compound of claim 1, wherein the sum of m and n is 1, 2, or 3.

3. The compound of claim 1, wherein m is 1 or 2; n is 1 or 2; and at least two adjacent occurrences of A, B, C, and D are CR".

4. The compound of claim 3, wherein A and B are each CR"; m is 1; n is 2; and
R" is independently selected for each occurrence from hydrogen, hydroxyl, halogen, alkyl, cycloalkyl, (cycloalkyl)alkyl, aryl, aralkyl, heteroaryl, heteroaralkyl, (heterocycloalkyl)alkyl, heterocycloalkyl, alkenyl, alkynyl, amino, alkoxy, aryloxy, and alkylamino; or
the occurrence of R" on A and the occurrence of R" on B are taken together to form an optionally substituted aryl, heteroaryl, cycloalkenyl, or heterocycloalkenyl group.

5. The compound of claim 1, wherein R' represents independently for each occurrence hydrogen or optionally substituted alkyl, aralkyl, heteroaralkyl, —C(O)alkyl, —C(O)aryl, —C(O)aralkyl, —C(O)O(alkyl), —C(O)O(aryl), —C(O)O(aralkyl), or —S(O)$_2$(aryl).

6. The compound of claim 1, wherein $R^8$, $R^9$, $R^{10}$, and $R^{11}$ are each hydrogen.

7. The compound of claim 1, wherein $R^2$ and $R^3$ are each hydrogen.

8. The compound of claim 1, wherein $R^{1a}$ represents hydrogen or optionally substituted alkyl, —C(O)alkyl, —C(O)aryl, —C(O)aralkyl, —C(O)O(alkyl), —C(O)O(aryl), —C(O)O(aralkyl), or —S(O)$_2$(aryl).

9. The compound of claim 1, wherein $R^{1b}$ represents hydrogen.

10. The compound of claim 1, wherein the compound represented by formula (Ia) has about 70% ee or greater.

11. The compound of claim 1, wherein the compound represented by formula (Ia) has about 80% ee or greater.

12. The compound of claim 1, wherein the compound represented by formula (Ia) has about 85% ee or greater.

13. The compound of claim 1, wherein the compound represented by formula (Ia) has about 90% ee or greater.

14. A compound represented by formula (IIa),

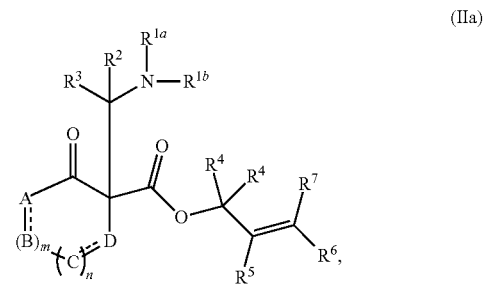

(IIa)

or a pharmaceutically acceptable salt thereof;
wherein:

A, B, C, and D each independently represent, as valence permits, NR', CR"R''', C(O), O, S, CR", or N; provided that at least one occurrence of A, B, C, and D is NR' and at least one occurrence of the remaining A, B, C, and D is NR' or O; and provided that no two adjacent occurrences of A, B, C, and D are NR', O, S, or N;

R' represents hydrogen or optionally substituted alkyl, cycloalkyl, (cycloalkyl)alkyl, aryl, aralkyl, heteroaryl, heteroaralkyl, alkenyl, alkynyl, —C(O)alkyl, —C(O)aryl, —C(O)aralkyl, —C(O)heteroaryl, —C(O)heteroaralkyl, —C(O)O(alkyl), —C(O)O(aryl), —C(O)O(aralkyl), —C(O)O(heteroaryl), —C(O)O(heteroaralkyl), —S(O)$_2$(aryl), —S(O)$_2$(alkyl), —S(O)$_2$(haloalkyl), —OR$^{14}$, —SR$^{14}$, or —NR$^{14}$R$^{15}$;

R" and R''' each independently represent hydrogen, hydroxyl, halogen, nitro, alkyl, cycloalkyl, (cycloalkyl)alkyl, aryl, aralkyl, heteroaryl, heteroaralkyl, (heterocycloalkyl)alkyl, heterocycloalkyl, alkenyl, alkynyl, cyano, carboxyl, sulfate, amino, alkoxy, aryloxy, alkylamino, alkylthio, hydroxyalkyl, alkoxyalkyl, aminoalkyl, thioalkyl, ether, thioester, ester, amide, thioester, carbonate, carbamate, urea, sulfonate, sulfone, sulfoxide, sulfonamide, acyl, acyloxy, or acylamino;

or any two occurrences of R', R", and R''' on adjacent A, B, C, or D groups, taken together with the intervening atoms, form an optionally substituted aryl, heteroaryl, cycloalkyl, cycloalkenyl, heterocycloalkyl, or heterocycloalkenyl group;

each occurrence of === independently represents a double bond or a single bond as permitted by valence;

m and n are integers each independently selected from 0, 1, and 2, wherein the sum of m and n is 1, 2, 3, or 4;

$R^{1a}$ and $R^{1b}$ each independently represent hydrogen or optionally substituted alkyl, cycloalkyl, (cycloalkyl)alkyl, aryl, aralkyl, heteroaryl, heteroaralkyl, alkenyl, alkynyl, —C(O)alkyl, —C(O)aryl, —C(O)aralkyl, —C(O)heteroaryl, —C(O)heteroaralkyl, —C(O)O(alkyl), —C(O)O(aryl), —C(O)O(aralkyl), —C(O)O(heteroaryl), —C(O)O(heteroaralkyl), —S(O)$_2$(aryl), —S(O)$_2$(alkyl), —S(O)$_2$(haloalkyl), —OR$^{14}$, —SR$^{14}$, or —NR$^{14}$R$^{15}$;

$R^2$ and $R^3$ each independently represent hydrogen or substituted or unsubstituted alkyl, aralkyl, aryl, heteroaralkyl, heteroaryl, (cycloalkyl)alkyl, cycloalkyl, (heterocycloalkyl)alkyl, heterocycloalkyl, alkenyl, alkynyl, alkylamino, hydroxyalkyl, alkoxyalkyl, aminoalkyl, or thioalkyl;

$R^4$, $R^5$, $R^6$, and $R^7$ are independently selected for each occurrence from hydrogen, hydroxyl, halogen, nitro, alkyl, alkenyl, alkynyl, cyano, carboxyl, sulfate, amino, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, acyl, acyloxy, acylamino, aryl, heteroaryl, cycloalkyl, heterocycloalkyl, aralkyl, arylalkoxy, heteroaralkyl, (cycloalkyl)alkyl, and (heterocycloalkyl)alkyl; and $R^{14}$ and $R^{15}$ are independently selected for each occurrence from hydrogen or substituted or unsubstituted alkyl, aralkyl, aryl, heteroaralkyl, heteroaryl, (cycloalkyl)alkyl, cycloalkyl, (heterocycloalkyl)alkyl, heterocycloalkyl, alkenyl, and alkynyl.

15. A method for the preparation of a compound of formula (Ia):

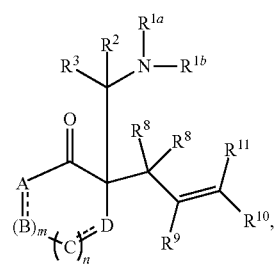

comprising treating a compound of formula (IIa):

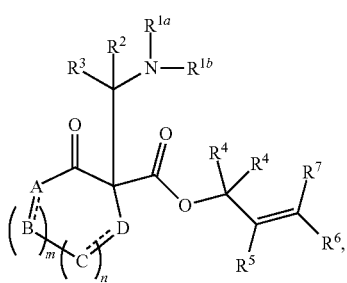

with a transition metal catalyst under alkylation conditions, wherein, as valence and stability permit, A, B, C, and D each independently represent, as valence permits, NR', CR"R'", C(O), O, S, CR", or N; provided that at least one occurrence of A, B, C, and D is NR' and at least one occurrence of the remaining A, B, C, and D is NR' or O; and provided that no two adjacent occurrences of A, B, C, and D are NR', O, S, or N;

R' represents hydrogen or optionally substituted alkyl, cycloalkyl, (cycloalkyl)alkyl, aryl, aralkyl, heteroaryl, heteroaralkyl, alkenyl, alkynyl, —C(O)alkyl, —C(O)aryl, —C(O)aralkyl, —C(O)heteroaryl, —C(O)heteroaralkyl, —C(O)O(alkyl), —C(O)O(aryl), —C(O)O(aralkyl), —C(O)O(heteroaryl), —C(O)O(heteroaralkyl), —S(O)$_2$(aryl), —S(O)$_2$(alkyl), —S(O)$_2$(haloalkyl), —OR$^{14}$, —SR$^{14}$, or —NR$^{14}$R$^{15}$;

R" and R'" each independently represent hydrogen, hydroxyl, halogen, nitro, alkyl, cycloalkyl, (cycloalkyl)alkyl, aryl, aralkyl, heteroaryl, heteroaralkyl, (heterocycloalkyl)alkyl, heterocycloalkyl, alkenyl, alkynyl, cyano, carboxyl, sulfate, amino, alkoxy, aryloxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, acyl, acyloxy, or acylamino;

or any two occurrences of R', R", and R'" on adjacent A, B, C, or D groups, taken together with the intervening atoms, form an optionally substituted aryl, heteroaryl, cycloalkyl, cycloalkenyl, heterocycloalkyl, or heterocycloalkenyl group;

each occurrence of === independently represents a double bond or a single bond as permitted by valence;

m and n are integers each independently selected from 0, 1, and 2, wherein the sum of m and n is 1, 2, 3, or 4;

$R^{1a}$ and $R^{1b}$ each independently represent hydrogen or optionally substituted alkyl, cycloalkyl, (cycloalkyl)alkyl, aryl, aralkyl, heteroaryl, heteroaralkyl, alkenyl, alkynyl, —C(O)alkyl, —C(O)aryl, —C(O)aralkyl, —C(O)heteroaryl, —C(O)heteroaralkyl, —C(O)O(alkyl), —C(O)O(aryl), —C(O)O(aralkyl), —C(O)O(heteroaryl), —C(O)O(heteroaralkyl), —S(O)$_2$(aryl), —S(O)$_2$(alkyl), —S(O)$_2$(haloalkyl), —OR$^{14}$, —SR$^{14}$, or —NR$^{14}$R$^{15}$;

$R^2$ and $R^3$ each independently represent hydrogen or substituted or unsubstituted alkyl, aralkyl, aryl, heteroaralkyl, heteroaryl, (cycloalkyl)alkyl, cycloalkyl, (heterocycloalkyl)alkyl, heterocycloalkyl, alkenyl, alkynyl, alkylamino, hydroxyalkyl, alkoxyalkyl, aminoalkyl, or thioalkyl;

$R^4$, $R^5$, $R^6$, $R^7$, $R^8$, $R^9$, $R^{10}$, and $R^{11}$ are each independently selected for each occurrence from hydrogen, hydroxyl, halogen, nitro, alkyl, alkenyl, alkynyl, cyano, carboxyl, sulfate, amino, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, acyl, acyloxy, acylamino, aryl, heteroaryl, cycloalkyl, heterocycloalkyl, aralkyl, arylalkoxy, heteroaralkyl, (cycloalkyl)alkyl, and (heterocycloalkyl)alkyl; and $R^{14}$ and $R^{15}$ are independently selected for each occurrence from hydrogen or substituted or unsubstituted alkyl, aralkyl, aryl, heteroaralkyl, heteroaryl, (cycloalkyl)alkyl, cycloalkyl, (heterocycloalkyl)alkyl, heterocycloalkyl, alkenyl, and alkynyl, wherein the compound represented by formula (Ia) has about 70% ee or greater.

16. The method of claim 15, wherein the transition metal catalyst comprises a transition metal selected from palladium, nickel, and platinum.

17. The method of claim 15, wherein the transition metal catalyst further comprises a chiral ligand.

18. The method of claim 15, wherein the compound represented by formula (Ia) has about 80% ee or greater.

19. The method of claim 15, wherein the compound represented by formula (Ia) has about 85% ee or greater.

20. The method of claim 15, wherein the compound represented by formula (Ia) has about 90% ee or greater.

* * * * *